US012577216B2

(12) United States Patent
Chen et al.

(10) Patent No.: US 12,577,216 B2
(45) Date of Patent: Mar. 17, 2026

(54) TRIAZINE BENZOATE COMPOUND AND APPLICATION THEREOF

(71) Applicants: SHENYANG SINOCHEM AGROCHEMICALS R&D CO., LTD., Liaoning (CN); JIANGSU YANGNONG CHEMICAL CO., LTD., Jiangsu (CN)

(72) Inventors: Lin Chen, Liaoning (CN); Huibin Yang, Liaoning (CN); Hongjuan Ma, Liaoning (CN); Gang Wang, Liaoning (CN); Dongliang Cui, Liaoning (CN); Bin Li, Liaoning (CN)

(73) Assignees: SHENYANG SINOCHEM AGROCHEMICALS R&D CO., LTD., Liaoning (CN); JIANGSU YANGNONG CHEMICAL CO., LTD., Jiangsu (CN)

( * ) Notice: Subject to any disclaimer, the term of this patent is extended or adjusted under 35 U.S.C. 154(b) by 428 days.

(21) Appl. No.: 18/002,421

(22) PCT Filed: Jun. 22, 2021

(86) PCT No.: PCT/CN2021/101396

§ 371 (c)(1),
(2) Date: Dec. 19, 2022

(87) PCT Pub. No.: WO2021/259224

PCT Pub. Date: Dec. 30, 2021

(65) Prior Publication Data

US 2023/0227415 A1 Jul. 20, 2023

(30) Foreign Application Priority Data

Jun. 23, 2020 (CN) ......................... 202010582153.7
Jun. 23, 2020 (CN) ......................... 202010582185.7

(51) Int. Cl.

| | |
|---|---|
| *C07D 251/32* | (2006.01) |
| *A01N 43/64* | (2006.01) |
| *A01P 13/00* | (2006.01) |
| *C07D 251/38* | (2006.01) |
| *C07D 405/12* | (2006.01) |

(52) U.S. Cl.

CPC ........... *C07D 251/32* (2013.01); *A01N 43/64* (2013.01); *A01P 13/00* (2021.08); *C07D 251/38* (2013.01); *C07D 405/12* (2013.01)

(58) Field of Classification Search

CPC ..... C07D 251/32; C07D 251/38; A01N 43/64
See application file for complete search history.

(56) References Cited

U.S. PATENT DOCUMENTS 5,447,904 A 9/1995 Schallner et al.
6,602,825 B1 * 8/2003 Menke .................. A01N 53/00 540/607

FOREIGN PATENT DOCUMENTS

CN 1341105 A 3/2002
WO 2019162702 A1 8/2019

* cited by examiner

*Primary Examiner* — Bethany P Barham
*Assistant Examiner* — Danielle Johnson
(74) *Attorney, Agent, or Firm* — NKL Law; Allen Xue

(57) ABSTRACT

The present invention discloses a triazine benzoate compound having the structure shown in formula (I) or a stereoisomer:

(I)

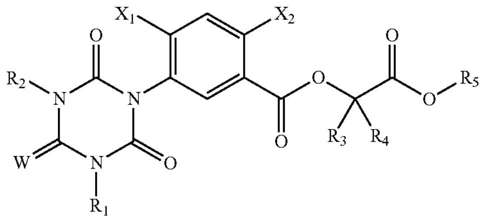

The definition of each substituent in the formula I is described in the description. The compound of the formula I of the present invention has excellent herbicidal activity and can be used for controlling weeds.

3 Claims, No Drawings

TRIAZINE BENZOATE COMPOUND AND APPLICATION THEREOF

TECHNICAL FIELD

The present invention belongs to the field of herbicides, and particularly relates to a triazine benzoate compound and an application thereof.

BACKGROUND

Due to the succession and change of weed populations and the emergence and rapid development of resistance to chemical pesticides, people have continuously strengthened awareness on ecological environmental protection, and have paid more attention to the knowledge of chemical pesticide pollution and the influence of pesticides on non-target organisms and the end-result problem in the pesticide ecological environment. With the gradual decrease of the arable land area in the world, the continuous increase of the population and the increase of the demands for food, people are forced to rapidly develop agricultural production technologies, enhance and improve the farming system, and continuously invent novel and improved herbicidal compounds and compositions.

CN1341105A has disclosed that a compound having the following formula has herbicidal activity:

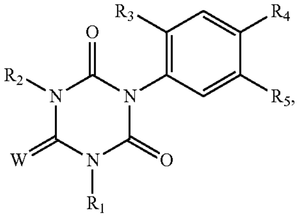

wherein $R_5$ can be a carboxylate substituent $COOR_{20}$. $R_{20}$ can be selected from $C_1$-$C_6$-alkyl, $C_1$-$C_6$-haloalkyl, $C_2$-$C_6$-alkenyl or $C_2$-$C_6$-alkynyl, and can be further replaced with ($C_1$-$C_6$-alkoxy)carbonyl, ($C_3$-$C_6$-alkenoxy)carbonyl, ($C_3$-$C_6$-alkynyloxy)carbonyl or $C_1$-$C_6$-alkoxy-($C_1$-$C_6$-alkoxy) carbonyl. CN1341105A has disclosed that compound $KC_1$ (compound 30 in Table 3 of patent description) can effectively control *Amaranthus retroflexus, Chenopodium album* L., *Commelina benghalensis* Linn. and *Setaria faberi* through a postemergence application method under the doses of 7.81 and 3.91 g/ha, and also has disclosed preparation of compound $KC_2$ (R body, compound 12 in Table 3 of patent description) with photoactivity, but does not report the herbicidal activity.

$KC_1$

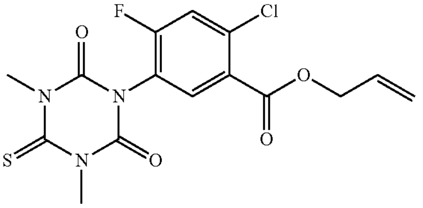

-continued $KC_2$

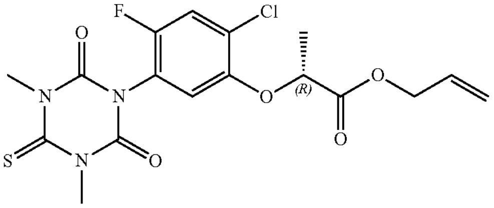

In the prior art, the triazine benzoate compound shown in the present invention and herbicidal activity thereof have not been disclosed.

SUMMARY

The purpose of the present invention is to provide a triazine benzoate compound with novel structure and good herbicidal activity, and a herbicidal composition that takes the compound as an active ingredient, to satisfy the need of rapid development of production.

The present invention has the following technical solution:

The present invention provides a novel triazine benzoate compound having a structure shown in formula (I):

(I)

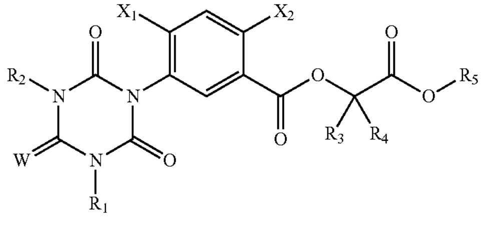

wherein:

W is selected from O or S;

$X_1$ is selected from H or F;

$X_2$ is selected from halogen, CN, $CONH_2$ or $CSNH_2$;

$R_1$ is selected from methyl or ethyl;

$R_2$ is selected from methyl or ethyl;

$R_3$ is selected from H or methyl;

$R_4$ is selected from H or $C_1$-$C_3$ alkyl;

$R_5$ is selected from $CH_3CH_2$—, $CH_3CH_2CH_2$—, $(CH_3)_2CH$—, $CH_3CH_2CH_2CH_2$—, $(CH_3)_2CHCH_2$—, $CH_3CH_2CH(CH_3)$—, $(CH_3)_3C$—, $CH_3CH_2CH_2CH_2CH_2$—, $(CH_3)_2CHCH_2CH_2$—, $(CH_3)_3CCH_2$—, $CH_3CH_2CH(CH_3)CH_2$—, $CH_3CH_2CH_2CH(CH_3)$—, $CH_3CH_2C(CH_3)_2$—, $CH_3CH{=}CHCH_2$—, $CH_3C{\equiv}CCH_2$—, $C_1$-$C_{10}$ haloalkyl, $C_1$-$C_6$ alkylthio $C_1$-$C_6$ alkyl, $C_1$-$C_6$ alkylsulfinyl $C_1$-$C_6$ alkyl, $C_1$-$C_6$ alkylsulfonyl $C_1$-$C_6$ alkyl, ($C_1$-$C_6$ alkyl)$_2$ amino $C_1$-$C_6$ alkyl, $C_3$-$C_{10}$ cycloalkyl, $C_3$-$C_6$ cycloalkyl $C_1$-$C_6$ alkyl, $C_3$-$C_{10}$ halocycloalkyl, $C_3$-$C_6$ halocycloalkyl $C_1$-$C_6$ alkyl, $C_2$-$C_{10}$ haloalkenyl, $C_1$-$C_6$ alkoxy $C_2$-$C_6$ alkenyl, $C_1$-$C_6$ alkylthio $C_2$-$C_6$ alkenyl, $C_1$-$C_6$ alkylsulfinyl $C_2$-$C_6$ alkenyl, $C_1$-$C_6$ alkylsulfonyl $C_2$-$C_6$ alkenyl, ($C_1$-$C_6$ alkyl)$_2$ amino $C_2$-$C_6$ alkenyl, $C_3$-$C_{10}$ cycloalkenyl, $C_3$-$C_6$ cycloalkyl $C_2$-$C_6$ alkenyl, $C_3$-$C_6$ halocycloalkyl $C_2$-$C_6$ alkenyl, $C_2$-$C_{10}$ haloalkynyl, $C_1$-$C_6$ alkoxy $C_2$-$C_6$ alkynyl, $C_1$-$C_6$ alkylthio $C_2$-$C_6$ alkynyl, $C_1$-$C_6$ alkylsulfinyl $C_2$-$C_6$ alkynyl, $C_1$-$C_6$ alkylsulfonyl $C_2$-$C_6$ alkynyl, ($C_1$-$C_6$ alkyl)$_2$ amino $C_2$-$C_6$ alkynyl, $C_3$-$C_{10}$ cycloalkynyl, $C_3$-$C_6$ cycloalkyl $C_2$-$C_6$ alkynyl, $C_3$-$C_6$ halocycloalkyl $C_2$-$C_6$ alkynyl, phenyl, phenyl $C_1$-$C_6$ alkyl, 5-7-membered alicyclic heterocycle containing 1-4 heteroatoms, 5-7-membered aromatic heterocycle containing 1-4 heteroatoms, 5-7-membered alicyclic heterocyclic $C_1$-$C_6$ alkyl containing 1-4 heteroatoms or 5-7 membered aromatic heterocyclic $C_1$-$C_6$ alkyl containing 1-4 heteroatoms; hydrogens on the above phenyl, alicyclic heterocycle and aromatic heterocycle can be substituted by one or more of the following substituents; and the substituents are selected from nitro, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_3$-$C_6$ cycloalkoxy, $C_2$-$C_6$ alkenyl, $C_2$-$C_6$ alkynyl, phenyl or phenyl which is substituted by one or more halogens;

or, an optical isomer of the compound shown in formula I when $R_3$ is selected from H and $R_4$ is not selected from H.

A further preferred compound in the present invention is: in the formula I:

W is selected from O or S;

$X_1$ is selected from H or F;

$X_2$ is selected from Cl, Br or CN;

$R_1$ is selected from methyl;

$R_2$ is selected from methyl;

$R_3$ is selected from H or methyl;

$R_4$ is selected from H, methyl, ethyl or isopropyl;

$R_5$ is selected from $CH_3CH_2$—, $CH_3CH_2CH_2$—, $(CH_3)_2CH$—, $CH_3CH_2CH_2CH_2$—, $(CH_3)_2CHCH_2$—, $CH_3CH_2CH(CH_3)$—, $(CH_3)_3C$—, $CH_3CH_2CH_2CH_2CH_2$—, $(CH_3)_2CHCH_2CH_2$—, $(CH_3)_3CCH_2$—, $CH_3CH_2CH(CH_3)CH_2$—, $CH_3CH_2CH_2CH(CH_3)$—, $CH_3CH_2C(CH_3)_2$—, $ClCH_2CH_2$—, $ClCH_2CH_2CH_2$—, $CH_3ClCHCH_2$—, $CH_2Cl(CH_3)CH$—, $ClCH_2CH_2CH_2CH_2$—, $CH_3ClCHCH_2CH_2$—, $CH_3CH_2ClCHCH_2$—, $CH_3CH_2CH_2ClCH$—, $ClCH_2CH_2CH(CH_3)$—, $ClCH_2(CH_3)_2C$—, $ClCH_2CH_2CH_2CH_2CH_2$—, $CH_3CH{=}CHCH_2$—, $ClCH{=}CHCH_2$—, $Cl_2C{=}CHCH_2$—, $ClCH{=}CClCH_2$—, $CH_3C{\equiv}CCH_2$—, $ClC{\equiv}CCH_2$— or the following substituents:

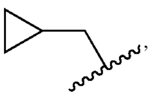, 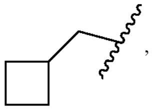, 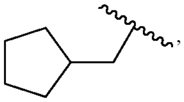, 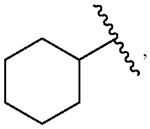, 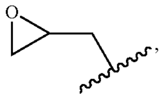, 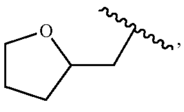, 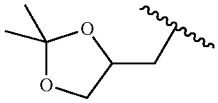 or 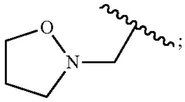;

or, an optical isomer of the compound shown in formula I when $R_3$ is selected from H and $R_4$ is not selected from H.

A further preferred compound in the present invention is: in the formula I:

W is selected from S;

$X_1$ is selected from F;

$X_2$ is selected from Cl;

$R_1$ is selected from methyl;

$R_2$ is selected from methyl;

$R_3$ is selected from H or methyl;

$R_4$ is selected from H or methyl;

$R_5$ is selected from $CH_3CH_2$—, $CH_3CH_2CH_2$—, $(CH_3)_2CH$—, $CH_3CH_2CH_2CH_2$—, $(CH_3)_2CHCH_2$—, $CH_3CH_2CH(CH_3)$—, $(CH_3)_3C$—, $CH_3CH_2CH_2CH_2CH_2$—, $(CH_3)_2CHCH_2CH_2$—, $(CH_3)_3CCH_2$—, $CH_3CH_2CH(CH_3)CH_2$—, $CH_3CH_2CH_2CH(CH_3)$—, $CH_3CH_2C(CH_3)_2$—, $ClCH_2CH_2$—, $ClCH_2CH_2CH_2$—, $CH_3ClCHCH_2$—, $CH_2Cl(CH_3)CH$—, $ClCH_2CH_2CH_2CH_2$—, $CH_3ClCHCH_2CH_2$—, $CH_3CH_2ClCHCH_2$—, $CH_3CH_2CH_2ClCH$—, $ClCH_2CH_2CH(CH_3)$—, $ClCH_2(CH_3)_2C$—, $ClCH_2CH_2CH_2CH_2CH_2$—, $CH_3CH{=}CHCH_2$—, $ClCH{=}CHCH_2$—, $Cl_2C{=}CHCH_2$—, $ClCH{=}CClCH_2$—, $CH_3C{\equiv}CCH_2$—, $ClC{\equiv}CCH_2$— or the following substituents:

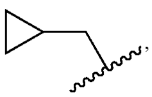, 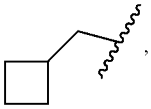, 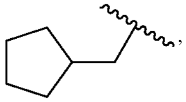, 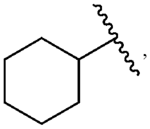, 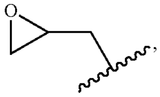, 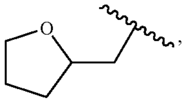, 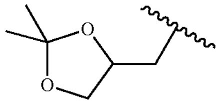 or 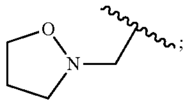;

or, an optical isomer of the compound shown in formula I is S configuration or S configuration content is greater than 60% when $R_3$ is selected from H and $R_4$ is selected from methyl.

In the definitions of the compounds of the formula I provided above, the terms used in the collection are defined as follows:

Halogen refers to fluorine, chlorine, bromine and iodine. Alkyl refers to linear or branched groups such as methyl, ethyl, n-propyl, isopropyl, n-butyl, isobutyl, sec-butyl, tert-butyl, n-pentyl, isopentyl and n-hexyl. Haloalkyl refers to the group whose alkyl is replaced by one or more halogen atoms, such as chloroethyl and trifluoromethyl. Cycloalkyl refers to groups in the form of cyclic chain, such as cyclopropyl, methylcyclopropyl, cyclopropylcyclopropyl, cyclobutyl, cyclopentyl and cyclohexyl. Alkenyl refers to linear or branched alkenyl, such as 1-propenyl, 2-propenyl, butenyl, pentenyl and hexenyl. When the substituent of the compound is alkenyl, the substituent also comprises Z type or E type configuration isomers formed when different atoms are connected on both sides of the carbon-carbon double bond. Alkynyl refers to linear or branched chain alkynyl, such as 1-propynyl, 2-propynyl, butynyl, pentynyl and hexynyl. Alkoxy refers to a group having an oxygen atom connected at the end of the alkyl, such as methoxy, ethoxy, n-propoxy, isopropoxy and tert-butoxy. Alkylsulfinyl refers to a group having a sulfur atom connected at the end of alkyl, such as methylthio, ethylthio, n-propylthio, isopropylthio and tert-butylthio. Alkylsulfinyl refers to a group having sulfinyl connected at the end of alkyl, such as methylsulfinyl, ethylsulfinyl, isopropylsulfinyl and tert-butylsulfinyl. Alkylsulfonyl refers to a group having sulfonyl connected at the end of alkyl, such as methanesulfonyl, ethylsulfonyl, isopropylsulfonyl and tert-butylsulfonyl. The 5-7-membered heterocycle containing 1-4 heteroatoms refers to a 5-7-membered heterocyclic compound containing 1-4 heteroatoms without aromatic characteristics, such as ethylene oxide, tetrahydrofuran, imidazolinone and caprolactam. The 5-7-membered aromatic heterocycle containing 1-4 heteroatoms refers to a 5-7-membered heterocyclic compound containing 1-4 heteroatoms having aromatic characteristics, such as furan, thiophene and pyridine.

The compound of the formula (I) in the present invention can be prepared by the following method. Unless otherwise stated in the reaction formula, the definitions of other groups are the same as above:

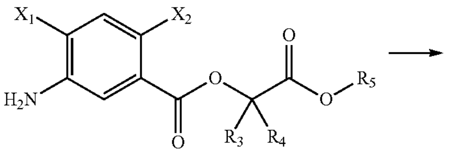

(II)

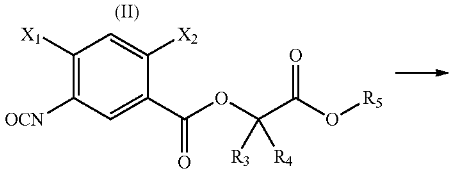

(III)

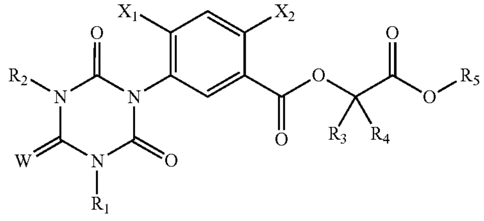

(I)

Intermediate aminobenzoate (II) reacts with a carbonylation reagent to form isocyanate (III), and isocyanate (III) reacts with 1,3-disubstituted urea or 1,3-disubstituted thiourea in an organic solvent at a temperature of −10° C. to the boiling point of the organic solvent for 0.5-48 hours to obtain the compound (I) of the formula. The organic solvent can be selected from chloroform, dichloromethane, carbon tetrachloride, hexane, benzene, toluene, ethyl acetate, DMF, THE or dioxane. The addition of alkaline substances, such as triethylamine, pyridine, sodium hydroxide, potassium hydroxide, sodium carbonate, potassium carbonate or sodium bicarbonate, is beneficial to the reaction.

The carbonylation reagent is selected from triphosgene, carbonyldiimidazole (DCI), phosgene, diphosgene and chloroformate.

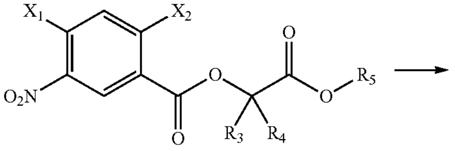

(IV)

-continued

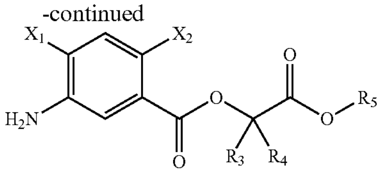

(II)

Intermediate nitrobenzoate (IV) reacts with an appropriate reducing agent at a temperature from −10° C. to the boiling point of the solvent for 0.5-48 hours to obtain intermediate aminobenzoate (II). The solvent can be selected from alcohols such as methanol, ethanol and isopropanol, ethers such as diethyl ether, tetrahydrofuran and dioxane, and esters such as ethyl acetate and methyl acetate.

The reducing agent is selected from hydrogen, transition metal in catalytic amount or transition metal compounds in catalytic amount; wherein the transition metal can be especially selected from Group VIII compounds, preferably Ni, Pd and Pt (directly used or supported by media such as activated carbon, aluminum oxide and silica); and hydrogen can be provided by hydrogen storage cylinders, or generated in situ by active metal (such as reduced iron powder, reduced zinc powder and stannous chloride) under acidic conditions (such as hydrochloric acid and sulfuric acid) and participates in the reduction reaction.

An appropriate reducing agent also comprises metal hydride, semimetal hydride and derivatives thereof, such as lithium aluminum hydride, diisobutylaluminum hydride, sodium borohydride and borane.

Intermediate IV can be prepared by the following three routes:

Route I:

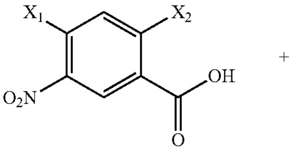

(V)

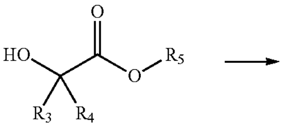

(VI)

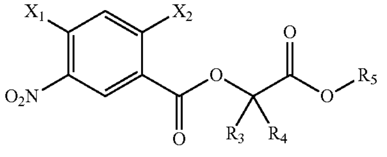

(IV)

Intermediate nitrobenzoic acid (V, available in the market) and substituted hydroxycarboxylate (VI, available in the market) are dissolved in an appropriate solvent to react at a temperature from −10° C. to the boiling point of the solvent for 0.5-48 hours, to prepare intermediate nitrobenzoate (IV) under the action of a dehydrating agent. The solvent can be selected from chloroform, dichloromethane, carbon tetrachloride, hexane, benzene, toluene, ethyl acetate, DMF, THE or dioxane. The dehydrating agent can be selected from dicyclohexylcarbodiimide (DCC), diisopropylcarbodiimide (DIC) and 1-(3-dimethylaminopropyl)-3-ethylcarbodiimide hydrochloride (EDC·HCl). The addition of alkaline substances, such as triethylamine, pyridine and 4-dimethylaminopyridine (DMAP), is beneficial to the reaction.

Route II:

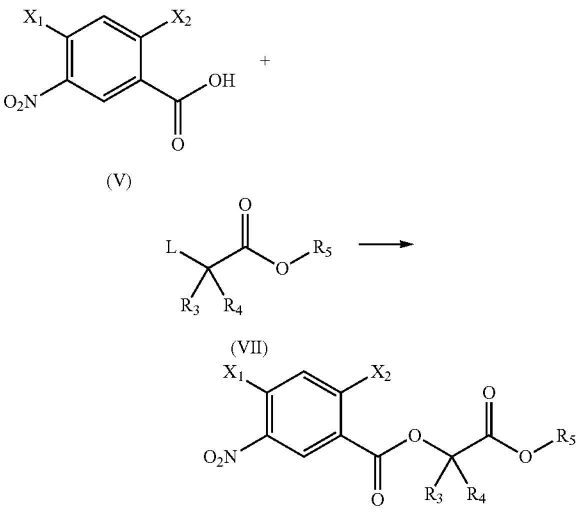

(V) (VII) (IV)

Intermediate nitrobenzoate (IV) can also be prepared by the reaction between intermediate nitrobenzoic acid (V) and corresponding substituted carboxylate (VII, available in the market) with an easily leaving group in an appropriate solvent for 0.5-48 hours at a temperature of −10° C. to the boiling point of the solvent. The solvent can be selected from chloroform, dichloromethane, carbon tetrachloride, hexane, benzene, toluene, ethyl acetate, DMF, THE or dioxane. The addition of alkaline substances, such as triethylamine, pyridine, sodium hydroxide, potassium hydroxide, sodium carbonate, potassium carbonate or sodium bicarbonate, is beneficial to the reaction.

In the substituted carboxylate (VII), L is a leaving group, such as chlorine, bromine, iodine, methylsulfonate and p-toluenesulfonate.

Route III:

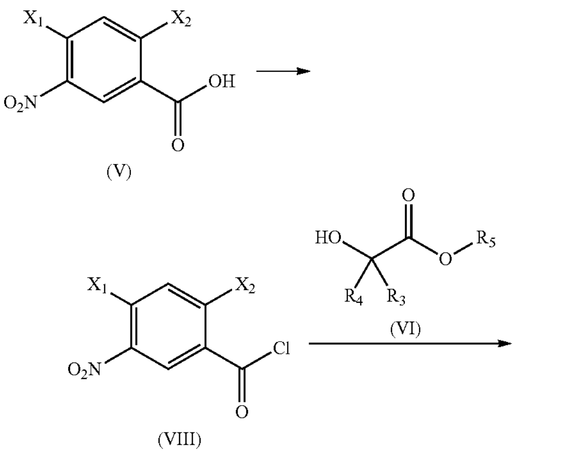

(V) (VI) (VIII)

-continued

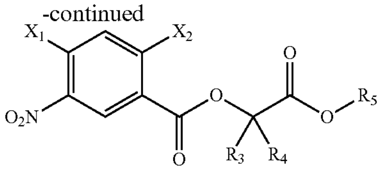

(IV)

Intermediate nitrobenzoic acid ester (IV) can also be prepared by the reaction between intermediate nitrobenzoic acid (V) and oxalyl chloride, thionyl chloride, phosphorus trichloride or phosphorus pentachloride in an appropriate solvent at a temperature of −10° C. to the boiling point of the solvent for 0.5-48 hours to obtain acid chloride (VIII) and an alcoholysis reaction between acid chloride (VIII) and substituted hydroxycarboxylate (VI). The appropriate solvent for the preparation of acid chloride is selected from dichloromethane, chloroform, carbon tetrachloride, hexane, benzene, toluene, ethyl acetate, acetonitrile, THF, dioxane or dimethyl sulfoxide. The appropriate solvent for the alcoholysis reaction is selected from chloroform, dichloromethane, carbon tetrachloride, hexane, benzene, toluene, ethyl acetate, DMF, THF or dioxane. Addition of the appropriate alkaline substances is beneficial for the reaction, and an appropriate base is selected from organic bases such as DMF, triethylamine, N,N-dimethylaniline or pyridine.

The compound of the formula (I) in the present invention can be prepared by the following method. Unless otherwise stated in the reaction formula, the definitions of other groups are the same as above:

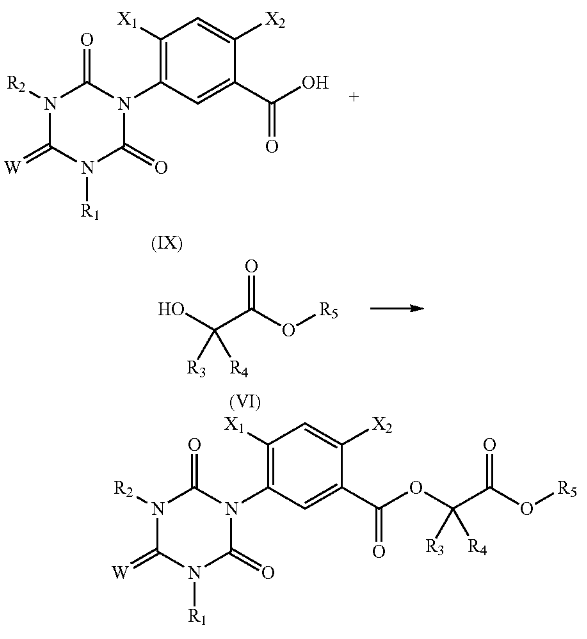

(IX) (VI) (I)

Intermediate triazine benzoic acid (IX) and substituted hydroxycarboxylate (VI, available in the market) are dissolved in an appropriate solvent and react at a temperature of −10° C. to the boiling point of the solvent for 0.5-48 hours, to prepare the compound (I) of the formula under the action of the dehydrating agent. The solvent can be selected from chloroform, dichloromethane, carbon tetrachloride, hexane, benzene, toluene, ethyl acetate, DMF, THE or dioxane. The dehydrating agent can be selected from dicyclohexylcarbodiimide (DCC), diisopropylcarbodiimide (DIC) and 1-(3-dimethylaminopropyl)-3-ethylcarbodiimide hydrochloride (EDC·HCl). The addition of alkaline substances, such as triethylamine, pyridine and 4-dimethylaminopyridine (DMAP), is beneficial to the reaction.

The compound of the formula (I) in the present invention can be prepared by the following method. Unless otherwise stated in the reaction formula, the definitions of other groups are the same as above:

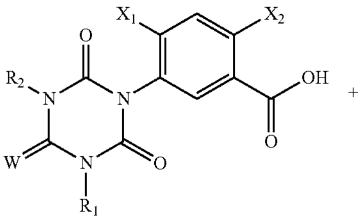

(IX)

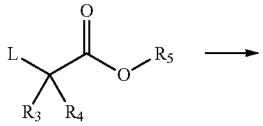

(VII)

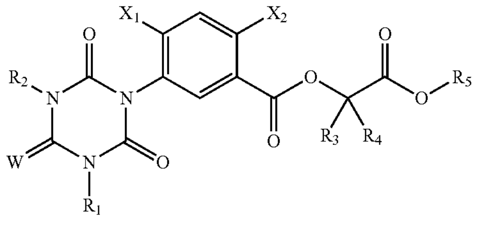

(I)

Intermediate triazine benzoic acid (IX) and corresponding substituted carboxylate (VII, available in the market) with an easily leaving group react in an appropriate solvent at a temperature of −10° C. to the boiling point of the solvent for 0.5-48 hours to prepare the compound (I) of the formula. The solvent can be selected from chloroform, dichloromethane, carbon tetrachloride, hexane, benzene, toluene, ethyl acetate, DMF, THE or dioxane. The addition of alkaline substances, such as triethylamine, pyridine, sodium hydroxide, potassium hydroxide, sodium carbonate, potassium carbonate or sodium bicarbonate, is beneficial to the reaction.

In the substituted carboxylate (VII), L is a leaving group, such as chlorine, bromine, iodine, methylsulfonate and p-toluenesulfonate.

The compound of the formula (I) in the present invention can be prepared by the following method. Unless otherwise stated in the reaction formula, the definitions of other groups are the same as above:

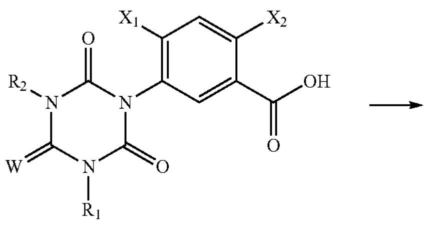

(IX)

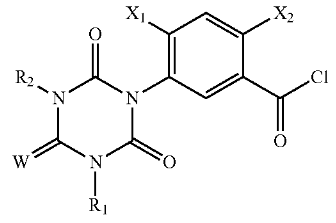

(X)

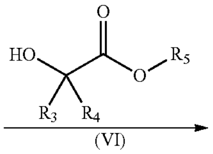

(VI)

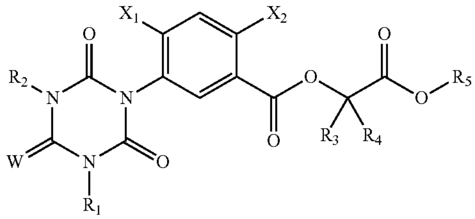

(I)

Intermediate triazine benzoic acid (IX) reacts with oxalyl chloride, thionyl chloride, phosphorus trichloride or phosphorus pentachloride in an appropriate solvent at a temperature of −10° C. to the boiling point of the solvent for 0.5-48 hours to obtain acid chloride (X), and then acid chloride (X) generates an alcoholysis reaction with substituted hydroxycarboxylate (VI) to obtain compound (I) of the formula. The appropriate solvent for the preparation of acid chloride is selected from dichloromethane, chloroform, carbon tetrachloride, hexane, benzene, toluene, ethyl acetate, acetonitrile, THF, dioxane or dimethyl sulfoxide. The appropriate solvent for the alcoholysis reaction is selected from chloroform, dichloromethane, carbon tetrachloride, hexane, benzene, toluene, ethyl acetate, DMF, THE or dioxane. Addition of the appropriate alkaline substances is beneficial for the reaction, and an appropriate base is selected from organic bases such as DMF, triethylamine, N,N-dimethylaniline or pyridine.

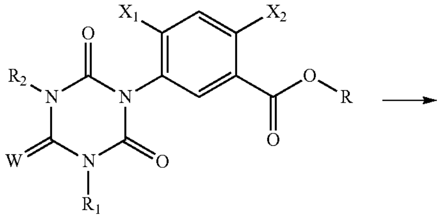

(XI)

-continued

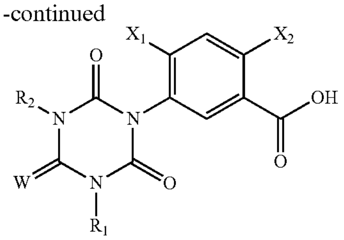

(IX)

Intermediate triazine benzoic acid (IX) can be prepared by dissolving intermediate triazine benzoate (XI, R is methyl, ethyl, n-propyl, isopropyl or benzyl) in an appropriate solvent at temperature of −10° C. to the boiling point of the solvent for 0.5-48 hours under the action of acidic aqueous solution (such as sulfuric acid, hydrochloric acid and phosphoric acid), alkaline aqueous solutions (such as sodium hydroxide and potassium hydroxide) or Lewis acid (such as boron tribromide, boron trichloride, boron trifluoride and aluminum trichloride), organosilicon reagents (such as trimethyl iodide silane and trimethyl chlorosilane). The solvent can be selected from acetonitrile, chloroform, dichloromethane, carbon tetrachloride, hexane, benzene, toluene, ethyl acetate, DMF, THE or dioxane.

In organic molecules, due to the difference in chiral structures, the binding degrees of the whole molecule with a target will be greatly different. An appropriate spatial structure of bioactive molecules plays an important role in the exertion of drug efficacy. The suitability of the spatial structure of bioactive molecules is unpredictable and can be known through a large amount of creative labor.

In the compound of the present invention, a carboxylate group is further introduced. After the group is introduced, the whole molecule will be greatly different in terms of electronegativity and spatial structure, so that the transportability of the whole molecule in organisms such as plants is quite different. Appropriate transportation performance of the bioactive molecules plays an important role in the exertion of drug efficacy. The suitability of the transportation performance of the bioactive molecules is unpredictable and can be known through a large amount of creative labor.

Compared with the known benzoate compounds, the compound containing two carboxylate structures in the present invention has unexpectedly high herbicidal activity can effectively control dicotyledonous weeds when used after emergence at a lower dose, and especially has surprisingly satisfying effect for broadleaf weeds.

Compared with the carboxylate compound in R configuration, the photoactive carboxylate compound which is mainly in S configuration in the present invention has unexpectedly high herbicidal activity, and can effectively control weeds under a certain dose.

Therefore, the technical solution of the present invention further comprises use of the compound of the formula (I) for controlling the weeds.

The present invention further comprises a herbicidal composition using the compound of the formula (I) as an active ingredient. The weight percentage of the active ingredient in the herbicidal composition is 5-90%. The herbicidal composition further comprises an agriculturally acceptable carrier.

The herbicidal composition of the present invention can be applied in the forms of various formulations. The compound of the present invention is generally dissolved or dispersed in the carrier and prepared into the formulation for easier dispersion when used as a herbicide. For example, the chemical formulations can be prepared into wettable powder or missible oil. Therefore, in the compositions, at least one liquid or solid carrier is added, and generally a suitable surfactant needs to be added.

Another implementing solution of the present invention is a method for controlling weeds. The method comprises applying an effective dose of the herbicidal composition of the present invention to the weed or a weed growing place or a surface of a growth medium thereof. The more appropriate effective dose which is often selected is 1 gram to 500 grams per hectare, and preferably, the effective dose is 2 grams to 250 grams per hectare. For some applications, one or more other herbicides can be added to the herbicidal composition of the present invention, thereby generating additional advantages and effects.

The compound of the present invention can be used alone or in combination with other known pesticides, bactericides, plant growth regulators or fertilizers.

It should be clear that various changes and modifications can be made within the scope defined by the claims of the present invention.

DETAILED DESCRIPTION

The following synthesis embodiments and biometric test results can be used to further illustrate the present invention, but are not intended to limit the present invention.

SYNTHESIS EMBODIMENTS

Embodiment 1: Synthesis of Compound 1 2-chloro-4-fluoro-5-(3, 5-dimethyl-2,4,6-trioxo-1,3,5-triazine-1-yl)benzoic acid (1-ethoxycarbonyl) ethyl ester

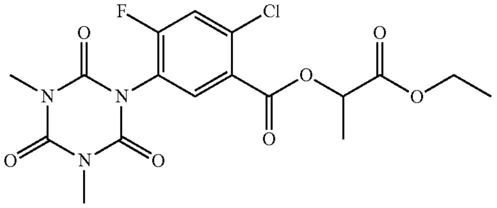 [SMILES: CCOC(=O)C(C)OC(=O)c1cc(-n2c(=O)n(C)c(=O)n(C)c2=O)c(F)cc1Cl]

Step a) Synthesis of Intermediate 2-chloro-4-fluoro-5-isopropyl nitrobenzoate

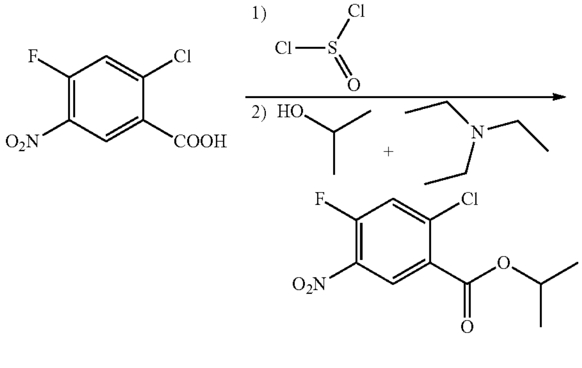

2-chloro-4-fluoro-5-nitrobenzoic acid (13.20 g, 60 mmol), toluene (60 mL) and thionyl chloride (7.5 mL, 103 mmol) were added into a 250 mL reaction flask, and refluxed to react for 3 h. The reaction system is changed from a suspension to a clear solution. A solvent and excess thionyl chloride were evaporated under reduced pressure, and the residue was diluted with 20 mL of dichloromethane for later use.

Dichloromethane (60 mL), isopropanol (4.00 g, 67 mmol) and triethylamine (9.0 mL, 65 mmol) were added to another 250 mL reaction flask in sequence, and the above prepared acyl chloride dichloromethane solution was added to the flask at room temperature; and after dropwise adding, the mixture was continuously stirred for 2 h at room temperature. The reaction solution was poured into 100 mL of water and extracted with 50 mL of dichloromethane; and a combined organic layer was washed with 50 mL of saturated salt water, dried with anhydrous magnesium sulphate and concentrated under reduced pressure to obtain 14.40 g of yellow liquid with a crude yield of 92%. The obtained 2-chloro-4-fluoro-5-isopropyl nitrobenzoate is directly used for synthesis in the next step without further purification.

Step b) Synthesis of Intermediate 5-amino-2-chloro-4-isopropyl fluorobenzoate

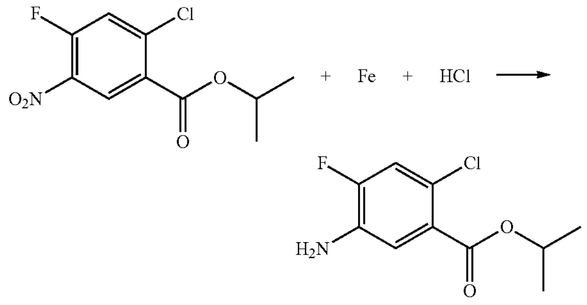

2-chloro-4-fluoro-5-isopropyl nitrobenzoate (14.40 g, 55 mmol) formed a solution with a mixed solvent formed by 30 mL of ethanol and 60 mL of tetrahydrofuran in the 250 mL reaction flask; reduced iron powder (11.00 g, 197 mmol) was added; concentrated hydrochloric acid (40 mL, about 480 mmol) was dropwise added to the mixture in an ice water bath; and after dropwise adding, the mixture was restored to room temperature to react for 1 h. the solvent was evaporated under reduced pressure; 100 mL of water was added to the residue; a combined organic layer was extracted (50 mL×3) with ethyl acetate, washed with 50 mL of saturated salt water, dried with anhydrous magnesium sulphate and concentrated under reduced pressure to obtain 13.00 g of brown liquid; and the brown liquid was cooled to obtain dark brown solid with a crude yield of 102%. The obtained 5-amino-2-chloro-4-isopropyl fluorobenzoate is directly used for synthesis in the next step without further purification. For purification, recrystallization can be conducted with ethanol to obtain yellow solid.

Step c) Synthesis of Intermediate 2-chloro-4-fluoro-5-(3, 5-dimethyl-2,4,6-trioxo-1,3,5-triazine-1-yl) isopropyl benzoate

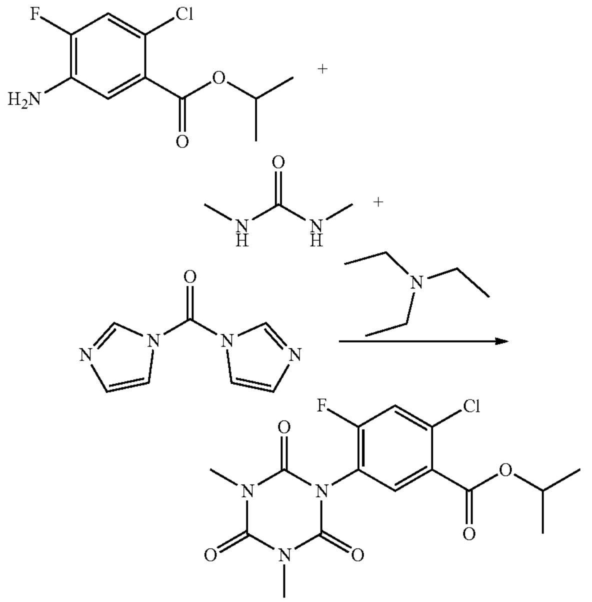

50 mL of ethyl acetate was added into a 250 mL reaction flask; then, 5-amino-2-chloro-4-isopropyl fluorobenzoate (13.00 g, 56 mmol), triethylamine (9.0 mL, 65 mmol) and carbonyldiimidazole (DCI, 22.50 g, 140 mmol) were added successively to form a solution; and the solution was heated to 50° C. to react for 30 min. 1,3-dimethylurea (5.90 g, 67 mmol) was added into the solution, and the temperature was raised to reflux to react for 2 h. After the reaction was completed, 100 mL of ethyl acetate was added thereto, washed with saturated salt water (50 mL×2), dried with anhydrous magnesium sulfate, and concentrated under reduced pressure to obtain brown viscous liquid. Column chromatography separation ($SiO_2$, EtOAc:P.E.=1:9, then 1:4) was conducted to obtain 15.35 g of yellow liquid with a yield of 73%.

Step d) Synthesis of Intermediate 2-chloro-4-fluoro-5-(3,5-dimethyl-2,4,6-trioxo-1,3,5-triazine-1-yl)benzoic acid

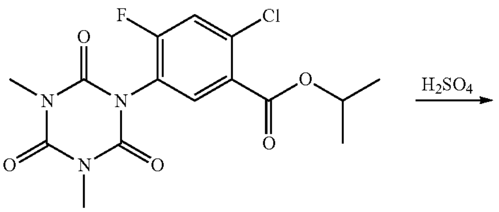

-continued

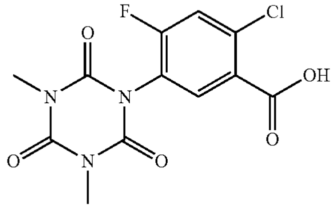

2-chloro-4-fluoro-5-(3, 5-dimethyl-2,4,6-trioxo-1,3,5-triazine-1-yl)isopropyl benzoate (4.46 g, 12 mmol) and concentrated sulfuric acid (12.0 mL, 220 mmol) were added into a 100 mL reaction flask to form a solution; and the solution was heated to 80° C. to react for 4 h. After the reaction was completed, the reaction solution was poured into 60 mL of ice-water mixture, and the precipitated gray solid was obtained by filtration, rinsed twice with 30 mL of water, and air-dried to obtain 3.90 g of intermediate 2-chloro-4-fluoro-5-(3,5-dimethyl-2,4,6-trioxo-1,3,5-triazine-1-yl)benzoic acid with a yield of 98%.

Step e) Synthesis of Compound 1 2-chloro-4-fluoro-5-(3, 5-dimethyl-2,4,6-trioxo-1,3,5-triazine-1-yl)benzoic acid (1-ethoxycarbonyl) ethyl ester

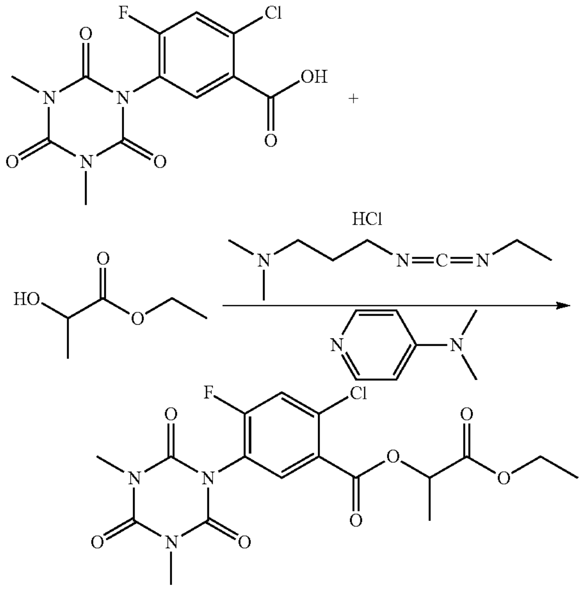

2-chloro-4-fluoro-5-(3,5-dimethyl-2,4,6-trioxo-1,3,5-triazine-1-yl)benzoic acid (0.50 g, 1.5 mmol), ethyl lactate (0.20 g, 1.7 mmol) and 4-(N,N-dimethylamino)pyridine (DMAP, 0.05 g, 0.4 mmol) were mixed and dissolved in 50 mL of dichloromethane in a 100 mL reaction flask to form grey-white suspension. 1-(3-dimethylaminopropyl)-3-ethylcarbodiimide hydrochloride (EDC·HCl, 0.60 g, 3.1 mmol) was added in batches into the reaction flask at room temperature, and the reaction system was changed from the suspension to a clear solution. After the material was added, the material was stirred at room temperature for 2 h. The reaction solution was poured into 50 mL of water, and extracted with dichloromethane (15 mL×2); the combined organic layer was washed with 15 mL of saturated salt water, dried with anhydrous magnesium sulfate, and concentrated under reduced pressure to obtain brown viscous liquid. Column chromatography separation ($SiO_2$, EtOAc:P.E.=1:4) was conducted to obtain 0.27 g of compound 1, 2-chloro-4-fluoro-5-(3, 5-dimethyl-2,4,6-trioxo-1,3,5-triazine-1-yl) benzoic acid (1-ethoxycarbonyl) ethyl ester, i.e., yellow liquid with a yield of 41%.

Embodiment 2: Synthesis of Compound 33 2-chloro-4-fluoro-5-(3,5-dimethyl-2,4,6-trioxo-1,3,5-triazine-1-yl)benzoic acid (1-(2-butynyloxycarbonyl))ethyl ester

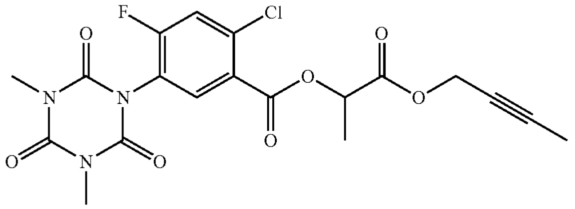 [SMILES: CC#CCOC(=O)C(C)OC(=O)c1cc(-n2c(=O)n(C)c(=O)n(C)c2=O)c(F)cc1Cl]

Step a) Synthesis of Intermediate 2-bromopropanoate (2-butyn-1-ol)ester

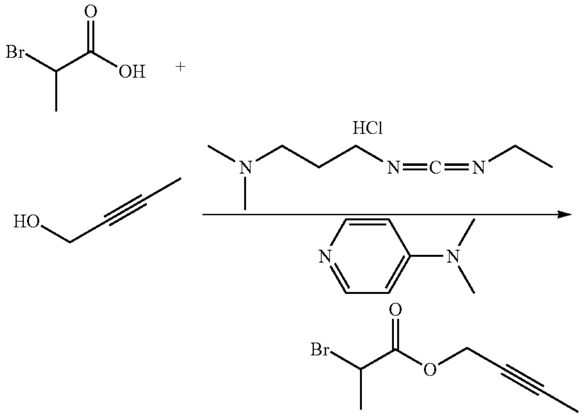

In a 250 mL reaction flask, 2-bromopropionic acid 3.82 g, 25.0 mmol), 2-butyn-1-ol (1.80 g, 25.7 mmol), and 4-(N,N-dimethylamino)pyridine (DMAP, 0.60 g, 5.0 mmol) were mixed in 50 mL of dichloromethane to form a solution. 1-(3-dimethylaminopropyl)-3-ethylcarbodiimide hydrochloride (EDC·HCl, 9.60 g, 50.0 mmol) was added in batches into the reaction flask at room temperature. After the material was added, the material was stirred at room temperature for 2 h. The reaction solution was poured into 50 mL of water, and extracted with dichloromethane (25 mL×2); the combined organic layer was washed with 25 mL of saturated salt water, dried with anhydrous magnesium sulfate, and concentrated under reduced pressure to obtain 3.85 g of yellowish liquid with a yield of 75%. The liquid is directly used for reaction in the next step without further purification.

Step b) Synthesis of Compound 33 2-chloro-4-fluoro-5-(3,5-dimethyl-2,4,6-trioxo-1,3,5-triazine-1-yl)benzoic acid (1-(2-butynyloxycarbonyl))ethyl ester

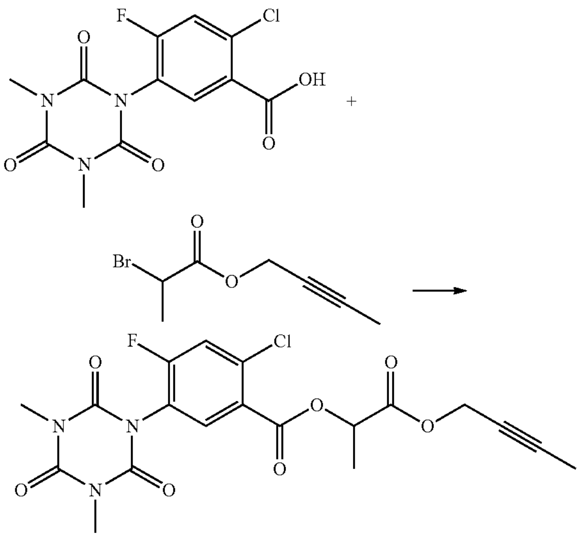

2-chloro-4-fluoro-5-(3,5-dimethyl-2,4,6-trioxo-1,3,5-triazine-1-yl)benzoic acid (0.50 g, 1.5 mmol) and potassium carbonate (0.22 g, 1.6 mmol) were mixed and dissolved in 7.5 mL of N,N-dimethylformamide (DMF) in a 100 mL reaction flask to form grey-white suspension; and 2-bromopropanoate (2-butyn-1-ol)ester (0.33 g, 1.6 mmol) was added into the suspension at room temperature. After the material was added, the material was stirred at room temperature for 2 h. The reaction solution was poured into 30 mL of water, and extracted with ethyl acetate (15 mL×3); the combined organic layer was washed with 15 mL of saturated salt water, dried with anhydrous magnesium sulfate, and concentrated under reduced pressure to obtain yellow viscous liquid. Column chromatography separation ($SiO_2$, EtOAc:P.E.=1:4) was conducted to obtain 0.45 g of compound 33, 2-chloro-4-fluoro-5-(3,5-dimethyl-2,4,6-trioxo-1,3,5-triazine-1-yl)benzoic acid (1-(2-butynyloxycarbonyl)) ethyl ester, i.e., yellow liquid with a yield of 66%.

Embodiment 3: Synthesis of Compound 42 2-chloro-4-fluoro-5-(3,5-dimethyl-2,4,6-trioxo-1,3,5-triazine-1-yl)benzoic acid (2-methyl-1-ethoxycarbonyl)propyl ester

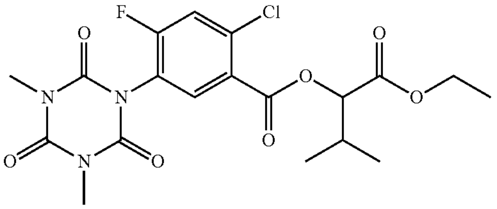

-continued

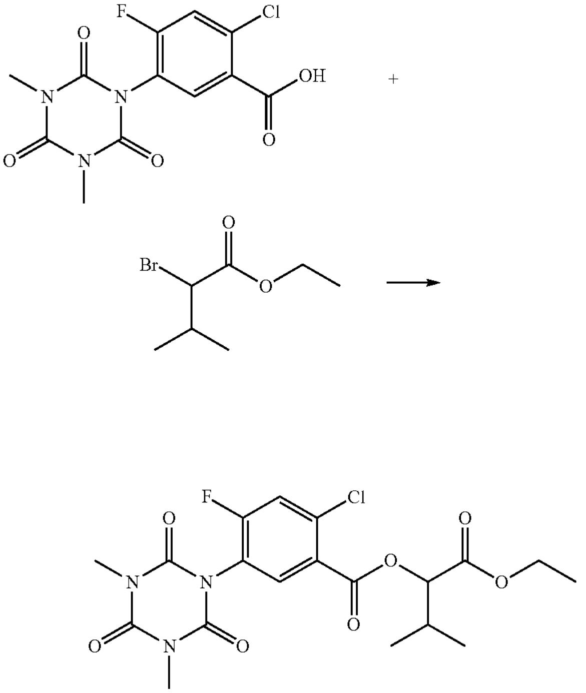

2-chloro-4-fluoro-5-(3,5-dimethyl-2,4,6-trioxo-1,3,5-triazine-1-yl)benzoic acid (0.66 g, 2.0 mmol) and potassium carbonate (0.29 g, 2.1 mmol) were mixed and dissolved in 10 mL of N,N-dimethylformamide (DMF) in a 100 mL reaction flask to form grey-white suspension; and 2-bromo-3-methylbutyric acid ethyl ester (0.42 g, 2.0 mmol, available in the market) was added into the suspension at room temperature. After the material was added, the material was stirred at room temperature for 2 h. The reaction solution was poured into 50 mL of water, and extracted with ethyl acetate (20 mL×3); the combined organic layer was washed with 25 mL of saturated salt water, dried with anhydrous magnesium sulfate, and concentrated under reduced pressure to obtain yellow viscous liquid. Column chromatography separation ($SiO_2$, EtOAc:P.E.=1:4) was conducted to obtain 0.37 g of compound 42, 2-chloro-4-fluoro-5-(3,5-dimethyl-2,4,6-trioxo-1,3,5-triazine-1-yl)benzoic acid (2-methyl-1-ethoxycarbonyl)propyl ester, i.e., orange liquid with a yield of 40%.

Embodiment 4: Synthesis of Compound 154 2-chloro-5-(3,5-dimethyl-2,6-dioxo-4-thio-1,3,5-triazine-1-yl)benzoic acid (1-(3,3-dichloroallyloxycarbonyl))ethyl ester

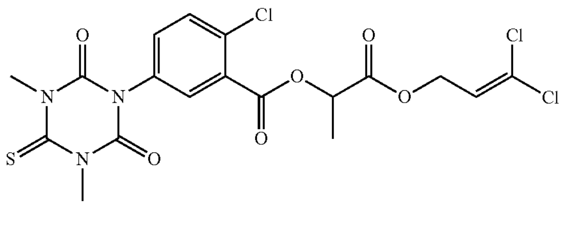 [SMILES: CC(OC(=O)c1cc(-n2c(=O)n(C)c(=S)n(C)c2=O)ccc1Cl)C(=O)OCC=C(Cl)Cl]

Step a) Synthesis of Intermediate benzyl 2-chloro-5-nitrobenzoate

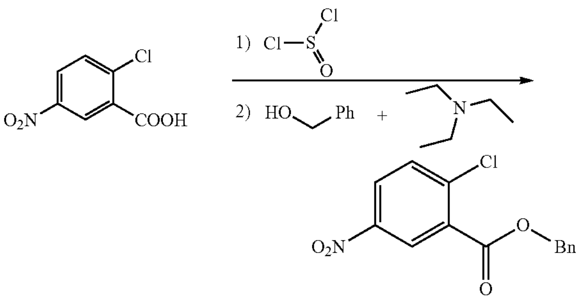

2-chloro-5-nitrobenzoic acid (20.16 g, 100 mmol), toluene (100 mL) and thionyl chloride (12.5 mL, 170 mmol) were added into a 250 mL reaction flask, and refluxed to react for 3 h. The reaction system is changed from a suspension to a clear solution. A solvent and excess dichlorosulfoxide were evaporated under reduced pressure, and the residue was diluted with 50 mL of dichloromethane for later use.

Dichloromethane (100 mL), benzyl alcohol (12.50 g, 116 mmol) and triethylamine (15.0 mL, 108 mmol) were added into another 250 mL reaction flask successively, and the above prepared acyl chloride dichloromethane solution was added to the flask at room temperature; and after dropwise adding, the mixture was continuously stirred for 2 h at room temperature. The reaction solution was poured into 100 mL of water and extracted with 50 mL of dichloromethane; and a combined organic layer was washed with 50 mL of saturated salt water, dried with anhydrous magnesium sulphate and concentrated under reduced pressure to obtain 30.00 g of yellow liquid with a crude yield of 103%. The obtained benzyl 2-chloro-5-nitrobenzoate is directly used for synthesis in the next step without further purification.

Step b) Synthesis of Intermediate benzyl 5-amino-2-chlorobenzoate

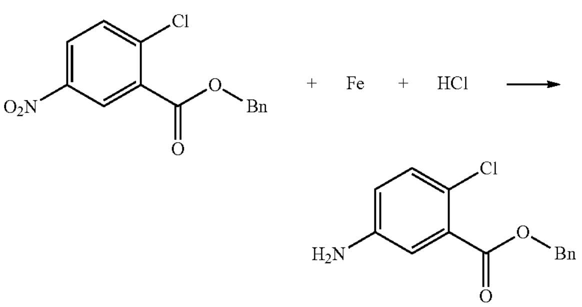

benzyl 2-chloro-5-nitrobenzoate (30.00 g, 100 mmol) prepared in the above step formed a solution with a mixed solvent formed by 50 mL of ethanol and 50 mL of tetrahydrofuran in the 250 mL reaction flask; reduced iron powder (19.50 g, 350 mmol) was added; concentrated hydrochloric acid (66 mL, about 800 mmol) was dropwise added to the mixture in an ice water bath; and after dropwise adding, the mixture was restored to room temperature to react for 1 h. The solvent was evaporated under reduced pressure; 100 mL of water was added to the residue; a combined organic layer was extracted (50 mL×3) with ethyl acetate, washed with 50 mL of saturated salt water, dried with anhydrous magnesium sulphate and concentrated under reduced pressure to obtain 25.80 g of yellow liquid; and the yellow liquid was cooled to obtain dark yellow solid with a crude yield of 99%. The obtained benzyl 5-amino-2-chlorobenzoate is directly used for synthesis in the next step without further purification. For purification, recrystallization can be conducted with ethanol to obtain yellowish solid.

Step c) Synthesis of Intermediate benzyl 2-chloro-5-(3,5-dimethyl-2,6-dioxo-4-thio-1,3,5-triazine-1-yl) benzoate

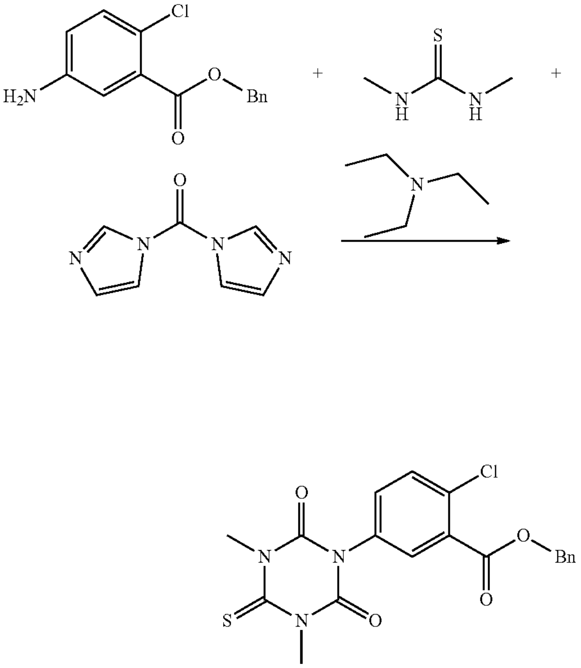

100 mL of ethyl acetate was added into a 250 mL reaction flask; then, benzyl 5-amino-2-chlorobenzoate (25.80 g, 99 mmol), triethylamine (15.0 mL, 108 mmol) and carbonyldiimidazole (DCI, 40.00 g, 247 mmol) were added successively to form a solution; and the solution was heated to 50° C. to react for 30 min. 1,3-dimethylthiourea (11.00 g, 106 mmol) was added into the solution, and the temperature was raised to reflux to react for 2 h. After the reaction was completed, 100 mL of ethyl acetate was added thereto, washed with saturated salt water (50 mL×2), dried with anhydrous magnesium sulfate, and concentrated under reduced pressure to obtain brown viscous liquid. Column chromatography separation ($SiO_2$, EtOAc:P.E.=1:9, then 1:4) was conducted to obtain 27.50 g of yellow liquid with a yield of 66%. The obtained benzyl 2-chloro-5-(3,5-dimethyl-2,6-dioxo-4-thio-1,3,5-triazine-1-yl)benzoate is directly used for synthesis in the next step without further purification. For purification, recrystallization can be conducted with ethyl acetate/ethanol mixed solvent to obtain white solid.

Step d) Synthesis of Intermediate 2-chloro-5-(3,5-dimethyl-2,6-dioxo-4-thio-1,3,5-triazine-1-yl)benzoic acid

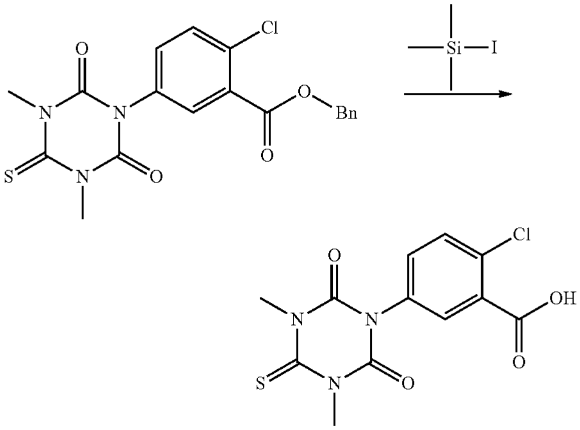

Benzyl 2-chloro-5-(3,5-dimethyl-2,6-dioxo-4-thio-1,3,5-triazine-1-yl)benzoate (18.68 g, 44.7 mmol) was dissolved in 50 mL of acetonitrile in a 250 mL reaction flask, and trimethylsilyl iodide (25.00 g, 125.0 mmol) was added at room temperature to the reaction flask; and the reaction was kept at room temperature overnight. After the reaction was completed, the reaction solution was poured into 60 mL of saturated aqueous sodium bicarbonate solution, and washed with methyl tert-butyl ether (50 mL×3); an aqueous layer was adjusted to pH=2-3 with concentrated hydrochloric acid, and then solid was precipitated, filtered and aired to obtain 13.60 g of intermediate 2-chloro-5-(3,5-dimethyl-2,6-dioxo-4-thio-1,3,5-triazine-1-yl)benzoic acid, i.e., yellowish solid, with a yield of 93%.

Step e) Synthesis of Compound 154 2-chloro-5-(3,5-dimethyl-2,6-dioxo-4-thio-1,3,5-triazine-1-yl)benzoic acid (1-(3,3-dichloroallyloxycarbonyl))ethyl ester

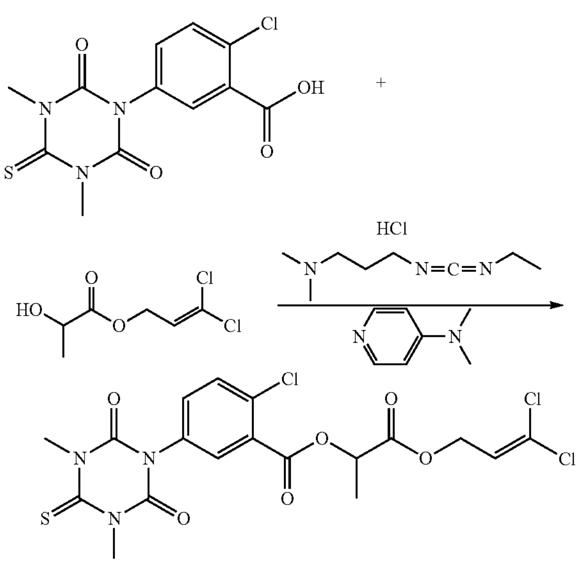

2-chloro-5-(3,5-dimethyl-2,6-dioxo-4-thio-1,3,5-triazine-1-yl)benzoic acid (0.50 g, 1.5 mmol), (3,3-dichloroallyl) lactate (0.35 g, 1.7 mmol) and 4-(N,N-dimethylamino)pyridine (DMAP, 0.05 g, 0.4 mmol) were mixed and dissolved in 15 mL of dichloromethane in a 100 mL reaction flask to form suspension. 1-(3-dimethylaminopropyl)-3-ethylcarbodiimide hydrochloride (EDC·HCl, 0.60 g, 3.1 mmol) was added in batches into the reaction flask at room temperature, and the reaction system was changed from the suspension to a clear solution. After the material was added, the material was stirred at room temperature for 2 h. The reaction solution was poured into 50 mL of water, and extracted with dichloromethane (15 mL×2); the combined organic layer was washed with 15 mL of saturated salt water, dried with anhydrous magnesium sulfate, and concentrated under reduced pressure to obtain yellow viscous liquid. Column chromatography separation ($SiO_2$, EtOAc:P.E.=1:6) was conducted to obtain 0.49 g of compound 154, 2-chloro-5-(3,5-dimethyl-2,6-dioxo-4-thio-1,3,5-triazine-1-yl)benzoic acid (1-(3,3-dichloroallyloxycarbonyl))ethyl ester, i.e., yellowish liquid with a yield of 63%.

Embodiment 5: Synthesis of Compound 166 2-chloro-5-(3,5-dimethyl-2,6-dioxo-4-thio-1,3,5-triazine-1-yl)benzoic acid (1-(solketal carbonyl)) ethyl ester

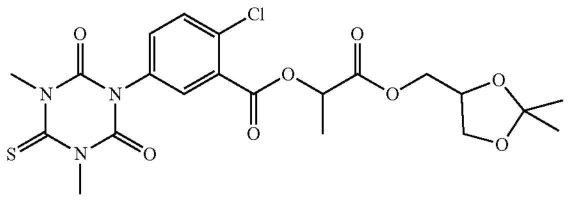

Step a) Synthesis of Intermediate 2-bromopropionic acid (solketal) ester

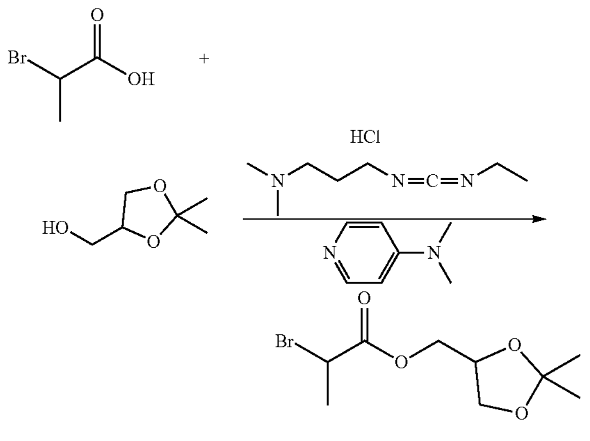

In a 250 mL reaction flask, 2-bromopropionic acid (7.65 g, 50.0 mmol), solketal (7.00 g, 53.0 mmol), and 4-(N,N-dimethylamino)pyridine (DMAP, 1.22 g, 10.0 mmol) were mixed in 50 mL of dichloromethane to form a solution. 1-(3-dimethylaminopropyl)-3-ethylcarbodiimide hydrochloride (EDC·HCl, 14.40 g, 75.0 mmol) was added in batches into the reaction flask at room temperature. After the material was added, the material was stirred at room temperature for 2 h. The reaction solution was poured into 50 mL of water, and extracted with dichloromethane (50 mL×2); the combined organic layer was washed with 25 mL of saturated salt water, dried with anhydrous magnesium sulfate, and concentrated under reduced pressure to obtain 10.10 g of yellowish liquid with a yield of 76%. The liquid is directly used for reaction in the next step without further purification.

Step b) Synthesis of Compound 166 2-chloro-5-(3,5-dimethyl-2,6-dioxo-4-thio-1,3,5-triazine-1-yl)benzoic acid (1-(solketal carbonyl))ethyl ester

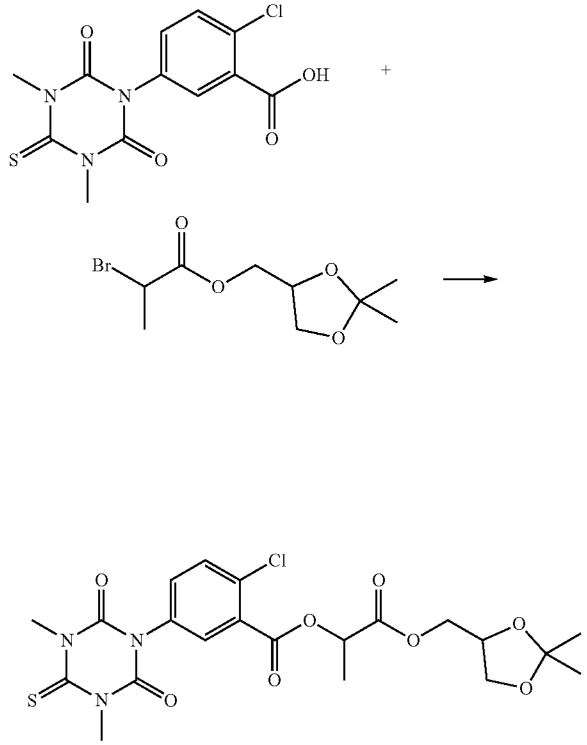

2-chloro-5-(3,5-dimethyl-2,6-dioxo-4-thio-1,3,5-triazine-1-yl)benzoic acid (0.33 g, 1.0 mmol) and potassium carbonate (0.18 g, 1.3 mmol) were mixed and dissolved in 5 mL of N,N-dimethylformamide (DMF) in a 100 mL reaction flask to form suspension; and 2-bromopropionic acid (solketal) ester (0.30 g, 1.1 mmol) was added into the suspension at room temperature. After the material was added, the material was stirred at room temperature for 2 h. The reaction solution was poured into 20 mL of water, and extracted with ethyl acetate (10 mL×3); the combined organic layer was washed with 10 mL of saturated salt water, dried with anhydrous magnesium sulfate, and concentrated under reduced pressure to obtain yellow viscous liquid. Column chromatography separation ($SiO_2$, EtOAc:P.E.=1:4) was conducted to obtain 0.40 g of compound 166, 2-chloro-5-(3,5-dimethyl-2,6-dioxo-4-thio-1,3,5-triazine-1-yl)benzoic acid (1-(solketal carbonyl))ethyl ester, i.e., colorless foam substance with a yield of 77%.

Embodiment 6: Synthesis of Compound 222 2-chloro-4-fluoro-5-(3,5-dimethyl-2,6-dioxo-4-thio-1,3,5-triazine-1-yl)benzoic acid (3-chloropropoxycarbonyl) methyl ester

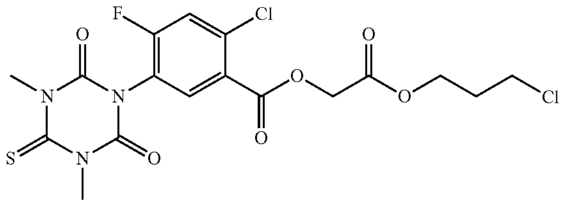 [SMILES: Cn1c(=S)n(C)c(=O)n(-c2cc(C(=O)OCC(=O)OCCCCl)c(Cl)cc2F)c1=O]

Step a) Synthesis of Intermediate benzyl 2-chloro-4-fluoro-5-nitrobenzoate

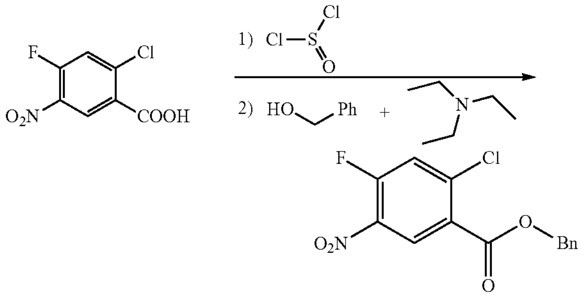

2-chloro-5-nitrobenzoic acid (8.80 g, 40 mmol), toluene (40 mL) and thionyl chloride (5.0 mL, 68 mmol) were added into a 250 mL reaction flask, and refluxed to react for 3 h. The reaction system is changed from a suspension to a clear solution. A solvent and excess thionyl chloride were evaporated under reduced pressure, and the residue was diluted with 20 mL of dichloromethane for later use.

Dichloromethane (40 mL), benzyl alcohol (5.00 g, 46 mmol) and triethylamine (6.0 mL, 43 mmol) were added to another 250 mL reaction flask in sequence, and the above prepared acyl chloride dichloromethane solution was added to the flask at room temperature; and after dropwise adding, the mixture was continuously stirred for 2 h at room temperature. The reaction solution was poured into 100 mL of water and extracted with 50 mL of dichloromethane; and a combined organic layer was washed with 50 mL of saturated salt water, dried with anhydrous magnesium sulphate and concentrated under reduced pressure to obtain 13.00 g of yellow liquid with a crude yield of 105%. The obtained benzyl 2-chloro-4-fluoro-5-nitrobenzoate is directly used for synthesis in the next step without further purification.

Step b) Synthesis of Intermediate benzyl 5-amino-2-chloro-4-fluorobenzoate

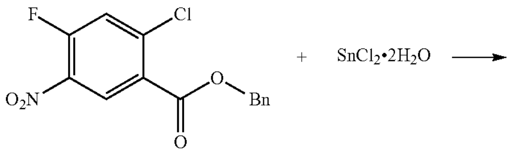

-continued

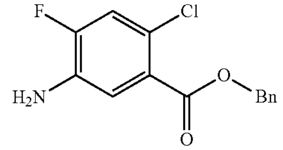

In a 250 mL reaction flask, benzyl 2-chloro-4-fluoro-5-nitrobenzoate (7.75 g, 25 mmol) prepared in the above step and 25 mL of ethyl acetate formed a solution, and stannous chloride dihydrate (22.00 g, 98 mmol) was added, heated and refluxed to react for 2 h. The reaction solution was poured into 100 mL of ice-water mixture, and the pH of the system was adjusted to 9-10 with dilute NaOH solution. The separated precipitate was filtered and rinsed with ethyl acetate for several times. A combined organic layer was washed with 25 mL of saturated salt water, dried with anhydrous magnesium sulphate and concentrated under reduced pressure to obtain 6.10 g of yellow liquid; and the yellow liquid was cooled to obtain brown solid with a crude yield of 87%. The obtained benzyl 5-amino-2-chloro-4-fluorobenzoate is directly used for synthesis in the next step without further purification. For purification, recrystallization can be conducted with ethanol to obtain yellow solid.

Step c) Synthesis of Intermediate 2-chloro-4-fluoro-5-(3,5-dimethyl-2,6-dioxo-4-thio-1,3,5-triazine-1-yl) benzyl benzoate

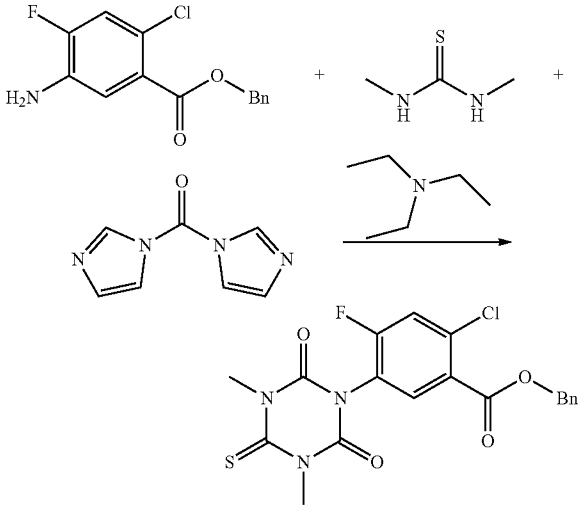

40 mL of ethyl acetate was added into a 250 mL reaction flask; then, benzyl 5-amino-2-chloro-4-fluorobenzoate (5.60 g, 20.0 mmol), triethylamine (3.5 mL, 25.0 mmol) and carbonyldiimidazole (DCI, 8.50 g, 52.4 mmol) were added successively to form a solution; and the solution was heated to 50° C. to react for 30 min. 1,3-dimethylthiourea (2.60 g, 25.0 mmol) was added into the solution, and the temperature was raised to reflux to react for 2 h. After the reaction was completed, 40 mL of ethyl acetate was added thereto, washed with saturated salt water (25 mL×2), dried with anhydrous magnesium sulfate, and concentrated under reduced pressure to obtain brown viscous liquid. Column chromatography separation ($SiO_2$, EtOAc:P.E.=1:9, then 1:4) was conducted to obtain 7.40 g of yellow liquid with a yield of 85%. The obtained 2-chloro-4-fluoro-5-(3,5-dimethyl-2,6-dioxo-4-thio-1,3,5-triazine-1-yl) benzyl benzoate is directly used for synthesis in the next step without further purification. For purification, recrystallization can be conducted with ethyl acetate/ethanol mixed solvent to obtain white solid.

Step d) Synthesis of Intermediate 2-chloro-4-fluoro-5-(3,5-dimethyl-2,6-dioxo-4-thio-1,3,5-triazine-1-yl) benzoic acid

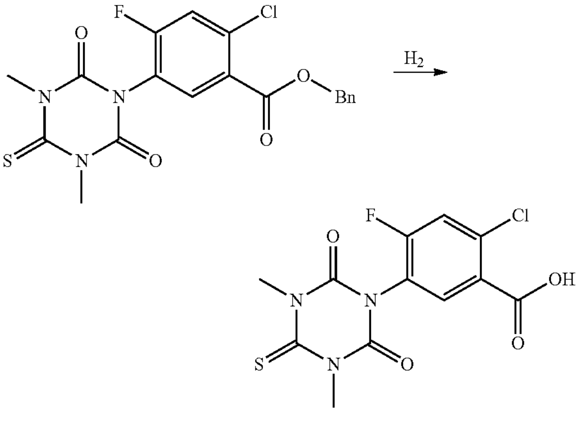

2-chloro-4-fluoro-5-(3,5-dimethyl-2,6-dioxo-4-thio-1,3,5-triazine-1-yl)benzyl benzoate (4.36 g, 10.0 mmol) was dissolved in 50 mL of methanol in a 100 mL reaction flask; 10% palladium-carbon catalyst (0.20 g, 0.2 mmol) was added to the reaction flask at room temperature; and a hydrogen flow was passed into the reaction flask at 50° C. to react for 4 h. After the reaction was completed, insolubles were removed by filtration; the reaction solution was poured into 60 mL of saturated aqueous sodium bicarbonate solution, and washed with methyl tert-butyl ether (50 mL×3); an aqueous layer was adjusted to pH=2-3 with concentrated hydrochloric acid, and then solid was precipitated, filtered and aired to obtain 2.88 g of intermediate 2-chloro-4-fluoro-5-(3,5-dimethyl-2,6-dioxo-4-thio-1,3,5-triazine-1-yl)benzoic acid, i.e., yellowish solid, with a yield of 83%.

Step e) Synthesis of Compound 222 2-chloro-4-fluoro-5-(3,5-dimethyl-2,6-dioxo-4-thio-1,3,5-triazine-1-yl)benzoic acid (3-chloropropoxycarbonyl) methyl ester

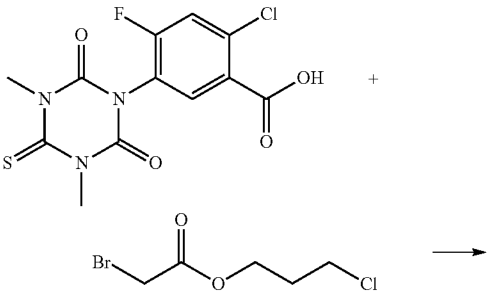

-continued

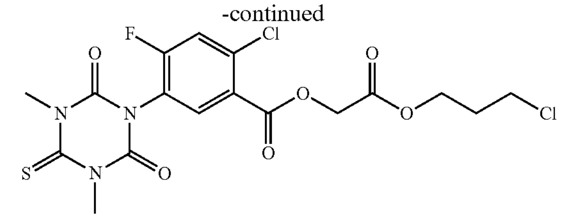

2-chloro-4-fluoro-5-(3,5-dimethyl-2,6-dioxo-4-thio-1,3,5-triazine-1-yl)benzoic acid (0.42 g, 1.2 mmol) and potassium carbonate (0.20 g, 1.4 mmol) were mixed and dissolved in 5 mL of N,N-dimethylformamide (DMF) in a 100 mL reaction flask to form suspension; and 2-bromoacetic acid (3-chloropropanol) ester (0.28 g, 1.3 mmol) was added to the suspension at room temperature. After the material was added, the material was stirred at room temperature for 2 h. The reaction solution was poured into 20 mL of water, and extracted with ethyl acetate (10 mL×3); the combined organic layer was washed with 10 mL of saturated salt water, dried with anhydrous magnesium sulfate, and concentrated under reduced pressure to obtain yellow viscous liquid. Column chromatography separation ($SiO_2$, EtOAc:P.E.=1:4) was conducted to obtain 0.55 g of compound 222, 2-chloro-4-fluoro-5-(3,5-dimethyl-2,6-dioxo-4-thio-1,3,5-triazine-1-yl)benzoic acid (3-chloropropoxycarbonyl) methyl ester, i.e., colorless foam substance with a yield of 94%.

Embodiment 7: Synthesis of Compound 241 2-chloro-4-fluoro-5-(3,5-dimethyl-2,6-dioxo-4-thio-1,3,5-triazine-1-yl)benzoic acid (cyclopropylmethoxycarbonyl) methyl ester

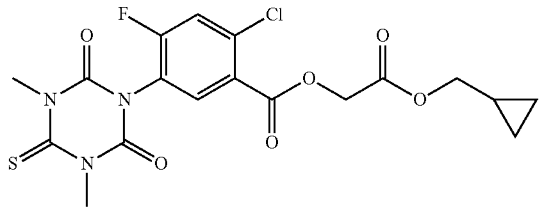 [SMILES: Cn1c(=S)n(C)c(=O)n(-c2cc(C(=O)OCC(=O)OCC3CC3)c(Cl)cc2F)c1=O]

Step a) Synthesis of Intermediate 2-bromoacetic acid (cyclopropanemethanol) ester

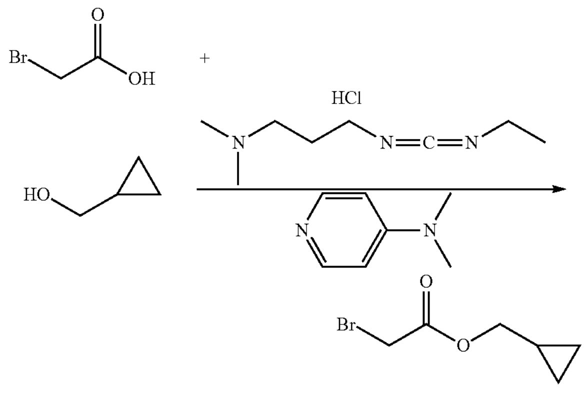

In a 250 mL reaction flask, 2-bromoacetic acid (4.16 g, 30.0 mmol), cyclopropylmethanol (2.38 g, 33.0 mmol) and 4-(N,N-dimethylamino)pyridine (DMAP, 0.75 g, 6.0 mmol) were mixed in 30 mL of dichloromethane to form a solution. 1-(3-dimethylaminopropyl)-3-ethylcarbodiimide hydrochloride (EDC·HCl, 8.60 g, 45.0 mmol) was added in batches into the reaction flask at room temperature. After the material was added, the material was stirred at room temperature for 2 h. The reaction solution was poured into 50 mL of water, and extracted with dichloromethane (30 mL×2); the combined organic layer was washed with 25 mL of saturated salt water, dried with anhydrous magnesium sulfate, and concentrated under reduced pressure to obtain 3.60 g of colorless liquid with a yield of 62%. The liquid is directly used for reaction in the next step without further purification.

Step b) Synthesis of Compound 241 2-chloro-4-fluoro-5-(3,5-dimethyl-2,6-dioxo-4-thio-1,3,5-triazine-1-yl)benzoic acid (cyclopropylmethoxycarbonyl) methyl ester

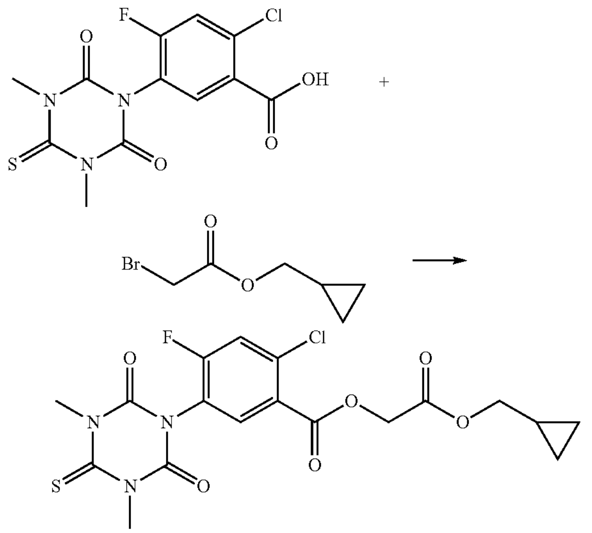

2-chloro-4-fluoro-5-(3,5-dimethyl-2,6-dioxo-4-thio-1,3,5-triazine-1-yl)benzoic acid (0.42 g, 1.2 mmol) and potassium carbonate (0.20 g, 1.4 mmol) were mixed and dissolved in 5 mL of N,N-dimethylformamide (DMF) in a 100 mL reaction flask to form suspension; and 2-bromoacetic acid (cyclopropanemethanol) ester (0.25 g, 1.3 mmol) was added to the suspension at room temperature. After the material was added, the material was stirred at room temperature for 2 h. The reaction solution was poured into 20 mL of water, and extracted with ethyl acetate (10 mL×3); the combined organic layer was washed with 10 mL of saturated saltwater, dried with anhydrous magnesium sulfate, and concentrated under reduced pressure to obtain yellow viscous liquid. Column chromatography separation ($SiO_2$, EtOAc:P.E.=1:4) was conducted to obtain 0.52 g of compound 241, 2-chloro-4-fluoro-5-(3, 5-dimethyl-2,6-dioxo-4-thio-1,3,5-triazine-1-yl)benzoic acid (cyclopropylmethoxycarbonyl) methyl ester, i.e., colorless foam substance with a yield of 93%.

Embodiment 8: Compound 248 2-chloro-4-fluoro-5-(3,5-dimethyl-2,6-dioxo-4-thio-1,3,5-triazine-1-yl) benzoic acid (1-ethoxycarbonyl)ethyl ester

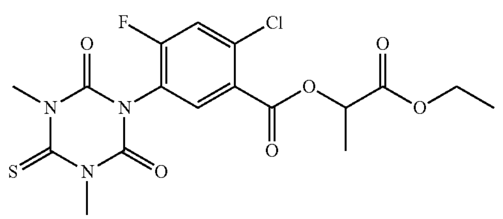 [SMILES: CCOC(=O)C(C)OC(=O)c1cc(-n2c(=O)n(C)c(=S)n(C)c2=O)c(F)cc1Cl]

Step a) Synthesis of Intermediate 2-chloro-4-fluoro-5-nitrobenzoic acid (1-ethoxycarbonyl)ethyl ester

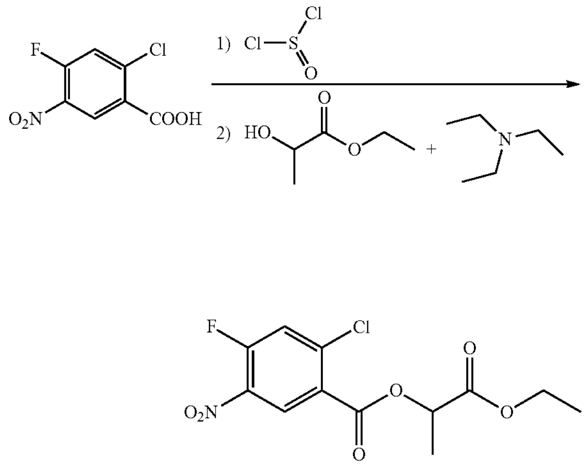

2-chloro-4-fluoro-5-nitrobenzoic acid (4.40 g, 20.0 mmol), toluene (20 mL) and thionyl chloride (3.0 mL, 41.1 mmol) were added into a 250 mL reaction flask, and refluxed to react for 3 h. The reaction system is changed from a suspension to a clear solution. A solvent and excess dichlorosulfoxide were evaporated under reduced pressure, and the residue was diluted with 10 mL of dichloromethane for later use.

Dichloromethane (20 mL), ethyl lactate (2.65 g, 22.4 mmol) and triethylamine (3.0 mL, 21.5 mmol) were added to another 250 mL reaction flask in sequence, and the above prepared acyl chloride dichloromethane solution was added to the flask at room temperature; and after dropwise adding, the mixture was continuously stirred for 2 h at room temperature. The reaction solution was poured into 50 mL of water and extracted with 50 mL of dichloromethane; and a combined organic layer was washed with 30 mL of saturated salt water, dried with anhydrous magnesium sulphate and concentrated under reduced pressure to obtain 6.16 g of yellow liquid with a crude yield of 96%. The obtained 2-chloro-4-fluoro-5-nitrobenzoate benzoate (1-ethoxycarbonyl) ethyl ester is directly used for synthesis in the next step without further purification.

Step b) Synthesis of Intermediate 5-amino-2-chloro-4-fluorobenzoic acid (1-ethoxycarbonyl)ethyl ester

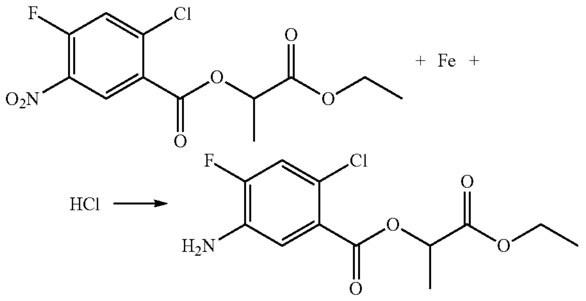

2-chloro-4-fluoro-5-nitrobenzoic acid (1-ethoxy-1-oxo-2-propanol) ester (6.16 g, 19.3 mmol) formed a solution with a mixed solvent formed by 20 mL of ethanol and 20 mL of tetrahydrofuran in the 250 mL reaction flask; reduced iron powder (4.00 g, 71.6 mmol) was added; concentrated hydrochloric acid (15 mL, about 180 mmol) was dropwise added to the mixture in an ice water bath; and after dropwise adding, the mixture was restored to room temperature to react for 1 h. The solvent was evaporated under reduced pressure; 50 mL of water was added to the residue; a combined organic layer was extracted (30 mL×3) with ethyl acetate, washed with 50 mL of saturated salt water, dried with anhydrous magnesium sulphate and concentrated under reduced pressure to obtain 4.00 g of yellow liquid with a crude yield of 72%. The obtained 5-amino-2-chloro-4-fluorobenzoic acid (1-ethoxycarbonyl)ethyl ester is directly used for synthesis in the next step without further purification.

Step c) Synthesis of Compound 248 2-chloro-4-fluoro-5-(3,5-dimethyl-2,6-dioxo-4-thio-1,3,5-triazine-1-yl) benzoic acid (1-ethoxycarbonyl)ethyl ester

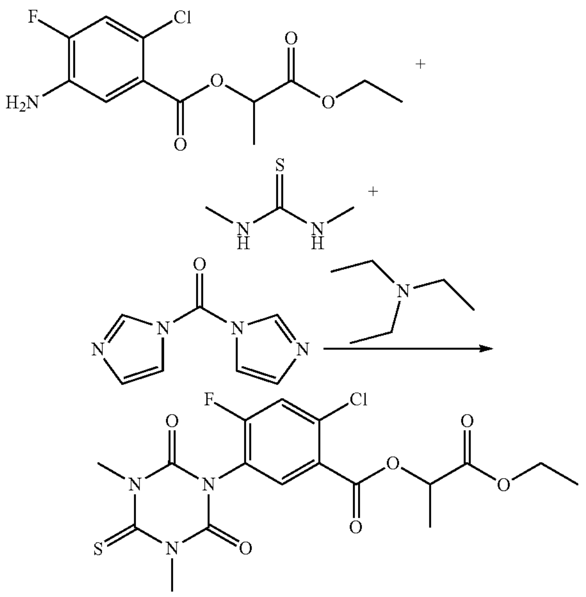

30 mL of ethyl acetate was added into a 250 mL reaction flask; then, 5-amino-2-chloro-4-fluorobenzoic acid (1-ethoxycarbonyl)ethyl ester (4.00 g, 13.8 mmol), triethylamine (2.5 mL, 18.0 mmol) and carbonyldiimidazole (DCI, 5.60 g, 34.5 mmol) were added successively to form a solution; and the solution was heated to 50° C. to react for 30 min. 1,3-dimethylthiourea (1.75 g, 16.8 mmol) was added into the solution, and the temperature was raised to reflux to react for 2 h. After the reaction was completed, 60 mL of ethyl acetate was added thereto, washed with saturated salt water (30 mL×2), dried with anhydrous magnesium sulfate, and concentrated under reduced pressure to obtain brown viscous liquid. Column chromatography separation ($SiO_2$, EtOAc:P.E.=1:9, then 1:4) was conducted to obtain 4.20 g of compound 248, 2-chloro-4-fluoro-5-(3,5-dimethyl-2,6-dioxo-4-thio-1,3,5-triazine-1-yl) benzoic acid (1-ethoxycarbonyl)ethyl ester, i.e., yellow liquid with a yield of 68%. The purity is above 95.3%. (HPLC: 17.574 min (50.8%); 19.589 min (44.5%); chromatographic conditions: DAICEL Chemical Industries, Ltd. ChiralPak AD-H type chiral column, isopropanol:n-hexane=10:90, flow rate 1.0 mL/s, and detection wavelength 254 nm.)

Embodiment 9: Synthesis of Compound 266 (R)-2-chloro-4-fluoro-5-(3,5-dimethyl-2,6-dioxo-4-thio-1,3,5-triazine-1-yl)benzoic acid (1-(2-chloroethoxycarbonyl)ethyl ester

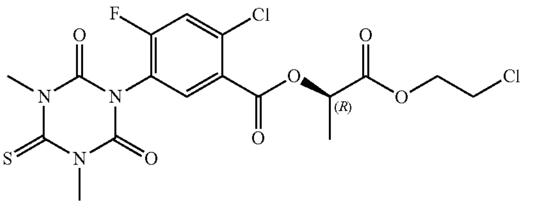

Step a) Synthesis of Intermediate (S)-2-bromopropionic acid (2-chloroethanol) ester

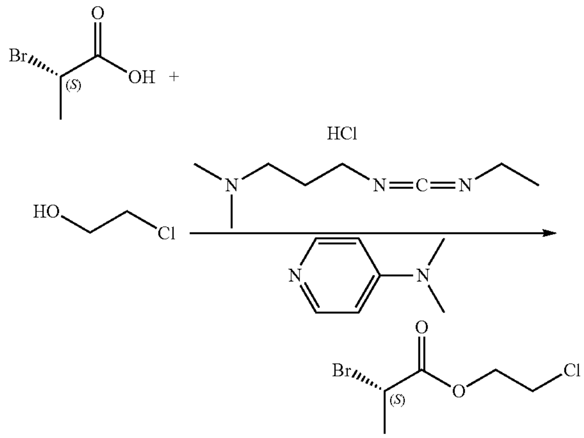

In a 250 mL reaction flask, (S)-2-bromopropionic acid (7.65 g, 50.0 mmol), 2-chloroethanol (4.10 g, 50.9 mmol), and 4-(N,N-dimethylamino)pyridine (DMAP, 1.22 g, 10.0 mmol) were mixed in 50 mL of dichloromethane to form a solution. 1-(3-dimethylaminopropyl)-3-ethylcarbodiimide hydrochloride (EDC·HCl, 19.20 g, 100.0 mmol) was added in batches into the reaction flask at room temperature. After the material was added, the material was stirred at room temperature for 2 h. The reaction solution was poured into 50 mL of water, and extracted with dichloromethane (50 mL×2); the combined organic layer was washed with 50 mL of saturated salt water, dried with anhydrous magnesium sulfate, and concentrated under reduced pressure to obtain 8.50 g of yellow liquid with a yield of 79%. The liquid is directly used for reaction in the next step without further purification.

Step b) Synthesis of Compound 266 (R)-2-chloro-4-fluoro-5-(3,5-dimethyl-2,6-dioxo-4-thio-1,3,5-triazine-1-yl)benzoic acid (1-(2-chloroethoxycarbonyl)ethyl ester

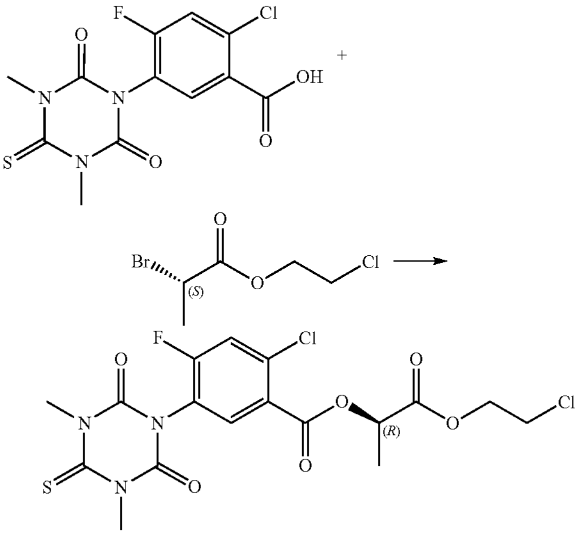

2-chloro-4-fluoro-5-(3,5-dimethyl-2,6-dioxo-4-thio-1,3,5-triazine-1-yl)benzoic acid (0.24 g, 0.7 mmol) and potassium carbonate (0.10 g, 0.7 mmol) were mixed and dissolved in 5 mL of N,N-dimethylformamide (DMF) in a 100 mL reaction flask to form suspension; and (S)-2-bromopropionic acid (2-chloroethanol) ester (0.15 g, 0.7 mmol) was added to the suspension at room temperature. After the material was added, the material was stirred at room temperature for 2 h. The reaction solution was poured into 20 mL of water, and extracted with ethyl acetate (10 mL×3); the combined organic layer was washed with 10 mL of saturated salt water, dried with anhydrous magnesium sulfate, and concentrated under reduced pressure to obtain yellow viscous liquid. Column chromatography separation ($SiO_2$, EtOAc:P.E.=1:4) was conducted to obtain 0.12 g of compound 266, (R)-2-chloro-4-fluoro-5-(3,5-dimethyl-2,6-dioxo-4-thio-1,3,5-triazine-1-yl)benzoic acid (1-(2-chloroethoxycarbonyl)ethyl ester, i.e., colorless foam substance with a yield of 36%. The purity is 96.7%. (HPLC: 18.167 min; chromatographic conditions: DAICEL Chemical Industries, Ltd. ChiralPak AD-H type chiral column, isopropanol:n-hexane=10:90, flow rate 1.0 mL/s, and detection wavelength 254 nm.)

Embodiment 10: Synthesis of Compound 267 (S)-2-chloro-4-fluoro-5-(3,5-dimethyl-2,6-dioxo-4-thio-1,3,5-triazine-1-yl)benzoic acid (1-(2-chloroethoxy-carbonyl)ethyl ester

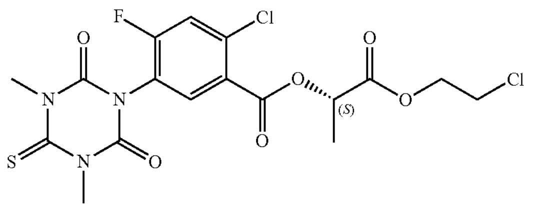

Step a) Synthesis of Intermediate (R)-2-bromopropionic acid (2-chloroethanol) ester

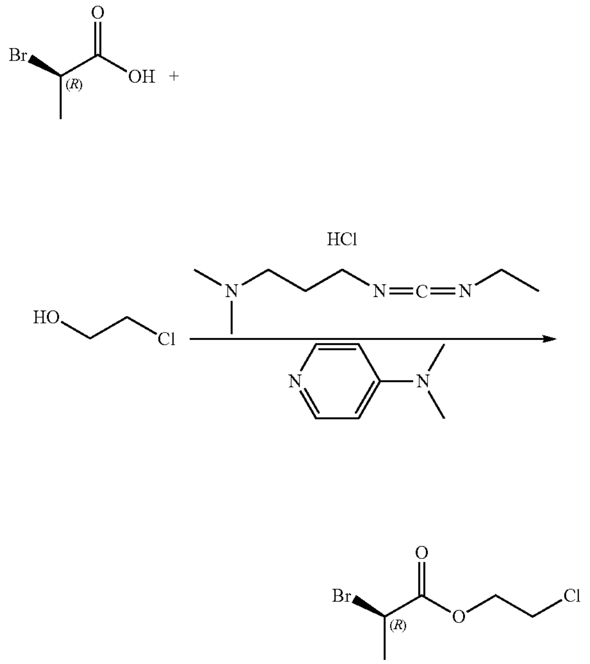

In a 250 mL reaction flask, (R)-2-bromopropionic acid (7.65 g, 50.0 mmol), 2-chloroethanol (4.10 g, 50.9 mmol), and 4-(N,N-dimethylamino)pyridine (DMAP, 1.22 g, 10.0 mmol) were mixed in 50 mL of dichloromethane to form a solution. 1-(3-dimethylaminopropyl)-3-ethylcarbodiimide hydrochloride (EDC·HCl, 19.20 g, 100.0 mmol) was added in batches into the reaction flask at room temperature. After the material was added, the material was stirred at room temperature for 2 h. The reaction solution was poured into 50 mL of water, and extracted with dichloromethane (50 mL×2); the combined organic layer was washed with 50 mL of saturated salt water, dried with anhydrous magnesium sulfate, and concentrated under reduced pressure to obtain 8.50 g of yellow liquid with a yield of 79%. The liquid is directly used for reaction in the next step without further purification.

Step b) Synthesis of Compound 267 (S)-2-chloro-4-fluoro-5-(3,5-dimethyl-2,6-dioxo-4-thio-1,3,5-triazine-1-yl)benzoic acid (1-(2-chloroethoxycarbonyl) ethyl ester

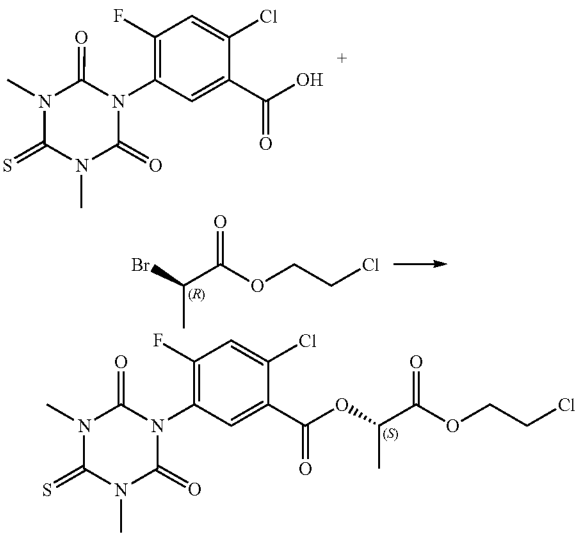

2-chloro-4-fluoro-5-(3,5-dimethyl-2,6-dioxo-4-thio-1,3,5-triazine-1-yl)benzoic acid (0.24 g, 0.7 mmol) and potassium carbonate (0.10 g, 0.7 mmol) were mixed and dissolved in 5 mL of N,N-dimethylformamide (DMF) in a 100 mL reaction flask to form suspension; and (R)-2-bromopropionic acid (2-chloroethanol) ester (0.15 g, 0.7 mmol) was added to the suspension at room temperature. After the material was added, the material was stirred at room temperature for 2 h. The reaction solution was poured into 20 mL of water, and extracted with ethyl acetate (10 mL×3); the combined organic layer was washed with 10 mL of saturated salt water, dried with anhydrous magnesium sulfate, and concentrated under reduced pressure to obtain yellow viscous liquid. Column chromatography separation ($SiO_2$, EtOAc:P.E.=1:4) was conducted to obtain 0.12 g of compound 267, (S)-2-chloro-4-fluoro-5-(3,5-dimethyl-2,6-dioxo-4-thio-1,3,5-triazine-1-yl)benzoic acid (1-(2-chloroethoxycarbonyl)ethyl ester, i.e., colorless foam substance with a yield of 36%. The purity is 95.8%. (HPLC: 20.650 min; chromatographic conditions: DAICEL Chemical Industries, Ltd. ChiralPak AD-H type chiral column, isopropanol:n-hexane=10:90, flow rate 1.0 mL/s, and detection wavelength 254 nm.)

Embodiment 11: Synthesis of Compound 281 (E)-2-chloro-4-fluoro-5-(3,5-dimethyl-2,6-dioxo-4-thio-1,3,5-triazine-1-yl)benzoic acid (1-(3-chloroallyloxycarbonyl))ethyl ester

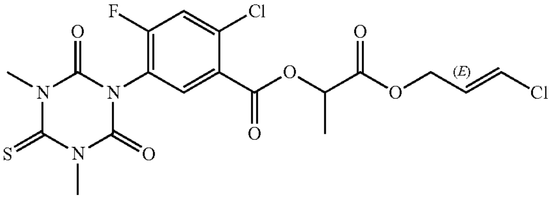

-continued

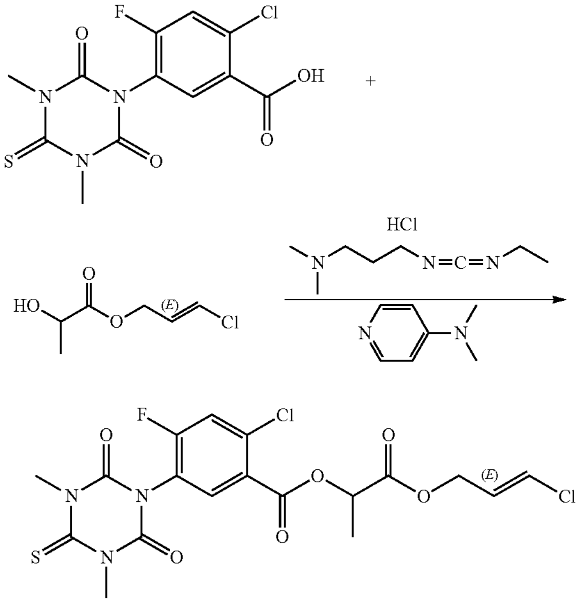

2-chloro-4-fluoro-5-(3,5-dimethyl-2,6-dioxo-4-thio-1,3,5-triazine-1-yl)benzoic acid (0.42 g, 1.2 mmol), lactic acid (3-chloroallyl alcohol)ester (0.25 g, 1.5 mmol, available in the market) and 4-(N,N-dimethylamino)pyridine (DMAP, 0.03 g, 0.2 mmol) were mixed and dissolved in 15 mL of dichloromethane in a 100 mL reaction flask to form suspension. 1-(3-dimethylaminopropyl)-3-ethylcarbodiimide hydrochloride (EDC·HCl, 0.35 g, 1.8 mmol) was added in batches into the reaction flask at room temperature, and the reaction system was changed from the suspension to a clear solution. After the material was added, the material was stirred at room temperature for 2 h. The reaction solution was poured into 50 mL of water, and extracted with dichloromethane (15 mL×2); the combined organic layer was washed with 15 mL of saturated salt water, dried with anhydrous magnesium sulfate, and concentrated under reduced pressure to obtain yellow viscous liquid. Column chromatography separation ($SiO_2$, EtOAc:P.E.=1:6) was conducted to obtain 0.15 g of compound 281, (E)-2-chloro-4-fluoro-5-(3,5-dimethyl-2,6-dioxo-4-thio-1,3,5-triazine-1-yl)benzoic acid (1-(3-chloroallyloxycarbonyl))ethyl ester, i.e., colorless liquid with a yield of 25%.

Embodiment 12: Synthesis of Compound 298 2-chloro-4-fluoro-5-(3,5-dimethyl-2,6-dioxo-4-thio-1,3,5-triazine-1-yl) benzoic acid (1-(isoxazolin-2-ylmethoxycarbonyl))ethyl ester

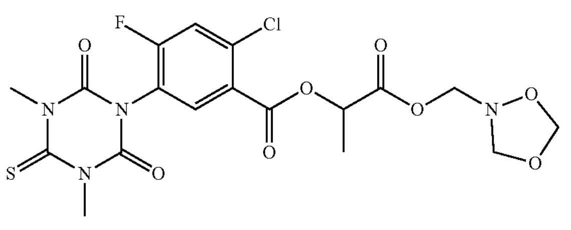 [SMILES: CC(OC(=O)c1cc(-n2c(=O)n(C)c(=S)n(C)c2=O)c(F)cc1Cl)C(=O)OCN1COCO1]

Step a) Synthesis of Intermediate 2-bromopropionyl Chloride

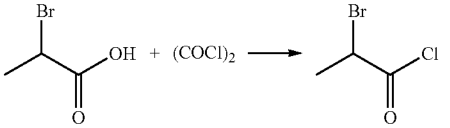

In a 100 mL reaction flask, 2-bromopropionic acid (0.50 g, 3.27 mmol) was dissolved in 20 mL of dichloromethane; oxalyl chloride (1.66 g, 13.07 mmol) was added; and 2 drops of N,N-dimethylformamide were added dropwise at room temperature. After the material was added, the material was stirred at room temperature for 2 h. The solvent and excess oxalyl chloride were spun off, and dissolved in 10 mL of dichloromethane for later use.

Step b) Synthesis of Intermediate 2-bromo-1-(isoxazolidine-2-yl)propan-1-one

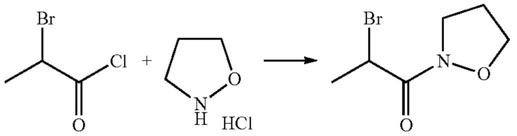

In a 100 mL reaction flask, 4-hydroisoxazole hydrochloride (0.36 g, 3.27 mmol) was dissolved in 20 mL of dichloromethane; 2-bromopropionyl chloride obtained in the above step was added; and triethylamine (0.66 g, 6.54 mmol) was added. After the material was added, the material was stirred at room temperature for 2 h. The solvent was spun off, and was directly used for reaction in the next step without further purification.

Step c) Synthesis of Compound 298 2-chloro-4-fluoro-5-(3,5-dimethyl-2,6-dioxo-4-thio-1,3,5-triazine-1-yl) benzoic acid (1-(isoxazolin-2-ylmethoxycarbonyl))ethyl ester

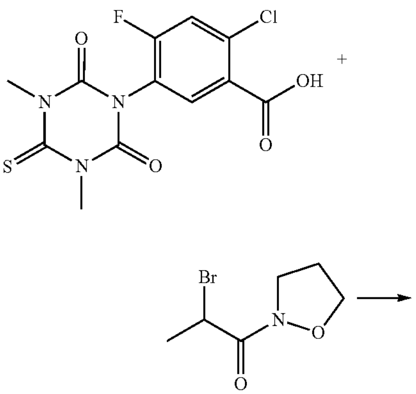

-continued

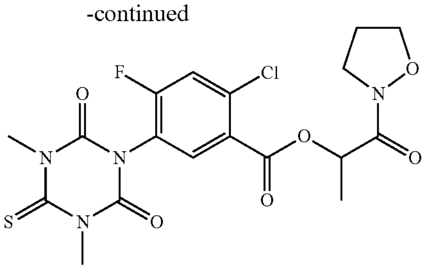

2-chloro-4-fluoro-5-(3,5-dimethyl-2,6-dioxo-4-thio-1,3,5-triazine-1-yl)benzoic acid (1.00 g, 2.89 mmol) and potassium carbonate (0.72 g, 3.47 mmol) were mixed and dissolved in 5 mL of N,N-dimethylformamide (DMF) in a 100 mL reaction flask to form suspension; and 2-bromo-1-(isoxazolidine-2-yl)propan-1-one prepared in the above step was added to the suspension at room temperature. After the addition was completed, the temperature was raised to 80° C. and stirring was continued for 2 h. The reaction was completed after 2 h. The reaction solution was poured into 20 mL of water, and extracted with ethyl acetate (10 mL×3); the combined organic layer was washed with 10 mL of saturated salt water, dried with anhydrous magnesium sulfate, and concentrated under reduced pressure to obtain yellow viscous liquid. Column chromatography separation ($SiO_2$, EtOAc:PE.=1:4) was conducted to obtain 120 mg of target compound 298, 2-chloro-4-fluoro-5-(3,5-dimethyl-2,6-dioxo-4-thio-1,3,5-triazine-1-yl) benzoic acid (1-(isoxazolin-2-ylmethoxycarbonyl))ethyl ester, i.e., yellowish oily liquid with a yield of 9%.

Embodiment 13: Synthesis of Compound 300 2-chloro-4-fluoro-5-(3,5-dimethyl-2,6-dioxo-4-thio-1,3,5-triazine-1-yl)benzoic acid (1-(2-fluoroethoxycarbonyl))propyl ester

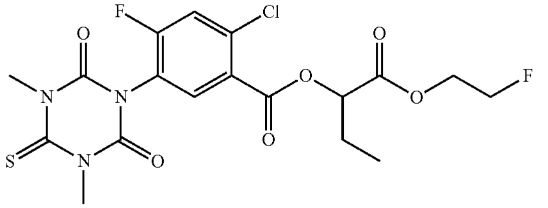 [SMILES: CCC(OC(=O)c1cc(-n2c(=O)n(C)c(=S)n(C)c2=O)c(F)cc1Cl)C(=O)OCCF]

Step a) Synthesis of Intermediate 2-bromobutyric acid (2-fluoroethanol) ester

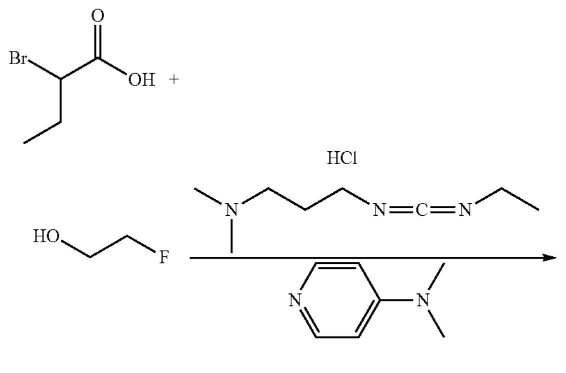

-continued

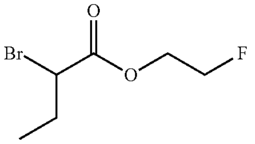

In a 250 mL reaction flask, 2-bromobutyric acid (4.18 g, 25.0 mmol), 2-fluoroethanol (1.63 g, 25.5 mmol) and 4-(N,N-dimethylamino)pyridine (DMAP, 0.61 g, 5.0 mmol) were mixed in 25 mL of dichloromethane to form a solution. 1-(3-dimethylaminopropyl)-3-ethylcarbodiimide hydrochloride (EDC·HCl, 9.60 g, 50.0 mmol) was added in batches into the reaction flask at room temperature. After the material was added, the material was stirred at room temperature for 2 h. The reaction solution was poured into 50 mL of water, and extracted with dichloromethane (50 mL×2); the combined organic layer was washed with 50 mL of saturated salt water, dried with anhydrous magnesium sulfate, and concentrated under reduced pressure to obtain 3.60 g of yellow liquid with a yield of 68%. The liquid is directly used for reaction in the next step without further purification.

Step b) Synthesis of Compound 300 2-chloro-4-fluoro-5-(3,5-dimethyl-2,6-dioxo-4-thio-1,3,5-triazine-1-yl)benzoic acid (1-(2-fluoroethoxycarbonyl)) propyl ester

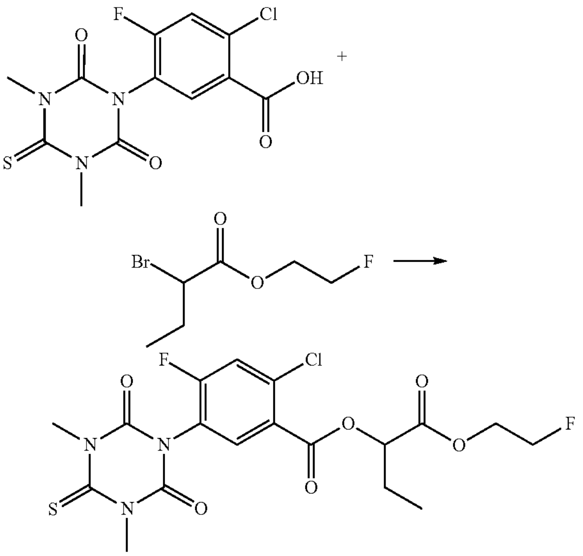

2-chloro-4-fluoro-5-(3,5-dimethyl-2,6-dioxo-4-thio-1,3,5-triazine-1-yl)benzoic acid (0.52 g, 1.5 mmol) and potassium carbonate (0.22 g, 1.6 mmol) were mixed and dissolved in 5 mL of N,N-dimethylformamide (DMF) in a 100 mL reaction flask to form suspension; and 2-bromobutyric acid (2-fluoroethanol) ester (0.32 g, 1.5 mmol) was added to the suspension at room temperature. After the material was added, the material was stirred at room temperature for 2 h. The reaction solution was poured into 20 mL of water, and extracted with ethyl acetate (10 mL×3); the combined organic layer was washed with 10 mL of saturated salt water, dried with anhydrous magnesium sulfate, and concentrated under reduced pressure to obtain yellow viscous liquid.

Column chromatography separation ($SiO_2$, EtOAc:P.E.=1:4) was conducted to obtain 0.50 g of compound 300, 2-chloro-4-fluoro-5-(3, 5-dimethyl-2,6-dioxo-4-thio-1,3,5-triazine-1-yl)benzoic acid (1-(2-fluoroethoxycarbonyl))propyl ester, i.e., colorless foam substance with a yield of 70%.

Embodiment 14: Compound 306 2-chloro-4-fluoro-5-(3,5-dimethyl-2,6-dioxo-4-thio-1,3,5-triazine-1-yl) benzoic acid (1-methyl-1-ethoxycarbonyl)ethyl ester

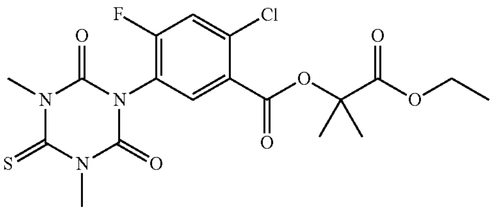 [SMILES: CCOC(=O)C(C)(C)OC(=O)c1cc(-n2c(=O)n(C)c(=S)n(C)c2=O)c(F)cc1Cl]

Step a) Synthesis of Intermediate 2-chloro-4-fluoro-5-nitrobenzoic acid (1-methyl-1-ethoxycarbonyl) ethyl ester

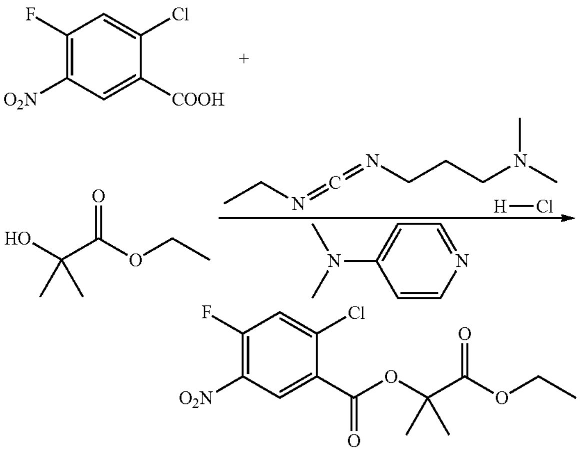

2-chloro-4-fluoro-5-nitrobenzoic acid (5.49 g, 25.0 mmol), ethyl α-hydroxyisobutyrate (4.00 g, 30.0 mmol), 4-(N,N-dimethylamino)pyridine (DMAP, 0.30 g, 2.5 mmol) and dichloromethane (50 mL) were added to a 250 mL reaction flask; 1-(3-dimethylaminopropyl)-3-ethyl carbodiimide hydrochloride (EDC·HCl, 9.60 g, 50.0 mmol) was added in batches to the reaction flask while stirring at room temperature; and the reaction system was changed from the suspension to a clear solution. After the material was added, the material was stirred at room temperature for 2 h. The reaction solution was poured into 50 mL of water and extracted with 50 mL of dichloromethane; and a combined organic layer was washed with 30 mL of saturated salt water, dried with anhydrous magnesium sulphate and concentrated under reduced pressure to obtain 2.70 g of yellow liquid with a crude yield of 33%. The obtained intermediate 2-chloro-4-fluoro-5-nitrobenzoic acid (1-methyl-1-ethoxycarbonyl) ethyl ester is directly used for synthesis in the next step without further purification.

Step b) Synthesis of Intermediate 5-amino-2-chloro-4-fluorobenzoic acid (1-methyl-1-ethoxycarbonyl)ethyl ester

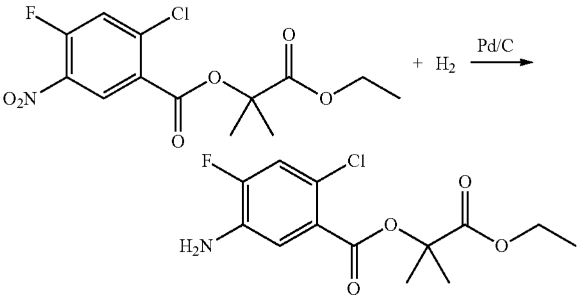

In a 100 mL reaction flask, 2-chloro-4-fluoro-5-nitrobenzoic acid (1-methyl-1-ethoxycarbonyl)ethyl ester (2.70 g, 8.10 mmol) was mixed with 20 mL of methanol to form a solution; 10% palladium/carbon catalyst (0.25 g) was added; and a hydrogen flow was introduced for 2 h through the reaction at room temperature. After the TLC monitored that the reaction was completed, the catalyst is removed through filtration. The solvent was evaporated out from the filtrate under reduced pressure to obtain 1.80 g of yellow liquid with a crude yield of 73%. The obtained 5-amino-2-chloro-4-fluorobenzoic acid (1-methyl-1-ethoxycarbonyl)ethyl ester is directly used for synthesis in the next step without further purification.

Step c) Synthesis of Compound 306 2-chloro-4-fluoro-5-(3,5-dimethyl-2,6-dioxo-4-thio-1,3,5-triazine-1-yl)benzoic acid (1-methyl-1-ethoxycarbonyl) ethyl ester

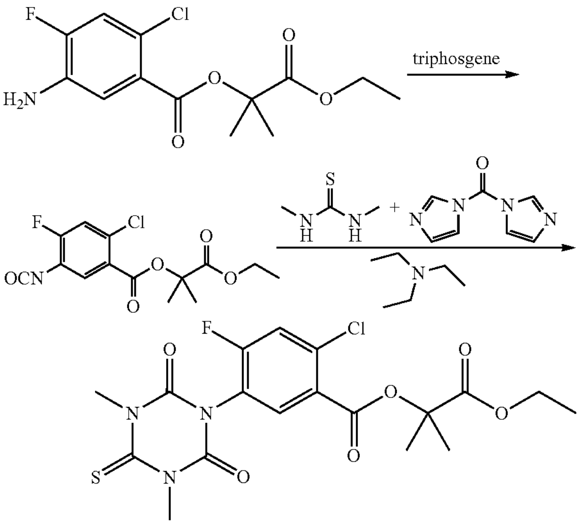

15 mL of toluene was added to a 100 mL reaction flask; 5-amino-2-chloro-4-fluorobenzoic acid (1-methyl-1-ethoxycarbonyl)ethyl ester (1.80 g, 6.0 mmol) and triphosgene (0.90 g, 3.0 mmol) were added in sequence; the solution was heated to reflux and the reaction was kept under the reflux condition for 2 h. After returning to room temperature, a toluene solution of isocyanate was obtained for later use.

15 mL of toluene, 1,3-dimethylthiourea (1.75 g, 16.8 mmol) and triethylamine (1.0 mL, 7.2 mmol) were successively added to another 100 mL reaction flask; the above prepared toluene solution of isocyanate was added dropwise to the reaction flask at room temperature; after dropwise adding, carbonyldiimidazole (DCI, 1.45 g, 9.0 mmol) was added, and heated to reflux; and the reaction was kept under the reflux condition for 2 h. After the reaction was completed, 30 mL of toluene was added thereto, washed with saturated salt water (15 mL×2), dried with anhydrous magnesium sulfate, and concentrated under reduced pressure to obtain brown viscous liquid. Column chromatography separation ($SiO_2$, EtOAc:P.E.=1:9, then 1:4) was conducted to obtain 1.80 g of compound 306, 2-chloro-4-fluoro-5-(3,5-dimethyl-2,6-dioxo-4-thio-1,3,5-triazine-1-yl)benzoic acid (1-methyl-1-ethoxycarbonyl)ethyl ester, i.e., white solid (m.p. 98-100° C.) with a yield of 66%.

The initial substances are replaced according to the above recorded method to obtain other compounds shown by the formula I. The structures and physical properties of part of the compounds of the formula I can be found in Table 1.

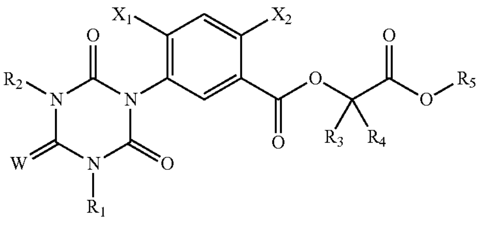

(I)

TABLE 1

| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 1. | O | F | Cl | Me | Me | H | Me | Et | | yellow oil |
| 2. | O | F | Cl | Me | Me | H | Me | n-Pr | | |
| 3. | O | F | Cl | Me | Me | H | Me | i-Pr | | |
| 4. | O | F | Cl | Me | Me | H | Me | n-Bu | | |
| 5. | O | F | Cl | Me | Me | H | Me | i-Bu | | |
| 6. | O | F | Cl | Me | Me | H | Me | s-Bu | | |
| 7. | O | F | Cl | Me | Me | H | Me | t-Bu | | |
| 8. | O | F | Cl | Me | Me | H | Me | 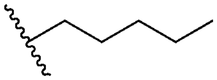 [SMILES: *CCCCC] | | |
| 9. | O | F | Cl | Me | Me | H | Me | 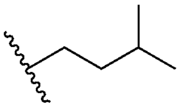 [SMILES: *CCC(C)C] | | |
| 10. | O | F | Cl | Me | Me | H | Me | 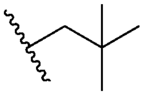 [SMILES: *CC(C)(C)C] | | |
| 11. | O | F | Cl | Me | Me | H | Me | 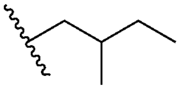 [SMILES: *CC(C)CC] | | |
| 12. | O | F | Cl | Me | Me | H | Me | 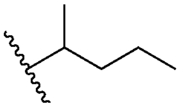 [SMILES: *C(C)CCC] | | |
| 13. | O | F | Cl | Me | Me | H | Me | 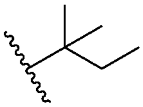 [SMILES: *C(C)(C)CC] | | |
| 14. | O | F | Cl | Me | Me | H | Me | 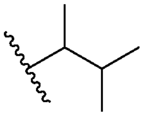 [SMILES: *C(C)C(C)C] | | |
| 15. | O | F | Cl | Me | Me | H | Me | 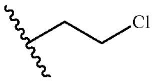 [SMILES: *CCCl] | | yellow oil |

TABLE 1-continued
| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 16. | O | F | Cl | Me | Me | H | Me | 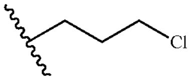 [SMILES: *CCCCl] | | yellow oil |
| 17. | O | F | Cl | Me | Me | H | Me | 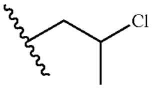 [SMILES: *CC(C)Cl] | | |
| 18. | O | F | Cl | Me | Me | H | Me | 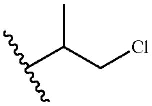 [SMILES: *C(C)CCl] | | |
| 19. | O | F | Cl | Me | Me | H | Me | 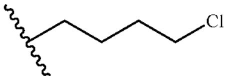 [SMILES: *CCCCCl] | | yellow oil |
| 20. | O | F | Cl | Me | Me | H | Me | 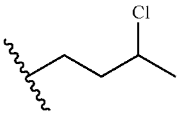 [SMILES: *CCC(C)Cl] | | |
| 21. | O | F | Cl | Me | Me | H | Me | 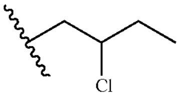 [SMILES: *CC(Cl)CC] | | |
| 22. | O | F | Cl | Me | Me | H | Me | 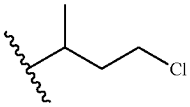 [SMILES: *C(C)CCCl] | | |
| 23. | O | F | Cl | Me | Me | H | Me | 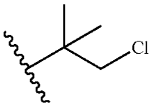 [SMILES: *C(C)(C)CCl] | | |
| 24. | O | F | Cl | Me | Me | H | Me | 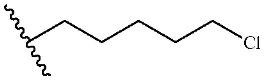 [SMILES: *CCCCCCl] | | |
| 25. | O | F | Cl | Me | Me | H | Me | 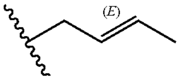 [SMILES: *C/C=C/C] | | |
| 26. | O | F | Cl | Me | Me | H | Me | 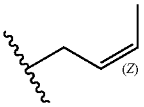 [SMILES: *C/C=C\C] | | |
| 27. | O | F | Cl | Me | Me | H | Me | 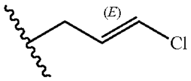 [SMILES: *C/C=C/Cl] | | |
| 28. | O | F | Cl | Me | Me | H | Me | 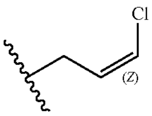 | | |

TABLE 1-continued

| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 29. | O | F | Cl | Me | Me | H | Me | 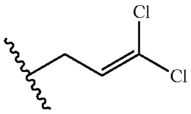 | | |
| 30. | O | F | Cl | Me | Me | H | Me | 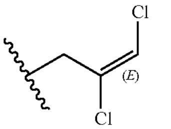 [SMILES: *C/C(Cl)=C\Cl] | | |
| 31. | O | F | Cl | Me | Me | H | Me | 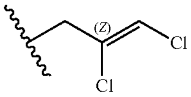 [SMILES: *C/C(Cl)=C/Cl] | | |
| 32. | O | F | Cl | Me | Me | H | Me | 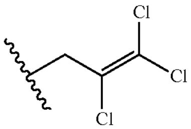 [SMILES: *CC(Cl)=C(Cl)Cl] | | |
| 33. | O | F | Cl | Me | Me | H | Me | 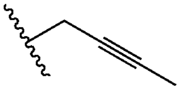 [SMILES: *CC#CC] | | yellow oil |
| 34. | O | F | Cl | Me | Me | H | Me | 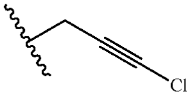 [SMILES: *CC#CCl] | | |
| 35. | O | F | Cl | Me | Me | H | Me | 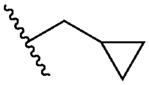 | | yellow oil |
| 36. | O | F | Cl | Me | Me | H | Me | 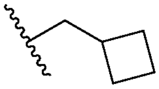 [SMILES: *CC1CCC1] | | |
| 37. | O | F | Cl | Me | Me | H | Me | 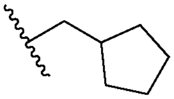 | | yellow oil |
| 38. | O | F | Cl | Me | Me | H | Me | 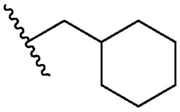 [SMILES: *CC1CCCCC1] | | |
| 39. | O | F | Cl | Me | Me | H | Me | 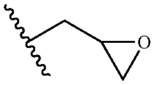 [SMILES: *CC1CO1] | | |
| 40. | O | F | Cl | Me | Me | H | Me | 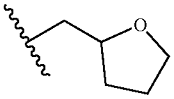 [SMILES: *CC1CCCO1] | | |
| 41. | O | F | Cl | Me | Me | H | Et | Et | | yellow oil |
| 42. | O | F | Cl | Me | Me | H | i-Pr | Et | | orange oil |
| 43. | O | F | Cl | Me | Me | Me | Me | Et | | |
| 44. | O | F | Cl | Me | Me | Me | Me | n-Pr | | |
| 45. | O | F | Cl | Me | Me | Me | Me | i-Pr | | |
| 46. | O | F | Cl | Me | Me | Me | Me | n-Bu | | |

TABLE 1-continued
| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 47. | O | F | Cl | Me | Me | Me | Me | i-Bu | | |
| 48. | O | F | Cl | Me | Me | Me | Me | s-Bu | | |
| 49. | O | F | Cl | Me | Me | Me | Me | t-Bu | | |
| 50. | O | F | Cl | Me | Me | Me | Me | 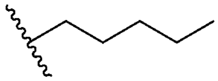 [SMILES: *CCCCC] | | |
| 51. | O | F | Cl | Me | Me | Me | Me | 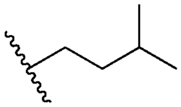 | | |
| 52. | O | F | Cl | Me | Me | Me | Me | 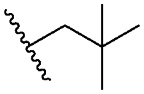 [SMILES: *CC(C)(C)C] | | |
| 53. | O | F | Cl | Me | Me | Me | Me | 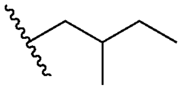 [SMILES: *CC(C)CC] | | |
| 54. | O | F | Cl | Me | Me | Me | Me | 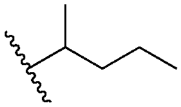 [SMILES: *C(C)CCC] | | |
| 55. | O | F | Cl | Me | Me | Me | Me | 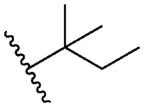 [SMILES: *C(C)(C)CC] | | |
| 56. | O | F | Cl | Me | Me | Me | Me | 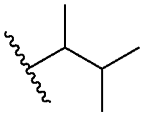 [SMILES: *C(C)C(C)C] | | |
| 57. | O | F | Cl | Me | Me | Me | Me | 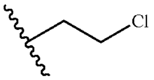 [SMILES: *CCCl] | | |
| 58. | O | F | Cl | Me | Me | Me | Me | 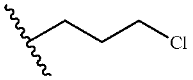 | | |
| 59. | O | F | Cl | Me | Me | Me | Me | 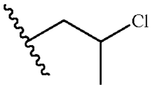 [SMILES: *CC(C)Cl] | | |
| 60. | O | F | Cl | Me | Me | Me | Me | 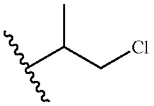 [SMILES: *C(C)CCl] | | |
| 61. | O | F | Cl | Me | Me | Me | Me | 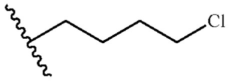 [SMILES: *CCCCCl] | | |
| 62. | O | F | Cl | Me | Me | Me | Me | 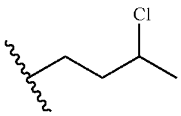 [SMILES: *CCC(C)Cl] | | |

TABLE 1-continued
| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 63. | O | F | Cl | Me | Me | Me | Me | 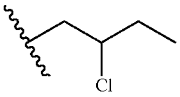 [SMILES: *CC(Cl)CC] | | |
| 64. | O | F | Cl | Me | Me | Me | Me | 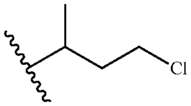 [SMILES: *C(C)CCCl] | | |
| 65. | O | F | Cl | Me | Me | Me | Me | 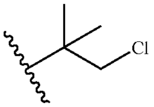 [SMILES: *C(C)(C)CCl] | | |
| 66. | O | F | Cl | Me | Me | Me | Me | 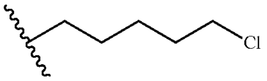 [SMILES: *CCCCCCl] | | |
| 67. | O | F | Cl | Me | Me | Me | Me | 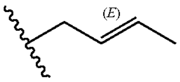 [SMILES: *C/C=C/C] | | |
| 68. | O | F | Cl | Me | Me | Me | Me | 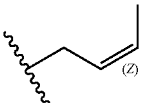 [SMILES: *C/C=C\C] | | |
| 69. | O | F | Cl | Me | Me | Me | Me | 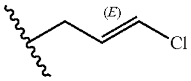 [SMILES: *C/C=C/Cl] | | |
| 70. | O | F | Cl | Me | Me | Me | Me | 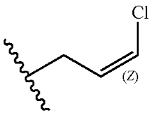 [SMILES: *C/C=C\Cl] | | |
| 71. | O | F | Cl | Me | Me | Me | Me | 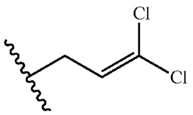 [SMILES: *CC=C(Cl)Cl] | | |
| 72. | O | F | Cl | Me | Me | Me | Me | 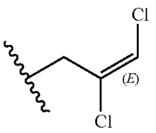 [SMILES: *C/C(Cl)=C\Cl] | | |
| 73. | O | F | Cl | Me | Me | Me | Me | 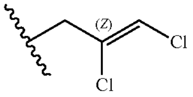 [SMILES: *C/C(Cl)=C/Cl] | | |
| 74. | O | F | Cl | Me | Me | Me | Me | 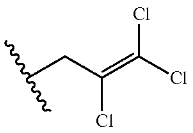 [SMILES: *CC(Cl)=C(Cl)Cl] | | |
| 75. | O | F | Cl | Me | Me | Me | Me | 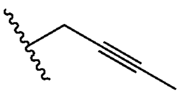 [SMILES: *CC#CC] | | |

TABLE 1-continued
| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 76. | O | F | Cl | Me | Me | Me | Me | 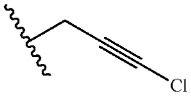 [SMILES: *CC#CCl] | | |
| 77. | O | F | Cl | Me | Me | Me | Me | 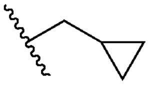 [SMILES: *CC1CC1] | | |
| 78. | O | F | Cl | Me | Me | Me | Me | 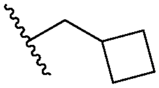 [SMILES: *CC1CCC1] | | |
| 79. | O | F | Cl | Me | Me | Me | Me | 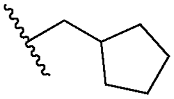 | | |
| 80. | O | F | Cl | Me | Me | Me | Me | 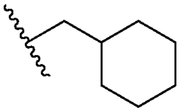 [SMILES: *CC1CCCCC1] | | |
| 81. | O | F | Cl | Me | Me | Me | Me | 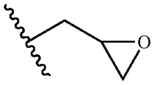 [SMILES: *CC1CO1] | | |
| 82. | O | F | Cl | Me | Me | Me | Me | 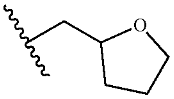 | | |
| 83. | S | H | Cl | Me | Me | H | H | Et | | |
| 84. | S | H | Cl | Me | Me | H | H | n-Pr | | |
| 85. | S | H | Cl | Me | Me | H | H | i-Pr | | |
| 86. | S | H | Cl | Me | Me | H | H | n-Bu | | |
| 87. | S | H | Cl | Me | Me | H | H | i-Bu | | |
| 88. | S | H | Cl | Me | Me | H | H | s-Bu | | |
| 89. | S | H | Cl | Me | Me | H | H | t-Bu | | |
| 90. | S | H | Cl | Me | Me | H | H | 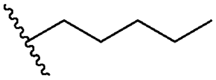 [SMILES: *CCCCC] | | |
| 91. | S | H | Cl | Me | Me | H | H | 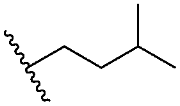 [SMILES: *CCC(C)C] | | |
| 92. | S | H | Cl | Me | Me | H | H | 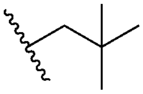 [SMILES: *CC(C)(C)C] | | |
| 93. | S | H | Cl | Me | Me | H | H | 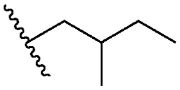 [SMILES: *CC(C)CC] | | |
| 94. | S | H | Cl | Me | Me | H | H | 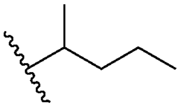 [SMILES: *C(C)CCC] | | |

TABLE 1-continued
| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 95. | S | H | Cl | Me | Me | H | H | 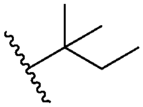 [SMILES: *C(C)(C)CC] | | |
| 96. | S | H | Cl | Me | Me | H | H | 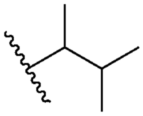 [SMILES: *C(C)C(C)C] | | |
| 97. | S | H | Cl | Me | Me | H | H | 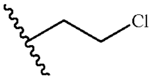 [SMILES: *CCCl] | | white wax |
| 98. | S | H | Cl | Me | Me | H | H | 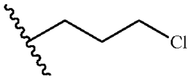 [SMILES: *CCCCl] | | |
| 99. | S | H | Cl | Me | Me | H | H | 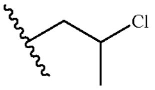 [SMILES: *CC(C)Cl] | | |
| 100. | S | H | Cl | Me | Me | H | H | 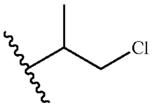 [SMILES: *C(C)CCl] | | |
| 101. | S | H | Cl | Me | Me | H | H | 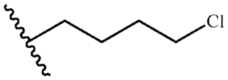 [SMILES: *CCCCCl] | | |
| 102. | S | H | Cl | Me | Me | H | H | 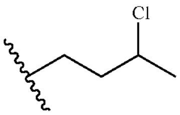 | | |
| 103. | S | H | Cl | Me | Me | H | H | 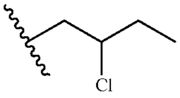 [SMILES: *CC(Cl)CC] | | |
| 104. | S | H | Cl | Me | Me | H | H | 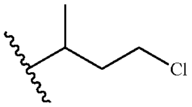 [SMILES: *C(C)CCCl] | | |
| 105. | S | H | Cl | Me | Me | H | H | 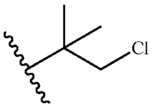 [SMILES: *C(C)(C)CCl] | | |
| 106. | S | H | Cl | Me | Me | H | H | 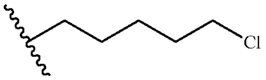 [SMILES: *CCCCCCl] | | |
| 107. | S | H | Cl | Me | Me | H | H | 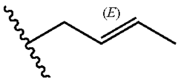 [SMILES: *C/C=C/C] | | |

TABLE 1-continued
| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 108. | S | H | Cl | Me | Me | H | H | 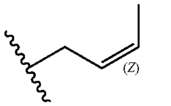 [SMILES: *C/C=C\C] | | |
| 109. | S | H | Cl | Me | Me | H | H | 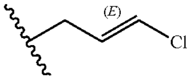 [SMILES: *C/C=C/Cl] | | |
| 110. | S | H | Cl | Me | Me | H | H | 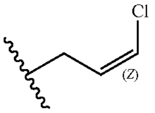 | | |
| 111. | S | H | Cl | Me | Me | H | H | 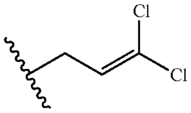 [SMILES: *CC=C(Cl)Cl] | | |
| 112. | S | H | Cl | Me | Me | H | H | 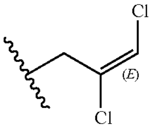 [SMILES: *C/C(Cl)=C\Cl] | | |
| 113. | S | H | Cl | Me | Me | H | H | 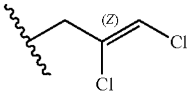 [SMILES: *C/C(Cl)=C/Cl] | | |
| 114. | S | H | Cl | Me | Me | H | H | 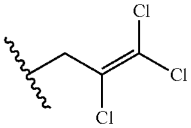 [SMILES: *CC(Cl)=C(Cl)Cl] | | |
| 115. | S | H | Cl | Me | Me | H | H | 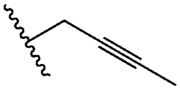 [SMILES: *CC#CC] | | |
| 116. | S | H | Cl | Me | Me | H | H | 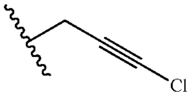 [SMILES: *CC#CCl] | | |
| 117. | S | H | Cl | Me | Me | H | H | 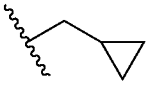 [SMILES: *CC1CC1] | | colorless foam |
| 118. | S | H | Cl | Me | Me | H | H | 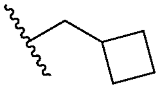 [SMILES: *CC1CCC1] | | |
| 119. | S | H | Cl | Me | Me | H | H | 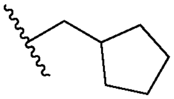 | | |
| 120. | S | H | Cl | Me | Me | H | H | 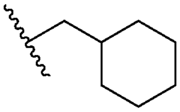 [SMILES: *CC1CCCCC1] | | |

TABLE 1-continued

| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 121. | S | H | Cl | Me | Me | H | H | 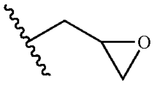 [SMILES: *CC1CO1] | | colorless foam |
| 122. | S | H | Cl | Me | Me | H | H | 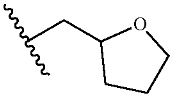 [SMILES: *CC1CCCO1] | | |
| 123. | S | H | Cl | Me | Me | H | H | 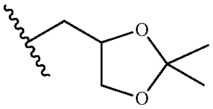 [SMILES: *CC1COC(C)(C)O1] | | yellow oil |
| 124. | S | H | Cl | Me | Me | H | Me | Et | | |
| 125. | S | H | Cl | Me | Me | H | Me | n-Pr | | |
| 126. | S | H | Cl | Me | Me | H | Me | i-Pr | | |
| 127. | S | H | Cl | Me | Me | H | Me | n-Bu | | |
| 128. | S | H | Cl | Me | Me | H | Me | i-Bu | | |
| 129. | S | H | Cl | Me | Me | H | Me | s-Bu | | |
| 130. | S | H | Cl | Me | Me | H | Me | t-Bu | | |
| 131. | S | H | Cl | Me | Me | H | Me | 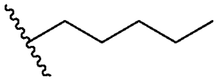 [SMILES: *CCCCC] | | |
| 132. | S | H | Cl | Me | Me | H | Me | 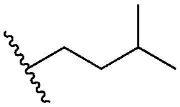 [SMILES: *CCC(C)C] | | |
| 133. | S | H | Cl | Me | Me | H | Me | 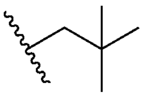 [SMILES: *CC(C)(C)C] | | |
| 134. | S | H | Cl | Me | Me | H | Me | 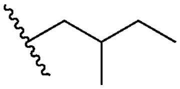 [SMILES: *CC(C)CC] | | |
| 135. | S | H | Cl | Me | Me | H | Me | 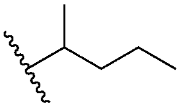 [SMILES: *C(C)CCC] | | |
| 136. | S | H | Cl | Me | Me | H | Me | 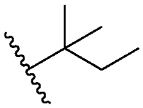 [SMILES: *C(C)(C)CC] | | |
| 137. | S | H | Cl | Me | Me | H | Me | 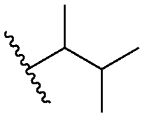 [SMILES: *C(C)C(C)C] | | |
| 138. | S | H | Cl | Me | Me | H | Me | 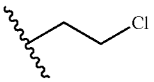 [SMILES: *CCCl] | rac. | colorless foam |
| 139. | S | H | Cl | Me | Me | H | Me | 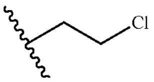 [SMILES: *CCCl] | R | colorless oil |

TABLE 1-continued
| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 140. | S | H | Cl | Me | Me | H | Me | 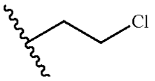 [SMILES: *CCCl] | S | pale yellow foam |
| 141. | S | H | Cl | Me | Me | H | Me | 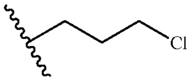 [SMILES: *CCCCl] | | |
| 142. | S | H | Cl | Me | Me | H | Me | 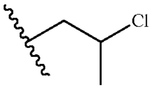 [SMILES: *CC(C)Cl] | | |
| 143. | S | H | Cl | Me | Me | H | Me | 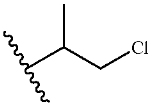 [SMILES: *C(C)CCl] | | |
| 144. | S | H | Cl | Me | Me | H | Me | 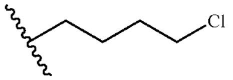 [SMILES: *CCCCCl] | | |
| 145. | S | H | Cl | Me | Me | H | Me | 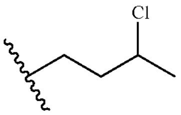 [SMILES: *CCC(C)Cl] | | |
| 146. | S | H | Cl | Me | Me | H | Me | 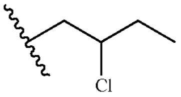 [SMILES: *CC(Cl)CC] | | |
| 147. | S | H | Cl | Me | Me | H | Me | 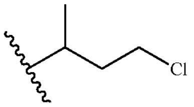 [SMILES: *C(C)CCCl] | | |
| 148. | S | H | Cl | Me | Me | H | Me | 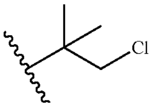 [SMILES: *C(C)(C)CCl] | | |
| 149. | S | H | Cl | Me | Me | H | Me | 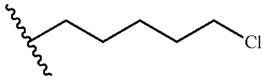 [SMILES: *CCCCCCl] | | |
| 150. | S | H | Cl | Me | Me | H | Me | 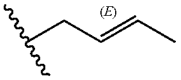 [SMILES: *C/C=C/C] | | |
| 151. | S | H | Cl | Me | Me | H | Me | 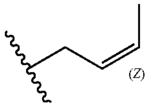 [SMILES: *C/C=C\C] | | |
| 152. | S | H | Cl | Me | Me | H | Me | 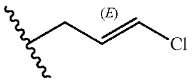 [SMILES: *C/C=C/Cl] | | yellow oil |
| 153. | S | H | Cl | Me | Me | H | Me | 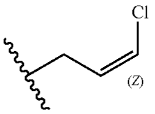 [SMILES: *C/C=C\Cl] | | |

TABLE 1-continued
| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 154. | S | H | Cl | Me | Me | H | Me | 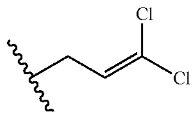 [SMILES: *CC=C(Cl)Cl] | | pale yellow oil |
| 155. | S | H | Cl | Me | Me | H | Me | 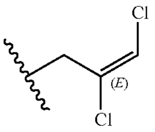 | | |
| 156. | S | H | Cl | Me | Me | H | Me | 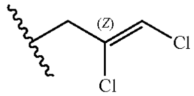 [SMILES: *C/C(Cl)=C/Cl] | | |
| 157. | S | H | Cl | Me | Me | H | Me | 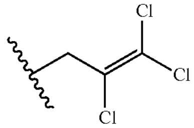 [SMILES: *CC(Cl)=C(Cl)Cl] | | |
| 158. | S | H | Cl | Me | Me | H | Me | 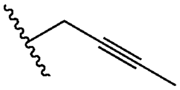 [SMILES: *CC#CC] | | |
| 159. | S | H | Cl | Me | Me | H | Me | 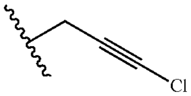 [SMILES: *CC#CCl] | | |
| 160. | S | H | Cl | Me | Me | H | Me | 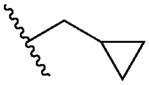 [SMILES: *CC1CC1] | | yellow foam |
| 161. | S | H | Cl | Me | Me | H | Me | 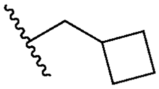 [SMILES: *CC1CCC1] | | |
| 162. | S | H | Cl | Me | Me | H | Me | 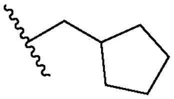 [SMILES: *CC1CCCC1] | | |
| 163. | S | H | Cl | Me | Me | H | Me | 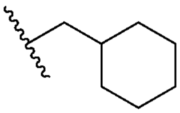 [SMILES: *CC1CCCCC1] | | |
| 164. | S | H | Cl | Me | Me | H | Me | 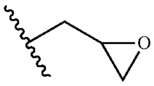 [SMILES: *CC1CO1] | | colorless foam |
| 165. | S | H | Cl | Me | Me | H | Me | 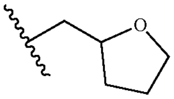 [SMILES: *CC1CCCO1] | | |

TABLE 1-continued

| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 166. | S | H | Cl | Me | Me | H | Me | 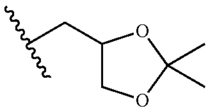 [SMILES: *CC1COC(C)(C)O1] | | colorless foam |
| 167. | S | H | Cl | Me | Me | Me | Me | Et | | |
| 168. | S | H | Cl | Me | Me | Me | Me | n-Pr | | |
| 169. | S | H | Cl | Me | Me | Me | Me | i-Pr | | |
| 170. | S | H | Cl | Me | Me | Me | Me | n-Bu | | |
| 171. | S | H | Cl | Me | Me | Me | Me | i-Bu | | |
| 172. | S | H | Cl | Me | Me | Me | Me | s-Bu | | |
| 173. | S | H | Cl | Me | Me | Me | Me | t-Bu | | |
| 174. | S | H | Cl | Me | Me | Me | Me | 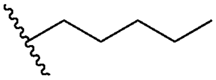 [SMILES: *CCCCC] | | |
| 175. | S | H | Cl | Me | Me | Me | Me | 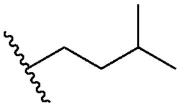 | | |
| 176. | S | H | Cl | Me | Me | Me | Me | 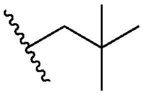 [SMILES: *CC(C)(C)C] | | |
| 177. | S | H | Cl | Me | Me | Me | Me | 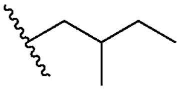 [SMILES: *CC(C)CC] | | |
| 178. | S | H | Cl | Me | Me | Me | Me | 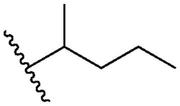 [SMILES: *C(C)CCC] | | |
| 179. | S | H | Cl | Me | Me | Me | Me | 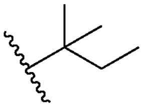 [SMILES: *C(C)(C)CC] | | |
| 180. | S | H | Cl | Me | Me | Me | Me | 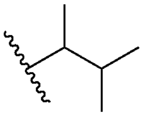 [SMILES: *C(C)C(C)C] | | |
| 181. | S | H | Cl | Me | Me | Me | Me | 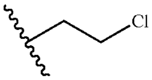 [SMILES: *CCCl] | | |
| 182. | S | H | Cl | Me | Me | Me | Me | 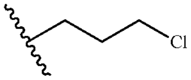 [SMILES: *CCCCl] | | |
| 183. | S | H | Cl | Me | Me | Me | Me | 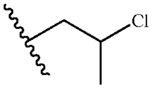 [SMILES: *CC(C)Cl] | | |
| 184. | S | H | Cl | Me | Me | Me | Me | 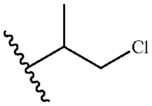 [SMILES: *C(C)CCl] | | |

TABLE 1-continued
| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 185. | S | H | Cl | Me | Me | Me | Me | 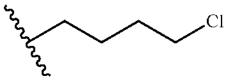 [SMILES: *CCCCCl] | | |
| 186. | S | H | Cl | Me | Me | Me | Me | 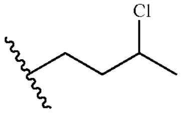 | | |
| 187. | S | H | Cl | Me | Me | Me | Me | 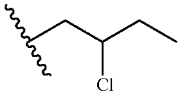 [SMILES: *CC(Cl)CC] | | |
| 188. | S | H | Cl | Me | Me | Me | Me | 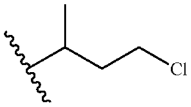 [SMILES: *C(C)CCCl] | | |
| 189. | S | H | Cl | Me | Me | Me | Me | 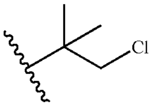 [SMILES: *C(C)(C)CCl] | | |
| 190. | S | H | Cl | Me | Me | Me | Me | 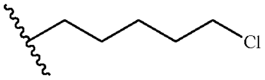 [SMILES: *CCCCCCl] | | |
| 191. | S | H | Cl | Me | Me | Me | Me | 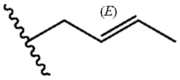 [SMILES: *C/C=C/C] | | |
| 192. | S | H | Cl | Me | Me | Me | Me | 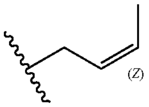 [SMILES: *C/C=C\C] | | |
| 193. | S | H | Cl | Me | Me | Me | Me | 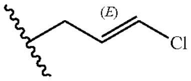 [SMILES: *C/C=C/Cl] | | |
| 194. | S | H | Cl | Me | Me | Me | Me | 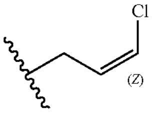 | | |
| 195. | S | H | Cl | Me | Me | Me | Me | 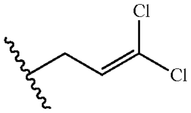 [SMILES: *CC=C(Cl)Cl] | | |
| 196. | S | H | Cl | Me | Me | Me | Me | 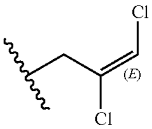 [SMILES: *C/C(Cl)=C\Cl] | | |
| 197. | S | H | Cl | Me | Me | Me | Me | 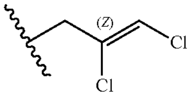 [SMILES: *C/C(Cl)=C/Cl] | | |

TABLE 1-continued

| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 198. | S | H | Cl | Me | Me | Me | Me | 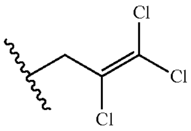 [SMILES: *CC(Cl)=C(Cl)Cl] | | |
| 199. | S | H | Cl | Me | Me | Me | Me | 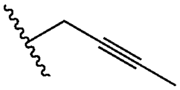 | | |
| 200. | S | H | Cl | Me | Me | Me | Me | 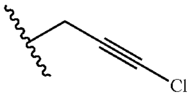 [SMILES: *CC#CCl] | | |
| 201. | S | H | Cl | Me | Me | Me | Me | 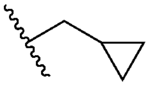 | | |
| 202. | S | H | Cl | Me | Me | Me | Me | 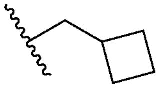 [SMILES: *CC1CCC1] | | |
| 203. | S | H | Cl | Me | Me | Me | Me | 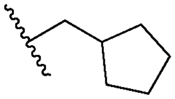 [SMILES: *CC1CCCC1] | | |
| 204. | S | H | Cl | Me | Me | Me | Me | 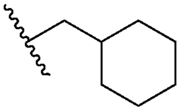 [SMILES: *CC1CCCCC1] | | |
| 205. | S | H | Cl | Me | Me | Me | Me | 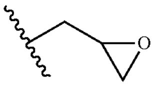 [SMILES: *CC1CO1] | | |
| 206. | S | H | Cl | Me | Me | Me | Me | 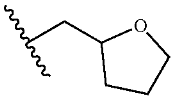 [SMILES: *CC1CCCO1] | | |
| 207. | S | F | Cl | Me | Me | H | H | Et | | |
| 208. | S | F | Cl | Me | Me | H | H | n-Pr | | |
| 209. | S | F | Cl | Me | Me | H | H | i-Pr | | |
| 210. | S | F | Cl | Me | Me | H | H | n-Bu | | |
| 211. | S | F | Cl | Me | Me | H | H | i-Bu | | |
| 212. | S | F | Cl | Me | Me | H | H | s-Bu | | |
| 213. | S | F | Cl | Me | Me | H | H | t-Bu | | |
| 214. | S | F | Cl | Me | Me | H | H | 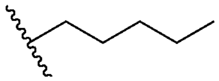 [SMILES: *CCCCC] | | |
| 215. | S | F | Cl | Me | Me | H | H | 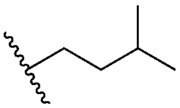 [SMILES: *CCC(C)C] | | |
| 216. | S | F | Cl | Me | Me | H | H | 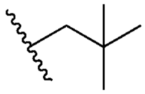 [SMILES: *CC(C)(C)C] | | |

TABLE 1-continued
| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 217. | S | F | Cl | Me | Me | H | H | 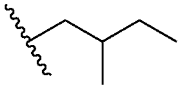 [SMILES: *CC(C)CC] | | |
| 218. | S | F | Cl | Me | Me | H | H | 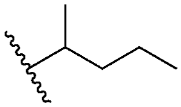 [SMILES: *C(C)CCC] | | |
| 219. | S | F | Cl | Me | Me | H | H | 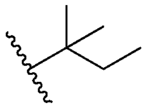 [SMILES: *C(C)(C)CC] | | |
| 220. | S | F | Cl | Me | Me | H | H | 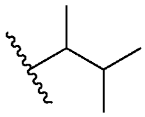 [SMILES: *C(C)C(C)C] | | |
| 221. | S | F | Cl | Me | Me | H | H | 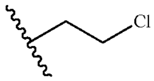 [SMILES: *CCCl] | | yellow oil |
| 222. | S | F | Cl | Me | Me | H | H | 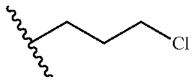 [SMILES: *CCCCl] | | colorless foam |
| 223. | S | F | Cl | Me | Me | H | H | 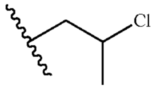 [SMILES: *CC(C)Cl] | | |
| 224. | S | F | Cl | Me | Me | H | H | 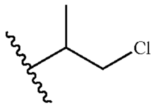 [SMILES: *C(C)CCl] | | |
| 225. | S | F | Cl | Me | Me | H | H | 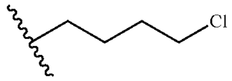 [SMILES: *CCCCCl] | | yellow oil |
| 226. | S | F | Cl | Me | Me | H | H | 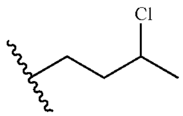 [SMILES: *CCC(C)Cl] | | |
| 227. | S | F | Cl | Me | Me | H | H | 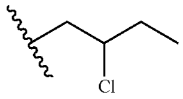 [SMILES: *CC(Cl)CC] | | |
| 228. | S | F | Cl | Me | Me | H | H | 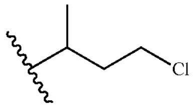 [SMILES: *C(C)CCCl] | | |
| 229. | S | F | Cl | Me | Me | H | H | 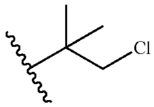 [SMILES: *C(C)(C)CCl] | | |

TABLE 1-continued
| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 230. | S | F | Cl | Me | Me | H | H | 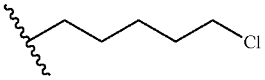 [SMILES: *CCCCCCl] | | |
| 231. | S | F | Cl | Me | Me | H | H | 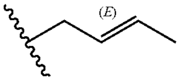 [SMILES: *C/C=C/C] | | |
| 232. | S | F | Cl | Me | Me | H | H | 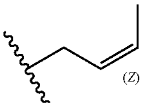 [SMILES: *C/C=C\C] | | |
| 233. | S | F | Cl | Me | Me | H | H | 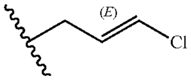 [SMILES: *C/C=C/Cl] | | |
| 234. | S | F | Cl | Me | Me | H | H | 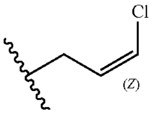 [SMILES: *C/C=C\Cl] | | |
| 235. | S | F | Cl | Me | Me | H | H | 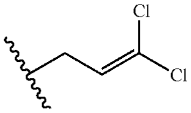 [SMILES: *CC=C(Cl)Cl] | | |
| 236. | S | F | Cl | Me | Me | H | H | 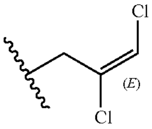 [SMILES: *C/C(Cl)=C\Cl] | | |
| 237. | S | F | Cl | Me | Me | H | H | 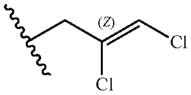 [SMILES: *C/C(Cl)=C/Cl] | | |
| 238. | S | F | Cl | Me | Me | H | H | 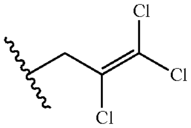 [SMILES: *CC(Cl)=C(Cl)Cl] | | |
| 239. | S | F | Cl | Me | Me | H | H | 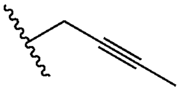 [SMILES: *CC#CC] | | |
| 240. | S | F | Cl | Me | Me | H | H | 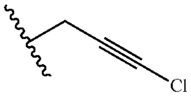 [SMILES: *CC#CCl] | | |
| 241. | S | F | Cl | Me | Me | H | H | 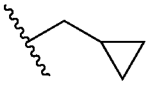 [SMILES: *CC1CC1] | | colorless foam |
| 242. | S | F | Cl | Me | Me | H | H | 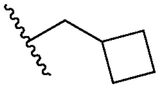 [SMILES: *CC1CCC1] | | |

TABLE 1-continued

| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 243. | S | F | Cl | Me | Me | H | H | 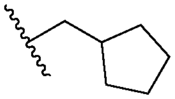 [SMILES: *CC1CCCC1] | | |
| 244. | S | F | Cl | Me | Me | H | H | 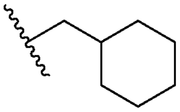 [SMILES: *CC1CCCCC1] | | |
| 245. | S | F | Cl | Me | Me | H | H | 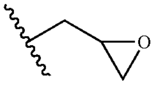 [SMILES: *CC1CO1] | | colorless foam |
| 246. | S | F | Cl | Me | Me | H | H | 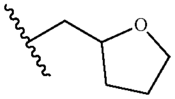 [SMILES: *CC1CCCO1] | | colorless oil |
| 247. | S | F | Cl | Me | Me | H | H | 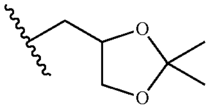 [SMILES: *CC1COC(C)(C)O1] | | colorless foam |
| 248. | S | F | Cl | Me | Me | H | Me | Et | rac. | yellow oil |
| 249. | S | F | Cl | Me | Me | H | Me | Et | R | colorless foam |
| 250. | S | F | Cl | Me | Me | H | Me | Et | S | yellow foam |
| 251. | S | F | Cl | Me | Me | H | Me | n-Pr | | |
| 252. | S | F | Cl | Me | Me | H | Me | i-Pr | | |
| 253. | S | F | Cl | Me | Me | H | Me | n-Bu | | |
| 254. | S | F | Cl | Me | Me | H | Me | i-Bu | | |
| 255. | S | F | Cl | Me | Me | H | Me | s-Bu | | |
| 256. | S | F | Cl | Me | Me | H | Me | t-Bu | | |
| 257. | S | F | Cl | Me | Me | H | Me | 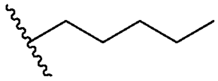 [SMILES: *CCCCC] | | |
| 258. | S | F | Cl | Me | Me | H | Me | 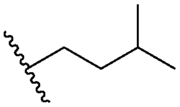 | | |
| 259. | S | F | Cl | Me | Me | H | Me | 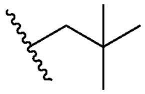 [SMILES: *CC(C)(C)C] | | |
| 260. | S | F | Cl | Me | Me | H | Me | 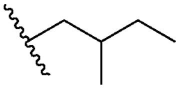 [SMILES: *CC(C)CC] | | |
| 261. | S | F | Cl | Me | Me | H | Me | 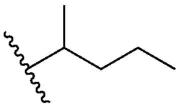 [SMILES: *C(C)CCC] | | |
| 262. | S | F | Cl | Me | Me | H | Me | 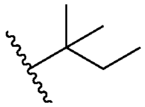 [SMILES: *C(C)(C)CC] | | |

TABLE 1-continued

| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 263. | S | F | Cl | Me | Me | H | Me | 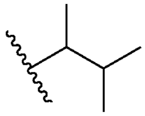 [SMILES: *C(C)C(C)C] | | |
| 264. | S | F | Cl | Me | Me | H | Me | 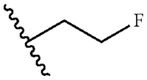 [SMILES: *CCF] | | colorless oil |
| 265. | S | F | Cl | Me | Me | H | Me | 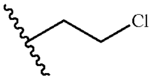 [SMILES: *CCCl] | rac. | colorless foam |
| 266. | S | F | Cl | Me | Me | H | Me | 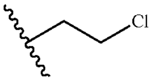 [SMILES: *CCCl] | R | colorless foam |
| 267. | S | F | Cl | Me | Me | H | Me | 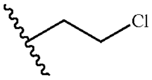 [SMILES: *CCCl] | S | colorless foam |
| 268. | S | F | Cl | Me | Me | H | Me | 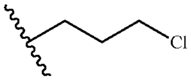 [SMILES: *CCCCl] | rac. | colorless foam |
| 269. | S | F | Cl | Me | Me | H | Me | 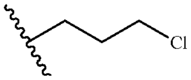 [SMILES: *CCCCl] | R | colorless foam |
| 270. | S | F | Cl | Me | Me | H | Me | 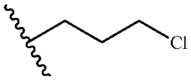 [SMILES: *CCCCl] | S | colorless foam |
| 271. | S | F | Cl | Me | Me | H | Me | 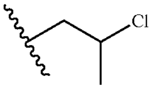 [SMILES: *CC(C)Cl] | | |
| 272. | S | F | Cl | Me | Me | H | Me | 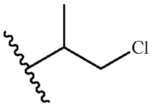 [SMILES: *C(C)CCl] | | |
| 273. | S | F | Cl | Me | Me | H | Me | 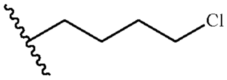 [SMILES: *CCCCCl] | | yellow oil |
| 274. | S | F | Cl | Me | Me | H | Me | 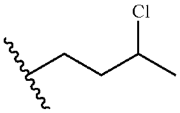 [SMILES: *CCC(C)Cl] | | |
| 275. | S | F | Cl | Me | Me | H | Me | 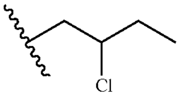 [SMILES: *CC(Cl)CC] | | |
| 276. | S | F | Cl | Me | Me | H | Me | 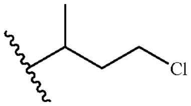 [SMILES: *C(C)CCCl] | | |

TABLE 1-continued
| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 277. | S | F | Cl | Me | Me | H | Me | 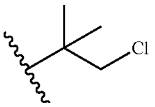 [SMILES: *C(C)(C)CCl] | | |
| 278. | S | F | Cl | Me | Me | H | Me | 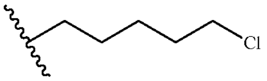 [SMILES: *CCCCCCl] | | |
| 279. | S | F | Cl | Me | Me | H | Me | 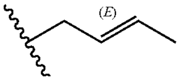 [SMILES: *C/C=C/C] | | |
| 280. | S | F | Cl | Me | Me | H | Me | 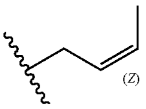 [SMILES: *C/C=C\C] | | |
| 281. | S | F | Cl | Me | Me | H | Me | 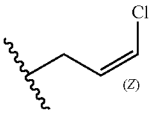 | | colorless oil |
| 282. | S | F | Cl | Me | Me | H | Me | 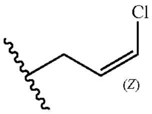 [SMILES: *C/C=C\Cl] | | |
| 283. | S | F | Cl | Me | Me | H | Me | 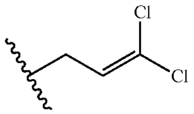 [SMILES: *CC=C(Cl)Cl] | | pale yellow oil |
| 284. | S | F | Cl | Me | Me | H | Me | 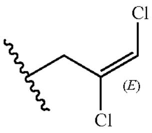 | | |
| 285. | S | F | Cl | Me | Me | H | Me | 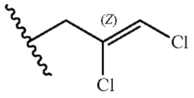 [SMILES: *C/C(Cl)=C/Cl] | | |
| 286. | S | F | Cl | Me | Me | H | Me | 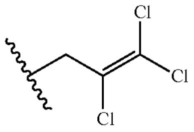 [SMILES: *CC(Cl)=C(Cl)Cl] | | |
| 287. | S | F | Cl | Me | Me | H | Me | 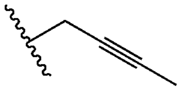 [SMILES: *CC#CC] | | yellow oil |
| 288. | S | F | Cl | Me | Me | H | Me | 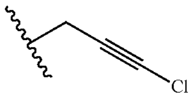 [SMILES: *CC#CCl] | | |
| 289. | S | F | Cl | Me | Me | H | Me | Bn | | yellow oil |

TABLE 1-continued

| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 290. | S | F | Cl | Me | Me | H | Me | 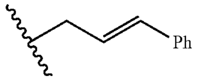 [SMILES: *C/C=C/c1ccccc1] | | colorless foam |
| 291. | S | F | Cl | Me | Me | H | Me | 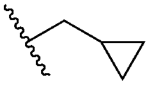 [SMILES: *CC1CC1] | | yellow oil |
| 292. | S | F | Cl | Me | Me | H | Me | 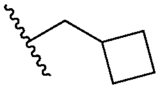 [SMILES: *CC1CCC1] | | |
| 293. | S | F | Cl | Me | Me | H | Me | 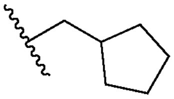 [SMILES: *CC1CCCC1] | | yellow oil |
| 294. | S | F | Cl | Me | Me | H | Me | 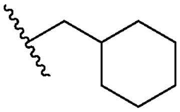 [SMILES: *CC1CCCCC1] | | |
| 295. | S | F | Cl | Me | Me | H | Me | 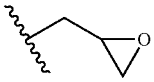 [SMILES: *CC1CO1] | | colorless foam |
| 296. | S | F | Cl | Me | Me | H | Me | 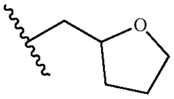 [SMILES: *CC1CCCO1] | | colorless oil |
| 297. | S | F | Cl | Me | Me | H | Me | 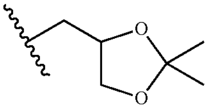 [SMILES: *CC1COC(C)(C)O1] | | colorless foam |
| 298. | S | F | Cl | Me | Me | H | Me | 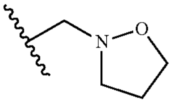 [SMILES: *CN1CCCO1] | | pale yellow oil |
| 299. | S | F | Cl | Me | Me | H | Et | Et | | yellow oil |
| 300. | S | F | Cl | Me | Me | H | Et | 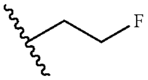 [SMILES: *CCF] | | colorless foam |
| 301. | S | F | Cl | Me | Me | H | Et | 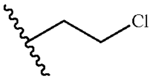 [SMILES: *CCCl] | | yellow foam |
| 302. | S | F | Cl | Me | Me | H | Et | 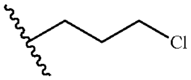 [SMILES: *CCCCl] | | yellow foam |
| 303. | S | F | Cl | Me | Me | H | Et | 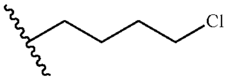 [SMILES: *CCCCCl] | | yellow oil |
| 304. | S | F | Cl | Me | Me | H | Et | 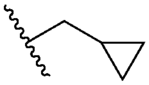 [SMILES: *CC1CC1] | | yellow oil |

TABLE 1-continued

| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 305. | S | F | Cl | Me | Me | H | i-Pr | Et | | yellow oil |
| 306. | S | F | Cl | Me | Me | Me | Me | Et | | white solid 98~100 |
| 307. | S | F | Cl | Me | Me | Me | Me | n-Pr | | |
| 308. | S | F | Cl | Me | Me | Me | Me | i-Pr | | |
| 309. | S | F | Cl | Me | Me | Me | Me | n-Bu | | |
| 310. | S | F | Cl | Me | Me | Me | Me | i-Bu | | |
| 311. | S | F | Cl | Me | Me | Me | Me | s-Bu | | |
| 312. | S | F | Cl | Me | Me | Me | Me | t-Bu | | |
| 313. | S | F | Cl | Me | Me | Me | Me | 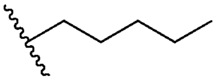 [SMILES: *CCCCC] | | |
| 314. | S | F | Cl | Me | Me | Me | Me | 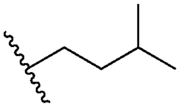 [SMILES: *CCC(C)C] | | |
| 315. | S | F | Cl | Me | Me | Me | Me | 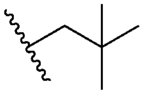 [SMILES: *CC(C)(C)C] | | |
| 316. | S | F | Cl | Me | Me | Me | Me | 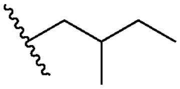 [SMILES: *CC(C)CC] | | |
| 317. | S | F | Cl | Me | Me | Me | Me | 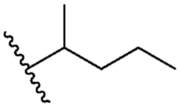 [SMILES: *C(C)CCC] | | |
| 318. | S | F | Cl | Me | Me | Me | Me | 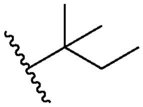 [SMILES: *C(C)(C)CC] | | |
| 319. | S | F | Cl | Me | Me | Me | Me | 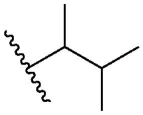 [SMILES: *C(C)C(C)C] | | |
| 320. | S | F | Cl | Me | Me | Me | Me | 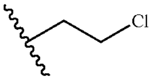 [SMILES: *CCCl] | | |
| 321. | S | F | Cl | Me | Me | Me | Me | 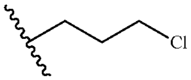 [SMILES: *CCCCl] | | |
| 322. | S | F | Cl | Me | Me | Me | Me | 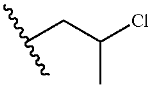 [SMILES: *CC(C)Cl] | | |
| 323. | S | F | Cl | Me | Me | Me | Me | 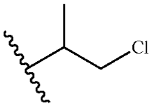 [SMILES: *C(C)CCl] | | |
| 324. | S | F | Cl | Me | Me | Me | Me | 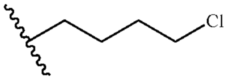 [SMILES: *CCCCCl] | | |

TABLE 1-continued
| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 325. | S | F | Cl | Me | Me | Me | Me | 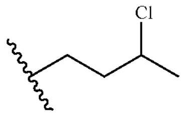 [SMILES: *CCC(C)Cl] | | |
| 326. | S | F | Cl | Me | Me | Me | Me | 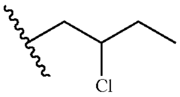 [SMILES: *CC(Cl)CC] | | |
| 327. | S | F | Cl | Me | Me | Me | Me | 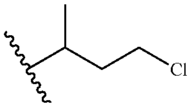 [SMILES: *C(C)CCCl] | | |
| 328. | S | F | Cl | Me | Me | Me | Me | 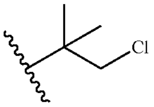 [SMILES: *C(C)(C)CCl] | | |
| 329. | S | F | Cl | Me | Me | Me | Me | 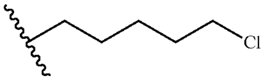 [SMILES: *CCCCCCl] | | |
| 330. | S | F | Cl | Me | Me | Me | Me | 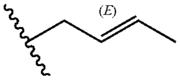 | | |
| 331. | S | F | Cl | Me | Me | Me | Me | 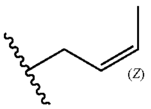 [SMILES: *C/C=C\C] | | |
| 332. | S | F | Cl | Me | Me | Me | Me | 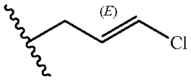 [SMILES: *C/C=C/Cl] | | |
| 333. | S | F | Cl | Me | Me | Me | Me | 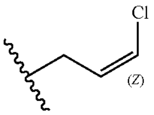 [SMILES: *C/C=C\Cl] | | |
| 334. | S | F | Cl | Me | Me | Me | Me | 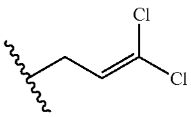 [SMILES: *CC=C(Cl)Cl] | | |
| 335. | S | F | Cl | Me | Me | Me | Me | 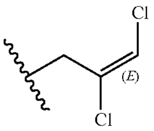 [SMILES: *C/C(Cl)=C\Cl] | | |
| 336. | S | F | Cl | Me | Me | Me | Me | 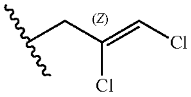 [SMILES: *C/C(Cl)=C/Cl] | | |

TABLE 1-continued

| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 337. | S | F | Cl | Me | Me | Me | Me | 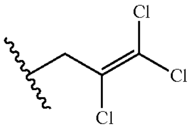 [SMILES: *CC(Cl)=C(Cl)Cl] | | |
| 338. | S | F | Cl | Me | Me | Me | Me | 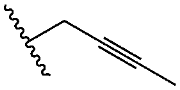 [SMILES: *CC#CC] | | |
| 339. | S | F | Cl | Me | Me | Me | Me | 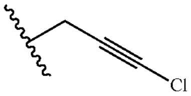 [SMILES: *CC#CCl] | | |
| 340. | S | F | Cl | Me | Me | Me | Me | 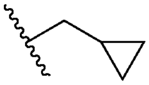 [SMILES: *CC1CC1] | | |
| 341. | S | F | Cl | Me | Me | Me | Me | 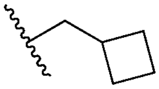 [SMILES: *CC1CCC1] | | |
| 342. | S | F | Cl | Me | Me | Me | Me | 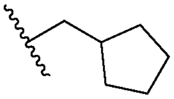 [SMILES: *CC1CCCC1] | | |
| 343. | S | F | Cl | Me | Me | Me | Me | 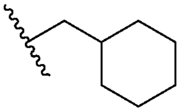 [SMILES: *CC1CCCCC1] | | |
| 344. | S | F | Cl | Me | Me | Me | Me | 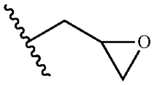 [SMILES: *CC1CO1] | | |
| 345. | S | F | Cl | Me | Me | Me | Me | 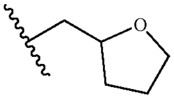 [SMILES: *CC1CCCO1] | | |
| 346. | S | F | Cl | Et | Et | H | Me | Et | | |
| 347. | S | F | Cl | Et | Et | H | Me | n-Pr | | |
| 348. | S | F | Cl | Et | Et | H | Me | i-Pr | | |
| 349. | S | F | Cl | Et | Et | H | Me | n-Bu | | |
| 350. | S | F | Cl | Et | Et | H | Me | i-Bu | | |
| 351. | S | F | Cl | Et | Et | H | Me | s-Bu | | |
| 352. | S | F | Cl | Et | Et | H | Me | t-Bu | | |
| 353. | S | F | Cl | Et | Et | H | Me | 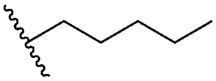 [SMILES: *CCCCC] | | |
| 354. | S | F | Cl | Et | Et | H | Me | 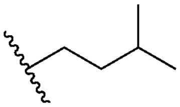 [SMILES: *CCC(C)C] | | |
| 355. | S | F | Cl | Et | Et | H | Me | 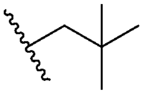 [SMILES: *CC(C)(C)C] | | |

TABLE 1-continued
| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 356. | S | F | Cl | Et | Et | H | Me | 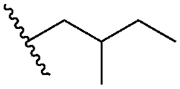 [SMILES: *CC(C)CC] | | |
| 357. | S | F | Cl | Et | Et | H | Me | 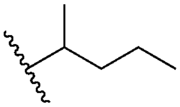 [SMILES: *C(C)CCC] | | |
| 358. | S | F | Cl | Et | Et | H | Me | 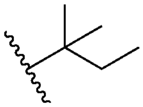 [SMILES: *C(C)(C)CC] | | |
| 359. | S | F | Cl | Et | Et | H | Me | 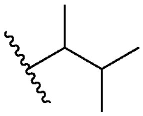 [SMILES: *C(C)C(C)C] | | |
| 360. | S | F | Cl | Et | Et | H | Me | 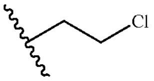 [SMILES: *CCCl] | | |
| 361. | S | F | Cl | Et | Et | H | Me | 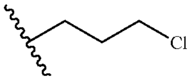 [SMILES: *CCCCl] | | |
| 362. | S | F | Cl | Et | Et | H | Me | 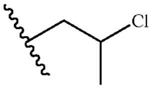 [SMILES: *CC(C)Cl] | | |
| 363. | S | F | Cl | Et | Et | H | Me | 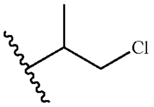 [SMILES: *C(C)CCl] | | |
| 364. | S | F | Cl | Et | Et | H | Me | 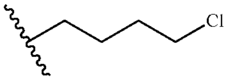 [SMILES: *CCCCCl] | | |
| 365. | S | F | Cl | Et | Et | H | Me | 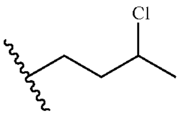 [SMILES: *CCC(C)Cl] | | |
| 366. | S | F | Cl | Et | Et | H | Me | 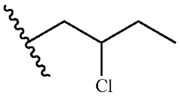 [SMILES: *CC(Cl)CC] | | |
| 367. | S | F | Cl | Et | Et | H | Me | 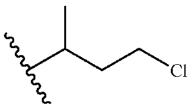 [SMILES: *C(C)CCCl] | | |
| 368. | S | F | Cl | Et | Et | H | Me | 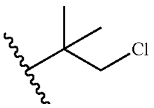 [SMILES: *C(C)(C)CCl] | | |

TABLE 1-continued
| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 369. | S | F | Cl | Et | Et | H | Me | 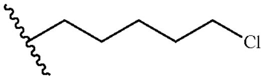 [SMILES: *CCCCCCl] | | |
| 370. | S | F | Cl | Et | Et | H | Me | 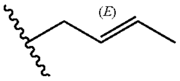 [SMILES: *C/C=C/C] | | |
| 371. | S | F | Cl | Et | Et | H | Me | 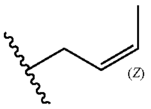 [SMILES: *C/C=C\C] | | |
| 372. | S | F | Cl | Et | Et | H | Me | 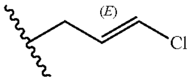 [SMILES: *C/C=C/Cl] | | |
| 373. | S | F | Cl | Et | Et | H | Me | 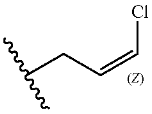 [SMILES: *C/C=C\Cl] | | |
| 374. | S | F | Cl | Et | Et | H | Me | 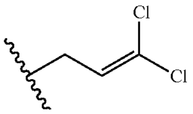 [SMILES: *CC=C(Cl)Cl] | | |
| 375. | S | F | Cl | Et | Et | H | Me | 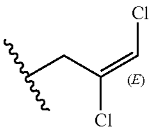 [SMILES: *C/C(Cl)=C\Cl] | | |
| 376. | S | F | Cl | Et | Et | H | Me | 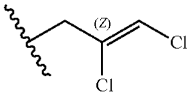 [SMILES: *C/C(Cl)=C/Cl] | | |
| 377. | S | F | Cl | Et | Et | H | Me | 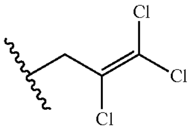 [SMILES: *CC(Cl)=C(Cl)Cl] | | |
| 378. | S | F | Cl | Et | Et | H | Me | 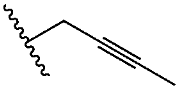 [SMILES: *CC#CC] | | |
| 379. | S | F | Cl | Et | Et | H | Me | 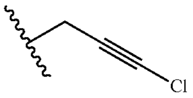 [SMILES: *CC#CCl] | | |
| 380. | S | F | Cl | Et | Et | H | Me | 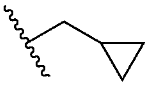 [SMILES: *CC1CC1] | | |
| 381. | S | F | Cl | Et | Et | H | Me | 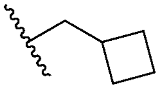 [SMILES: *CC1CCC1] | | |

TABLE 1-continued

| Compound | W | $X_1$ | $X_2$ | $R_1$ | $R_2$ | $R_3$ | $R_4$ | $R_5$ | Configuration | Melting Point/° C. |
|---|---|---|---|---|---|---|---|---|---|---|
| 382. | S | F | Cl | Et | Et | H | Me | 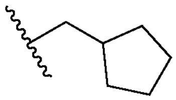 [SMILES: *CC1CCCC1] | | |
| 383. | S | F | Cl | Et | Et | H | Me | 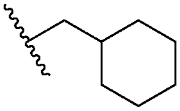 [SMILES: *CC1CCCCC1] | | |
| 384. | S | F | Cl | Et | Et | H | Me | 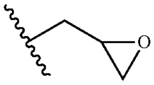 [SMILES: *CC1CO1] | | |
| 385. | S | F | Cl | Et | Et | H | Me | 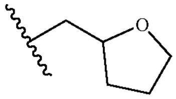 [SMILES: *CC1CCCO1] | | |

$^1H$ NMR ($CDCl_3$, 600 MHz) δ (ppm) data of part of compounds is as follows:

Compound 1 8.00 (d, 1H, J=7.2 Hz), 7.39 (d, 1H, J=8.4 Hz), 5.32 (q, 1H, J=7.2 Hz), 4.23 (q, 2H, J=7.2 Hz), 3.42 (s, 6H), 1.60 (d, 3H, J=7.2 Hz), 1.29 (t, 3H, J=7.2 Hz).

Compound 15 8.02 (d, 1H, J=7.8 Hz), 7.40 (d, 1H, J=9.0 Hz), 5.37 (q, 1H, J=7.2 Hz), 4.40-4.46 (m, 2H), 3.70 (t, 2H, J=6.0 Hz), 3.42 (2s, 6H), 1.65 (d, 3H, J=6.6 Hz).

Compound 16 8.00 (d, 1H, J=7.2 Hz), 7.41 (d, 1H, J=9.0 Hz), 5.33 (q, 1H, J=7.2 Hz), 4.35 (t, 2H, J=6.0 Hz), 3.60 (t, 2H, J=6.6 Hz), 3.43 (2s, 6H), 2.09-2.17 (m, 2H), 1.62 (d, 3H, J=6.6 Hz).

Compound 19 8.01 (d, 1H, J=7.2 Hz), 7.40 (d, 1H, J=9.0 Hz), 5.32 (q, 1H, J=6.6 Hz), 4.22 (t, 2H, J=6.0 Hz), 3.56 (t, 2H, J=6.0 Hz), 3.42 (2s, 6H), 1.83-1.85 (m, 4H), 1.62 (d, 3H, J=6.0 Hz).

Compound 33 8.01 (d, 1H, J=7.8 Hz), 7.40 (d, 1H, J=9.6 Hz), 5.36 (q, 1H, J=7.2 Hz), 4.74 (dq, 2H, J=15.0 Hz, J=2.4 Hz), 3.43 (2s, 6H), 1.86 (t, 3H, J=2.4 Hz), 1.63 (d, 3H, J=7.2 Hz).

Compound 35 8.02 (d, 1H, J=7.2 Hz), 7.40 (d, 1H, J=9.6 Hz), 5.34 (q, 1H, J=6.6 Hz), 4.01 (m, 2H), 3.43 (2s, 6H), 1.62 (d, 3H, J=6.6 Hz), 1.11-1.18 (m, 1H), 0.55-0.59 (m, 2H), 0.27-0.30 (m, 2H).

Compound 37 8.01 (d, 1H, J=7.2 Hz), 7.40 (d, 1H, J=9.0 Hz), 5.33 (q, 1H, J=6.6 Hz), 4.03-4.10 (m, 2H), 3.42 (2s, 6H), 2.18-2.26 (m, 1H), 1.71-1.77 (m, 2H), 1.61 (d, 3H, J=6.6 Hz), 1.50-1.61 (m, 4H), 1.20-1.25 (m, 2H).

Compound 41 7.99 (d, 1H, J=8.4 Hz), 7.40 (d, 1H, J=9.0 Hz), 5.19 (dd, 1H, J=4.8 Hz, J=7.2 Hz), 4.20-4.28 (m, 2H), 3.43 (2s, 6H), 1.96-2.07 (m, 2H), 1.29 (t, 3H, J=7.2 Hz), 1.06 (t, 3H, J=7.2 Hz).

Compound 42 7.97 (d, 1H, J=7.8 Hz), 7.40 (d, 1H, J=9.0 Hz), 5.09 (d, 1H, J=4.2 Hz), 4.20-4.28 (m, 2H), 3.43 (2s, 6H), 2.34-2.39 (m, 1H), 1.29 (t, 3H, J=7.2 Hz), 1.08 (d, 3H, J=6.6 Hz), 1.06 (d, 3H, J=6.6 Hz).

Compound 97 7.95 (d, 1H, J=3.0 Hz), 7.63 (d, 1H, J=8.4 Hz), 7.39 (dd, 1H, J=2.4 Hz, J=8.4 Hz), 4.91 (s, 2H), 4.45 (t, 2H, J=6.0 Hz), 3.78 (s, 6H), 3.71 (t, 2H, J=6.0 Hz).

Compound 117 7.94 (d, 1H, J=2.4 Hz), 7.62 (d, 1H, J=8.4 Hz), 7.38 (dd, 1H, J=3.0 Hz, J=8.4 Hz), 4.87 (s, 2H), 4.03 (d, 2H, J=7.2 Hz), 3.78 (s, 6H), 1.15 (m, 1H), 0.58 (m, 2H), 0.30 (m, 2H).

Compound 121 7.94 (d, 1H, J=3.0 Hz), 7.62 (d, 1H, J=7.8 Hz), 7.39 (dd, 1H, J=3.0 Hz, J=7.8 Hz), 4.91 (s, 2H), 4.53 (dd, 1H, J=2.4 Hz, J=12.6 Hz), 4.05 (dd, J=6.6 Hz, J=12.0 Hz), 3.78 (s, 6H), 3.23 (ddd, 1H, J=3.0 Hz, J=4.2 Hz, J=9.6 Hz), 2.86 (t, 1H, J=4.2 Hz), 2.66 (dd, 1H, J=2.4 Hz, J=4.8 Hz).

Compound 123 7.96 (d, 1H, J=3.0 Hz), 7.62 (d, 1H, J=7.8 Hz), 7.39 (dd, 1H, J=2.4 Hz, J=8.4 Hz), 4.89 (2d, 2H, J=15.6 Hz), 4.31-4.36 (m, 2H), 4.17-4.20 (m, 1H), 4.06-4.08 (m, 1H), 3.78 (s, 6H), 3.76-3.78 (m, 1H), 1.42 (s, 3H), 1.35 (s, 3H).

Compound 138 7.91 (d, 1H, J=2.4 Hz), 7.61 (d, 1H, J=7.8 Hz), 7.37 (dd, 1H, J=3.0 Hz, J=8.4 Hz), 5.38 (q, 1H, J=7.2 Hz), 4.38-4.47 (m, 2H), 3.78 (s, 6H), 3.71 (t, 2H, J=6.0 Hz), 1.65 (d, 3H, J=7.2 Hz).

Compound 139 7.91 (d, 1H, J=2.4 Hz), 7.61 (d, 1H, J=7.8 Hz), 7.37 (dd, 1H, J=3.0 Hz, J=8.4 Hz), 5.38 (q, 1H, J=7.2 Hz), 4.38-4.47 (m, 2H), 3.78 (s, 6H), 3.70 (t, 2H, J=6.0 Hz), 1.65 (d, 3H, J=7.2 Hz).

Compound 140 7.91 (d, 1H, J=2.4 Hz), 7.61 (d, 1H, J=7.8 Hz), 7.37 (dd, 1H, J=3.0 Hz, J=8.4 Hz), 5.38 (q, 1H, J=7.2 Hz), 4.38-4.47 (m, 2H), 3.78 (s, 6H), 3.70 (t, 2H, J=6.0 Hz), 1.65 (d, 3H, J=7.2 Hz).

Compound 152 7.88 (d, 1H, J=3.0 Hz), 7.62 (d, 1H, J=8.4 Hz), 7.37 (dd, 1H, J=3.0 Hz, J=8.4 Hz), 6.37 (ddt, 1H, J=6.6 Hz, J=14.4 Hz, J=1.2 Hz), 6.05 (dq, 1H, J=13.8 Hz, J=6.6 Hz), 5.34 (q, 1H, J=6.6 Hz), 4.65 (ddd, 2H, J=13.2 Hz, J=6.6 Hz, 1.2 Hz), 3.79 (s, 6H), 1.62 (d, 3H, J=6.6 Hz).

Compound 154 7.88 (d, 1H, J=2.4 Hz), 7.62 (d, 1H, J=8.4 Hz), 7.37 (dd, 1H, J=3.0 Hz, J=8.4 Hz), 6.07 (t, 1H, J=7.2 Hz), 5.35 (q, 1H, J=7.2 Hz), 4.77 (d, 2H, J=7.2 Hz), 3.78 (s, 6H), 1.63 (d, 3H, J=7.2 Hz).

Compound 160 7.90 (d, 1H, J=2.4 Hz), 7.61 (d, 1H, J=8.4 Hz), 7.36 (dd, 1H, J=2.4 Hz, J=8.4 Hz), 5.36 (q, 1H, J=7.2 Hz), 4.01 (ddd, 2H, J=7.8 Hz, J=11.4 Hz, J=19.2 Hz), 3.78 (s, 6H), 1.63 (d, 3H, J=7.8 Hz), 1.11-1.18 (m, 1H), 0.55-0.59 (m, 2H), 0.27-0.30 (m, 2H).

Compound 164 7.91 (dd, 1H, J=1.2 Hz, J=2.4 Hz), 7.61 (d, 1H, J=8.4 Hz), 7.36 (dd, 1H, J=2.4 Hz, J=7.8 Hz), 5.36 (dq, 1H, J=1.2 Hz, J=7.2 Hz), 4.50 (ddd, J=3.0 Hz, J=4.8 Hz, J=12.0 Hz), 4.04 (ddd, 1H, J=5.4 Hz, J=12.0 Hz, J=27.0 Hz), 3.78 (s, 6H), 3.74-3.78 (m, 1H), 3.19-3.25 (m, 1H), 2.84 (dt, J=7.2 Hz, J=4.2 Hz), 2.65 (ddd, J=3.0 Hz, J=4.8 Hz, J=22.2 Hz), 1.65 (d, 3H, J=6.6 Hz).

Compound 166 7.92 (dd, 1H, J=3.0 Hz, J=22.8 Hz), 7.61 (d, 1H, J=9.0 Hz), 7.37 (dd, 1H, J=2.4 Hz, J=8.4 Hz), 5.35-5.41 (m, 1H), 4.31-4.35 (m, 1H), 4.19-4.27 (m, 1H), 4.14-4.35 (m, 1H), 4.02-4.07 (m, 1H), 3.78 (s, 6H), 3.75-3.79 (m, 1H), 1.64 (d, 3H, J=7.2 Hz), 1.41 (d, 3H, J=6.0 Hz), 1.33 (d, 3H, J=10.2 Hz).

Compound 221 8.07 (d, 1H, J=7.8 Hz), 7.43 (d, 1H, J=9.0 Hz), 4.90 (s, 2H), 4.46 (t, 2H, J=6.0 Hz), 3.78 (s, 6H), 3.71 (t, 2H, J=6.0 Hz).

Compound 222 8.05 (d, 1H, J=7.8 Hz), 7.43 (d, 1H, J=9.0 Hz), 4.85 (s, 2H), 4.37 (t, 2H, J=6.0 Hz), 3.78 (s, 6H), 3.61 (t, 2H, J=6.0 Hz), 2.14 (pent, 2H, J=6.0 Hz).

Compound 225 8.05 (d, 1H, J=7.8 Hz), 7.43 (d, 1H, J=8.4 Hz), 4.85 (s, 2H), 4.23-4.26 (m, 2H), 3.78 (s, 6H), 3.55-3.59 (m, 2H), 1.82-1.87 (m, 4H).

Compound 241 8.06 (d, 1H, J=7.2 Hz), 7.42 (d, 1H, J=9.0 Hz), 4.86 (s, 2H), 4.03 (d, 2H, J=6.6 Hz), 3.78 (s, 6H), 1.16-1.18 (m, 1H), 0.58-0.61 (m, 2H), 0.29-0.31 (m, 2H).

Compound 245 8.07 (d, 1H, J=7.8 Hz), 7.43 (d, 1H, J=9.6 Hz), 4.90 (s, 2H), 4.55 (dd, 1H, J=2.4 Hz, J=12.0 Hz), 4.04 (dd, 1H, J=6.0 Hz, J=12.0 Hz), 3.78 (s, 6H), 3.23-3.25 (m, 1H), 2.86-2.88 (m, 1H), 2.66-2.68 (m, 1H).

Compound 246 8.07 (d, 1H, J=7.2 Hz), 7.42 (d, 1H, J=9.0 Hz), 4.89 (s, 2H), 4.25-4.30 (m, 1H), 4.10-4.16 (m, 2H), 3.85-3.90 (m, 1H), 3.78 (s, 6H), 3.77-3.81 (m, 1H), 1.99-2.04 (m, 1H), 1.86-1.95 (m, 2H), 1.57-1.64 (m, 1H).

Compound 247 8.09 (d, 1H, J=7.2 Hz), 7.42 (d, 1H, J=9.0 Hz), 4.89 (2d, 2H, J=16.2 Hz), 4.32-4.37 (m, 2H), 4.16-4.20 (m, 1H), 3.78 (s, 6H), 3.76-3.78 (m, 1H), 1.42 (s, 3H), 1.35 (s, 3H).

Compound 248 8.01 (d, 1H, J=7.2 Hz), 7.41 (d, 1H, J=9.0 Hz), 5.32 (q, 1H, J=7.2 Hz), 4.24 (q, 2H, J=7.2 Hz), 3.78 (s, 6H), 1.61 (d, 3H, J=7.2 Hz), 1.26 (t, 3H, J=7.2 Hz).

Compound 249 8.02 (d, 1H, J=8.4 Hz), 7.41 (d, 1H, J=9.0 Hz), 5.32 (q, 1H, J=7.2 Hz), 4.30 (q, 2H, J=7.2 Hz), 3.78 (s, 6H), 1.61 (d, 3H, J=6.6 Hz), 1.29 (t, 3H, J=7.2 Hz).

Compound 250 8.02 (d, 1H, J=7.8 Hz), 7.41 (d, 1H, J=9.0 Hz), 5.32 (q, 1H, J=7.2 Hz), 4.23 (q, 2H, J=7.2 Hz), 3.78 (s, 6H), 1.61 (d, 3H, J=6.6 Hz), 1.29 (t, 3H, J=7.2 Hz).

Compound 264 8.02 (d, 1H, J=7.8 Hz), 7.42 (d, 1H, J=9.0 Hz), 5.38 (q, 1H, J=7.2 Hz), 4.63-4.69 (m, 1H), 4.55-4.61 (m, 1H), 4.36-4.49 (m, 2H), 3.78 (2s, 6H), 1.65 (d, 3H, J=7.2 Hz).

Compound 265 8.04 (d, 1H, J=7.8 Hz), 7.42 (d, 1H, J=9.0 Hz), 5.37 (q, 1H, J=7.2 Hz), 4.39-4.48 (m, 2H), 3.78 (2s, 6H), 3.71 (t, 2H, J=6.0 Hz), 1.65 (d, 3H, J=7.2 Hz).

Compound 266 8.03 (d, 1H, J=7.2 Hz), 7.42 (d, 1H, J=9.0 Hz), 5.37 (q, 1H, J=7.2 Hz), 4.39-4.48 (m, 2H), 3.78 (2s, 6H), 3.70 (t, 2H, J=6.0 Hz), 1.65 (d, 3H, J=7.8 Hz).

Compound 267 8.03 (d, 1H, J=7.8 Hz), 7.42 (d, 1H, J=9.6 Hz), 5.37 (q, 1H, J=7.2 Hz), 4.40-4.47 (m, 2H), 3.78 (2s, 6H), 3.70 (t, 2H, J=5.4 Hz), 1.65 (d, 3H, J=7.2 Hz).

Compound 268 8.02 (d, 1H, J=7.8 Hz), 7.42 (d, 1H, J=8.4 Hz), 5.33 (q, 1H, J=7.2 Hz), 4.35 (t, 2H, J=6.0 Hz), 3.78 (2s, 6H), 3.60 (t, 2H, J=6.0 Hz), 2.09-2.17 (m, 2H), 1.62 (d, 3H, J=6.6 Hz).

Compound 269 8.01 (d, 1H, J=7.2 Hz), 7.42 (d, 1H, J=9.0 Hz), 5.33 (q, 1H, J=7.2 Hz), 4.35 (t, 2H, J=6.0 Hz), 3.78 (2s, 6H), 3.60 (t, 2H, J=6.0 Hz), 2.09-2.17 (m, 2H), 1.62 (d, 3H, J=6.6 Hz).

Compound 270 8.01 (d, 1H, J=7.2 Hz), 7.42 (d, 1H, J=9.0 Hz), 5.33 (q, 1H, J=7.2 Hz), 4.35 (t, 2H, J=6.0 Hz), 3.78 (2s, 6H), 3.60 (t, 2H, J=6.0 Hz), 2.09-2.17 (m, 2H), 1.62 (d, 3H, J=6.6 Hz).

Compound 273 8.02 (d, 1H, J=7.8 Hz), 7.42 (d, 1H, J=9.0 Hz), 5.32 (q, 1H, J=7.2 Hz), 4.22 (t, 2H, J=6.0 Hz), 3.78 (2s, 6H), 3.56 (t, 2H, J=6.0 Hz), 1.83-1.85 (m, 4H), 1.62 (d, 3H, J=6.0 Hz).

Compound 281 8.01 (d, 1H, J=7.8 Hz), 7.42 (d, 1H, J=9.0 Hz), 6.36 (dt, 1H, J=13.2 Hz, J=1.2 Hz), 6.05 (q, 1H, J=6.6 Hz), 5.33 (q, 1H, J=7.2 Hz), 4.65 (dt, 2H, J=13.2 Hz, 1.2 Hz), 3.79 (s, 6H), 1.62 (d, 3H, J=7.2 Hz).

Compound 283 8.01 (d, 1H, J=7.2 Hz), 7.42 (d, 1H, J=8.4 Hz), 6.06 (t, 1H, J=6.6 Hz), 5.34 (q, 1H, J=7.2 Hz), 4.77 (dd, 2H, J=6.6 Hz, 1.2 Hz), 3.78 (s, 6H), 1.62 (d, 3H, J=7.2 Hz).

Compound 287 8.03 (d, 1H, J=7.2 Hz), 7.41 (d, 1H, J=9.0 Hz), 5.37 (q, 1H, J=7.2 Hz), 4.74 (dq, 2H, J=15.0 Hz, J=2.4 Hz), 3.78 (2s, 6H), 1.86 (t, 3H, J=2.4 Hz), 1.63 (d, 3H, J=7.2 Hz).

Compound 289 7.97 (d, 1H, J=8.4 Hz), 7.40 (d, 1H, J=9.0 Hz), 7.31-7.37 (m, 5H), 5.39 (q, 2H, J=7.2 Hz), 5.21 (2d, 2H, J=12.6 Hz), 3.78 (s, 6H), 1.62 (d, 3H, J=7.2 Hz).

Compound 290 8.02 (d, 1H, J=7.8 Hz), 7.38-7.41 (m, 3H), 7.31-7.34 (m, 2H), 7.26-7.28 (m, 1H), 6.67 (d, 1H, J=15.6 Hz), 6.27 (dt, 1H, J=15.6 Hz, J=6.6 Hz), 5.37 (q, 1H, J=7.2 Hz), 4.83 (ddq, 2H, J=1.2 Hz, J=12.0 Hz, J=6.6 Hz), 3.77 (s, 3H), 3.76 (s, 3H), 1.64 (d, 3H, J=6.6 Hz).

Compound 291 8.03 (d, 1H, J=7.2 Hz), 7.41 (d, 1H, J=10.2 Hz), 5.34 (q, 1H, J=7.2 Hz), 4.01 (m, 2H), 3.78 (2s, 6H), 1.63 (d, 3H, J=7.2 Hz), 1.11-1.18 (m, 1H), 0.56-0.58 (m, 2H), 0.28-0.30 (m, 2H).

Compound 293 8.02 (d, 1H, J=7.8 Hz), 7.41 (d, 1H, J=9.0 Hz), 5.34 (q, 1H, J=7.2 Hz), 4.03-4.10 (m, 2H), 3.78 (2s, 6H), 2.18-2.26 (m, 1H), 1.71-1.76 (m, 2H), 1.62 (d, 3H, J=7.2 Hz), 1.50-1.61 (m, 4H), 1.20-1.25 (m, 2H).

Compound 295 8.03 (d, 1H, J=7.2 Hz), 7.41 (d, 1H, J=9.6 Hz), 5.38 (q, 1H, J=7.2 Hz), 4.51 (ddd, 1H, J=3.6 Hz, J=6.0 Hz, J=12.6 Hz), 4.03 (ddd, 1H, J=6.0 Hz, J=12.6 Hz, J=29.4 Hz), 3.78 (2s, 6H), 3.19-3.25 (m, 1H), 2.85 (dt, 1H, J=7.8 Hz, J=4.2 Hz), 2.66 (ddd, 1H, J=3.0 Hz, J=4.8 Hz, J=22.2 Hz), 1.64 (dd, 3H, J=1.2 Hz, J=7.2 Hz), 1.11-1.18 (m, 1H), 0.56-0.58 (m, 2H), 0.28-0.30 (m, 2H).

Compound 296 8.04 (d, 1H, J=7.2 Hz), 7.41 (d, 1H, J=9.0 Hz), 5.37 (dq, 1H, J=9.6 Hz, J=7.2 Hz), 4.24 (q, 1H, J=6.6 Hz), 4.10-4.16 (m, 3H), 3.83-3.87 (m, 1H), 3.78 (2s, 6H), 3.75-3.79 (m, 1H), 1.96-2.03 (m, 1H), 1.86-1.94 (m, 2H), 1.63 (dd, 3H, J=2.4 Hz, J=7.2 Hz).

Compound 297 8.05 (d, 1H, J=7.2 Hz), 7.41 (d, 1H, J=9.0 Hz), 5.37 (dq, 1H, J=6.6 Hz, J=13.8 Hz), 4.31-4.36 (m, 1H), 4.18-4.28 (m, 1H), 4.10-4.36 (m, 1H), 4.02-4.07 (m, 1H), 3.78 (s, 6H), 3.74-3.79 (m, 1H), 1.63 (d, 3H, J=6.6 Hz), 1.41 (d, 3H, J=6.0 Hz), 1.33 (d, 3H, J=12.6 Hz).

Compound 298 8.05 (d, J=7.8 Hz, 1H), 7.36 (d, J=9.1 Hz, 1H), 5.66 (q, J=6.9 Hz, 1H), 4.13-4.07 (m, 2H), 4.02 (q, J=7.7 Hz, 1H), 3.98-3.92 (m, 1H), 3.76 (s, 3H), 3.75 (s, 3H), 1.58 (d, J=6.9 Hz, 3H), 1.25-1.22 (m, 2H).

Compound 299 8.00 (d, 1H, J=7.8 Hz), 7.41 (d, 1H, J=9.0 Hz), 5.20 (dd, 1H, J=4.8 Hz, J=7.2 Hz), 4.21-4.27 (m, 2H), 3.78 (2s, 6H), 1.96-2.03 (m, 2H), 1.29 (t, 3H, J=7.2 Hz), 1.07 (t, 3H, J=7.2 Hz).

Compound 300 8.00 (d, 1H, J=7.2 Hz), 7.42 (d, 1H, J=9.6 Hz), 5.25 (dd, 1H, J=4.8 Hz, J=7.8 Hz), 4.63-4.68 (m, 1H), 4.55-4.61 (m, 1H), 4.35-4.50 (m, 2H), 3.78 (2s, 6H), 2.00-2.08 (m, 2H), 1.08 (t, 3H, J=7.8 Hz).

Compound 301 8.01 (d, 1H, J=7.8 Hz), 7.42 (d, 1H, J=9.0 Hz), 5.25 (dd, 1H, J=4.8 Hz, J=7.8 Hz), 4.44-4.48 (m, 1H), 4.38-4.42 (m, 1H), 3.78 (2s, 6H), 3.70 (t, 2H, J=5.4 Hz), 1.99-2.08 (m, 2H), 1.09 (t, 3H, J=7.2 Hz).

Compound 302 8.00 (d, 1H, J=7.8 Hz), 7.42 (d, 1H, J=9.0 Hz), 5.20 (dd, 1H, J=4.8 Hz, J=7.2 Hz), 4.35 (t, 2H, J=6.0

Hz), 3.78 (2s, 6H), 3.60 (t, 2H, J=6.0 Hz), 2.08-2.17 (m, 2H), 1.97-2.03 (m, 2H), 1.07 (t, 3H, J=7.2 Hz).

Compound 303 8.00 (d, 1H, J=8.4 Hz), 7.42 (d, 1H, J=9.0 Hz), 5.19 (dd, 1H, J=4.8 Hz, J=6.6 Hz), 4.22 (t, 2H, J=6.0 Hz), 3.78 (2s, 6H), 3.56 (t, 2H, J=6.0 Hz), 1.97-2.04 (m, 2H), 1.82-1.85 (m, 4H), 1.07 (t, 3H, J=7.2 Hz).

Compound 304 8.01 (d, 1H, J=8.4 Hz), 7.41 (d, 1H, J=9.0 Hz), 5.22 (dd, 1H, J=6.0 Hz, J=7.2 Hz), 4.22 (dq, 2H, J=7.8 Hz, J=10.8 Hz), 3.78 (2s, 6H), 1.97-2.07 (m, 2H), 1.11-1.17 (m, 1H), 1.08 (t, 3H, J=7.2 Hz), 0.55-0.59 (m, 2H), 0.26-0.31 (m, 2H).

Compound 305 7.99 (d, 1H, J=7.2 Hz), 7.42 (d, 1H, J=9.6 Hz), 5.09 (d, 1H, J=4.2 Hz), 4.20-4.28 (m, 2H), 3.78 (2s, 6H), 2.34-2.39 (m, 1H), 1.29 (t, 3H, J=7.2 Hz), 1.08 (d, 3H, J=6.6 Hz), 1.06 (d, 3H, J=6.6 Hz).

Compound 306 7.91 (d, 1H, J=7.8 Hz), 7.39 (d, 1H, J=9.0 Hz), 4.22 (q, 2H, J=7.2 Hz), 3.78 (s, 6H), 1.68 (s, 6H), 1.06 (t, 3H, J=7.2 Hz).

BIOMETRIC TEST EMBODIMENTS

Embodiment 15 Determination of Herbicidal Activity

Seeds of broadleaf weeds (zinnia and piemarker) or grassy weeds (green bristlegrass and barnyard grass) were respectively sown in a paper cup having a diameter of 7 cm and containing nutrient soil; after sowing, the seeds were covered with 1 cm of soil; the soil was pressed and watered, and then the seeds were cultivated in a greenhouse according to a conventional method; and stems and leaves were sprayed after 2-3 leaf stage of the weeds.

After the original medicinal acetone was dissolved, the test requires to use 1‰ of Tween 80 to stand in running water to prepare the solution to be tested with a required concentration. According to the design dose of the test, spray treatment was carried out on a track-type crop sprayer (designed and produced by British Engineer Research Ltd.) (spray pressure is 1.95 kg/cm$^2$, spray volume is 500 L/hm$^2$ and track speed is 1.48 km/h). The test was repeated for three times. The test material was treated and then placed in an operation hall. The medicinal liquid was naturally dried in the shade, and then was placed in a greenhouse and managed according to the conventional method. The response of the weeds to the drug was observed and recorded. After treatment, the control effects of the test drug on the weeds were visually inspected regularly, expressed by 0-100%. “0” represents no control effect and “100%” represents complete killing.

The test results show that the compounds of the formula I generally have high control effects on various weeds. Part of the test compounds, such as compounds 221, 222, 225, 241, 245, 246, 247, 248, 249, 250, 264, 265, 266, 267, 268, 269, 270, 273, 281, 283, 287, 289, 290, 291, 293, 295, 296, 297, 298, 299, 300, 301, 302, 303, 304 and 305, have good control effects on zinnia at the application dose of 150 g a.i./hm$^2$, and the control effects are 100%.

The test results show that the compounds of the formula I generally have high control effects on various weeds. Part of the test compounds, such as compounds 138, 160, 221, 222, 225, 241, 245, 246, 247, 248, 249, 250, 264, 265, 266, 267, 268, 269, 270, 273, 281, 283, 287, 289, 290, 291, 293, 295, 296, 297, 298, 300, 301, 302, 303, 304, 305 and 306, have good control effects on piemarker at the application dose of 150 g a.i./hm$^2$, and the control effects are 100%.

The test results show that the compounds of the formula I generally have high control effects on various weeds. Part of the test compounds, such as compounds 117, 221, 222, 225, 241, 245, 246, 247, 248, 250, 264, 268, 273, 281, 283, 287, 291, 295, 296, 297 and 298, have good control effects on green bristlegrass at the application dose of 150 g a.i./hm$^2$, and the control effects are not less than 80%.

The test results show that the compounds of the formula I generally have high control effects on various weeds. Part of the test compounds, such as compounds 221, 222, 225, 241, 245, 246, 247, 248, 249, 250, 264, 265, 266, 267, 268, 269, 270, 273, 281, 283, 287, 291, 293, 295, 296, 297, 298, 301 and 306, have good control effects on barnyard grass at the application dose of 150 g a.i./hm$^2$, and the control effects are not less than 90%.

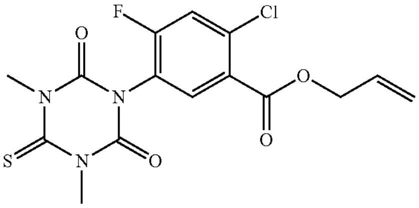

$KC_1$

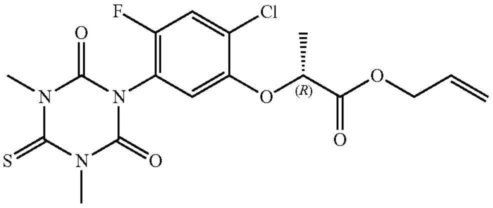

$KC_2$

According to the above test methods, part of compounds of formula I and the following compound $KC_1$ specifically disclosed in patent CN1341105A (compound No. 30 in Table 3 of the patent description) are selected to conduct parallel tests for herbicidal activity under the application doses of 37.5 g a.i./hm$^2$ and 9.375 g a.i./hm$^2$. The results are shown in Table 2.

TABLE 2

Herbicidal Activity of Part of Compounds of Formula (I) (after emergence, control effect %)

| Compound | Dose g a.i./hm$^2$ | Zinnia | Piemarker | Green Bristlegrass | Barnyard Grass |
|---|---|---|---|---|---|
| 248 (rac.) | 37.5 | 90 | 100 | 95 | 100 |
| | 9.375 | 60 | 90 | 70 | 95 |
| 249 (R) | 37.5 | 70 | 100 | 80 | 55 |
| | 9.375 | 50 | 65 | 35 | 30 |
| 250 (S) | 37.5 | 98 | 100 | 100 | 90 |
| | 9.375 | 70 | 98 | 100 | 50 |
| $KC_1$ | 37.5 | 60 | 100 | 25 | 25 |
| | 9.375 | 50 | 55 | 10 | 0 |

According to the above test methods, part of compounds of formula I and the following compound $KC_1$ (compound No. 30 in Table 3 of the patent description) and $KC_2$ (R body, compound No. 12 in Table 3 of the patent description) specifically disclosed in patent CN1341105A are selected to conduct parallel tests for herbicidal activity of zinnia, piemarker, green bristlegrass and barnyard grass. Results are shown in Table 3 to Table 6.

TABLE 3

Parallel Comparison of Herbicidal Activity of Part of Compounds of Formula (I) for Zinnia(after emergence, control effect %)

| Compound | | 221 | 222 | 225 | 241 | 245 | 246 | 247 | 248 | 250 | 264 | 266 | 267 | 268 | 269 |
|---|---|---|---|---|---|---|---|---|---|---|---|---|---|---|---|
| Dose | 9.375 | 100 | 100 | 100 | 100 | 100 | 95 | 100 | 100 | 95 | 100 | 100 | 100 | 100 | 95 |
| g a.i./$hm^2$ | 2.34 | 85 | 100 | 95 | 100 | 95 | 95 | 100 | 95 | 80 | 90 | 85 | 85 | 85 | 80 |
| Compound | | 270 | 281 | 283 | 287 | 291 | 293 | 295 | 296 | 297 | 298 | 302 | 303 | 304 | $KC_1$ |
| Dose | 9.375 | 100 | 100 | 100 | 100 | 100 | 100 | 100 | 100 | 100 | 100 | 100 | 100 | 100 | 50 |
| g a.i./$hm^2$ | 2.34 | 90 | 90 | 100 | 80 | 85 | 90 | 90 | 90 | 95 | 90 | 90 | 85 | 80 | / |

Note:
"/" indicates no test.

TABLE 4

Parallel Comparison of Herbicidal Activity of Part of Compounds of Formula (I) for Piemarker(after emergence, control effect %)

| Compound | | 221 | 225 | 241 | 248 | 250 | 265 | 267 | 270 | 273 | 291 | 293 | 297 | 298 | 299 | $KC_1$ |
|---|---|---|---|---|---|---|---|---|---|---|---|---|---|---|---|---|
| Dose | 9.375 | 100 | 100 | 100 | 100 | 100 | 100 | 100 | 100 | 100 | 100 | 100 | 100 | 100 | 100 | 55 |
| g a.i./$hm^2$ | 2.34 | 85 | 85 | 98 | 90 | 85 | 90 | 90 | 85 | 90 | 85 | 85 | 85 | 85 | 85 | / |

Note:
"/" indicates no test.

TABLE 5

Parallel Comparison of Herbicidal Activity of Part of Compounds of Formula (I) for Green Bristlegrass (after emergence, control effect %)

| Compound | | 221 | 222 | 225 | 241 | 245 | 246 | 247 | 248 | 250 | 281 | 283 | 287 | $KC_1$ | $KC_2$ |
|---|---|---|---|---|---|---|---|---|---|---|---|---|---|---|---|
| Dose | 37.5 | 90 | 90 | 90 | 100 | 90 | 90 | 90 | 85 | 90 | 90 | 85 | 70 | 25 | 50 |
| g a.i./$hm^2$ | 9.375 | 80 | 60 | 80 | 80 | 70 | 80 | 60 | 60 | 70 | 60 | 50 | 50 | 10 | 20 |

TABLE 6

Parallel Comparison of Herbicidal Activity of Part of Compounds of Formula (I) for Barnyard Grass (after emergence, control effect %)

| Compound | | 221 | 225 | 241 | 245 | 246 | 248 | 250 | 291 | $KC_1$ | $KC_2$ |
|---|---|---|---|---|---|---|---|---|---|---|---|
| Dose | 37.5 | 100 | 100 | 98 | 98 | 98 | 100 | 100 | 100 | 25 | 90 |
| g a.i./$hm^2$ | 9.375 | 98 | 95 | 95 | 95 | 95 | 90 | 90 | 90 | 0 | 75 |

The invention claimed is:

1. A triazine benzoate compound of formula I and an optical isomer thereof:

I

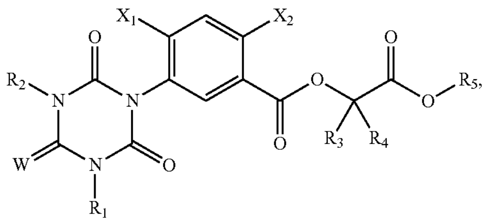

wherein:

W is O or S;

$X_1$ is H or F;

$X_2$ is $CONH_2$ or $CSNH_2$;

$R_1$ is methyl or ethyl;

$R_2$ is methyl or ethyl;

$R_3$ is H or methyl;

$R_4$ is H or $C_1$-$C_3$ alkyl, with the proviso that $R_3$ and $R_4$ are not simultaneously H;

$R_5$ is selected from

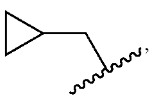, 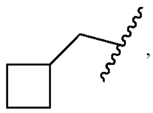, 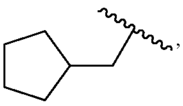,

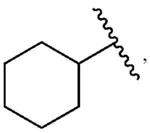, 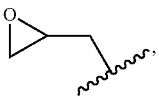, 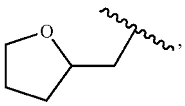,

-continued

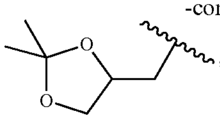, and 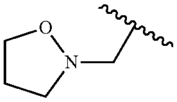, wherein phenyl, phenyl $C_1$-$C_6$ alkyl, alicyclic heterocycle, and aromatic heterocycle are optionally substituted by one or more of substituents selected from nitro, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_3$-$C_6$ cycloalkoxy, $C_2$-$C_6$ alkenyl, $C_2$-$C_6$ alkynyl, phenyl, and phenyl substituted by one or more halogens.

2. A herbicidal composition, comprising an active ingredient and an acceptable carrier, wherein the active ingredient is the compound of the formula I or the optical isomer thereof in claim 1, wherein a weight percentage of the active ingredient in the composition is 1-99%.

3. A method for controlling weeds, comprising applying a herbicidally effective dose of the herbicidal composition of claim 2 to a weed or a growth medium or site of the weed.

* * * * *